US012741971B2

(12) United States Patent
Polla et al.

(10) Patent No.: US 12,741,971 B2
(45) Date of Patent: Sep. 22, 2026

(54) CERTAIN 2,5-DIAZABICYCLO[4.2.0]OCTANES AND OCTAHYDROFURO[3,4-B]PYRAZINES AS GLP-1 RECEPTOR MODULATORS

(71) Applicant: ASTRAZENECA AB, Sodertalje (SE)

(72) Inventors: Magnus Polla, Sodertalje (SE); Joakim Bergman, Sodertalje (SE); Johan Sundell, Sodertalje (SE); Jonas Brånalt, Sodertalje (SE); Ekaterina Ratkova, Sodertalje (SE); Johan Kajanus, Sodertalje (SE); Magnus Johansson, Sodertalje (SE)

(73) Assignee: ASTRAZENECA AB, Sodertalje (SE)

( * ) Notice: Subject to any disclaimer, the term of this patent is extended or adjusted under 35 U.S.C. 154(b) by 336 days.

(21) Appl. No.: 18/698,421

(22) PCT Filed: Oct. 4, 2022

(86) PCT No.: PCT/EP2022/077533

§ 371 (c)(1),
(2) Date: Apr. 4, 2024

(87) PCT Pub. No.: WO2023/057429

PCT Pub. Date: Apr. 13, 2023

(65) Prior Publication Data

US 2025/0115612 A1 Apr. 10, 2025

Related U.S. Application Data

(60) Provisional application No. 63/264,442, filed on Nov. 23, 2021, provisional application No. 63/262,110, filed on Oct. 5, 2021, provisional application No. 63/262,107, filed on Oct. 5, 2021.

(51) Int. Cl.

| | |
|---|---|
| ***C07D 491/048*** | (2006.01) |
| ***A61K 31/498*** | (2006.01) |
| ***A61K 31/4985*** | (2006.01) |
| ***C07D 401/14*** | (2006.01) |
| ***C07D 405/14*** | (2006.01) |
| ***C07D 413/14*** | (2006.01) |

(52) U.S. Cl.

CPC ........ *C07D 491/048* (2013.01); *A61K 31/498* (2013.01); *A61K 31/4985* (2013.01); *C07D 401/14* (2013.01); *C07D 405/14* (2013.01); *C07D 413/14* (2013.01)

(58) Field of Classification Search

None

See application file for complete search history.

(56) References Cited

U.S. PATENT DOCUMENTS

2018/0170908 A1 6/2018 Aspnes et al.

FOREIGN PATENT DOCUMENTS

| | | | |
|---|---|---|---|
| CN | 113480534 | A | 10/2021 |
| CN | 113493447 | A | 10/2021 |
| CN | 113816948 | A | 12/2021 |
| CN | 113831337 | A | 12/2021 |
| CN | 114478497 | A | 5/2022 |
| CN | 114591296 | A | 6/2022 |
| CN | 114591308 | A | 6/2022 |
| CN | 114634510 | A | 6/2022 |
| CN | 114716423 | A | 7/2022 |
| CN | 114763352 | A | 7/2022 |
| CN | 114805336 | A | 7/2022 |
| CN | 114907351 | A | 8/2022 |
| WO | 2018109607 | A1 | 6/2018 |
| WO | 2019239319 | A1 | 12/2019 |
| WO | 2019239371 | A1 | 12/2019 |
| WO | 2020103815 | A1 | 5/2020 |
| WO | 2020207474 | A1 | 10/2020 |
| WO | 2020234726 | A1 | 11/2020 |
| WO | 2020263695 | A1 | 12/2020 |
| WO | 2021018023 | A1 | 2/2021 |
| WO | 2021081207 | A1 | 4/2021 |

(Continued)

OTHER PUBLICATIONS

Bailey C.J., "GIP Analogues and the Treatment of Obesity-diabetes", Peptides, vol. 125, Article 170202, Mar. 2020, pp. 1-26.

Berge S.M., et al., "Pharmaceutical Salts," Journal of Pharmaceutical Sciences, vol. 66, No. 1, Jan. 1977, pp. 1-19, XP002675560.

Buse J.B., et al., "2019 Update to: Management of Hyperglycemia in Type 2 Diabetes, 2018. A Consensus Report by the American Diabetes Association (ADA) and the European Association for the Study of Diabetes (EASD)", Diabetes Care, vol. 43, No. 2, Feb. 2020, pp. 1-7.

Davies M., et al., "Effect of Oral Semaglutide Compared With Placebo and Subcutaneous Semaglutide on Glycemic Control in Patients With Type 2 Diabetes: A Randomized Clinical Trial", JAMA, vol. 318, No. 15, Oct. 17, 2017, pp. 1460-1470.

(Continued)

*Primary Examiner* — Jennifer A Berrios
*Assistant Examiner* — Sophia Reilly
(74) *Attorney, Agent, or Firm* — Global IP

(57) ABSTRACT

There are disclosed certain 2,5-diazabicyclo[4.2.0]octanes of formula (I) and octahydrofuro[3,4-b]pyrazines, and pharmaceutically acceptable salts thereof, together with compositions containing them and their use in therapy. The compounds are GLP-1 receptor modulators and are thereby particularly useful in the treatment or prophylaxis of cardiovascular disease and metabolic conditions, for example Type 2 diabetes.

(I)

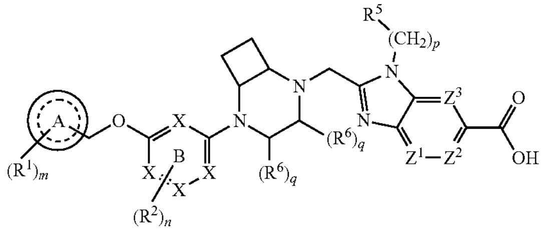

7 Claims, No Drawings

(56) References Cited

FOREIGN PATENT DOCUMENTS

| | | | |
|---|---|---|---|
| WO | 2021096284 | A1 | 5/2021 |
| WO | 2021096304 | A1 | 5/2021 |
| WO | 2021112538 | A1 | 6/2021 |
| WO | 2021116874 | A1 | 6/2021 |
| WO | 2021154796 | A1 | 8/2021 |
| WO | 2021160127 | A1 | 8/2021 |
| WO | 2021197464 | A1 | 10/2021 |
| WO | 2021219019 | A1 | 11/2021 |
| WO | 2021244645 | A1 | 12/2021 |
| WO | 2021249492 | A1 | 12/2021 |
| WO | 2021254470 | A1 | 12/2021 |
| WO | 2022007979 | A1 | 1/2022 |
| WO | 2022028572 | A1 | 2/2022 |
| WO | 2022031994 | A1 | 2/2022 |
| WO | 2022040600 | A1 | 2/2022 |
| WO | 2022042691 | A1 | 3/2022 |
| WO | 2022068772 | A1 | 4/2022 |
| WO | 2022078152 | A1 | 4/2022 |
| WO | 2022078380 | A1 | 4/2022 |
| WO | 2022078407 | A1 | 4/2022 |
| WO | 2022109182 | A1 | 5/2022 |
| WO | 2022111624 | A1 | 6/2022 |
| WO | 2022165076 | A1 | 8/2022 |
| WO | 2022184849 | A1 | 9/2022 |
| WO | 2022192428 | A1 | 9/2022 |
| WO | 2022192430 | A1 | 9/2022 |

OTHER PUBLICATIONS

Eckel R.H., et al., "The Metabolic Syndrome", Lancet, vol. 365, No. 9468, Apr. 2005, pp. 1415-1428.

Griffith D.A., et al., "A Small-Molecule Oral Agonist of the Human Glucagon-like Peptide-1 Receptor", Journal of Medicinal Chemistry, vol. 65, No. 12, Jun. 23, 2022, pp. 8208-8226.

Holst J.J., "From the Incretin Concept and the Discovery of GLP-1 to Today's Diabetes Therapy", Frontiers in Endocrinology, vol. 10, Article 260, Apr. 2019, pp. 1-10.

International Search Report and Written Opinion for International Application No. PCT/EP2022/077533, mailed Feb. 10, 2023, 11 Pages.

Kahn S.E., et al., "Pathophysiology and Treatment of Type 2 Diabetes: Perspectives on the Past, Present, and Future", Lancet, vol. 383, No. 9922, Mar. 22, 2014, pp. 1068-1083.

Ma H., et al., "Structural Insights into the Activation of GLP-1R by a Small Molecule Agonist", Cell Research, vol. 30, No. 12, Dec. 2020, pp. 1140-1142.

Miller C.L., et al., "Targeting Cyclic Nucleotide Phosphodiesterase in the Heart: Therapeutic Implications", Journal of Cardiovascular Translational Research, vol. 3, No. 5, Jul. 15, 2010, pp. 507-515.

Movsesian M.A., et al., "Inhibitors of Cyclic Nucleotide Phosphodiesterase PDE3 as Adjunct Therapy for Dilated Cardiomyopathy", Expert Opinion on Investigational Drugs, vol. 11, No. 11, 2002, pp. 1529-1536.

Movsesian M.A., et al., "Phosphodiesterase Inhibition in Heart Failure", In: Phosphodiesterases as Drug Targets, Handbook of Experimental Pharmacology, vol. 204, 2011, pp. 237-249.

Nauck M.A., et al., "Secretion of Incretin Hormones (GIP and GLP-1) and Incretin Effect After Oral Glucose in First- degree Relatives of Patients with Type 2 Diabetes", Regulatory Peptides, vol. 122, No. 3, Nov. 15, 2004, pp. 209-217.

Nauck M.A., et al., "Incretin Hormones: Their Role in Health and Disease", Diabetes, Obesity and Metabolism, vol. 20, Suppl. 1, Feb. 2018, pp. 5-21.

Nauck M.A., et al., "Normalization of Fasting Hyperglycemia by Exogenous Glucagon-like Peptide 1 (7-36 Amide) in Type 2 (Non-insulin-dependent) Diabetic Patients", Diabetologia, vol. 36, No. 8, Aug. 1993, pp. 741-744.

Rautio J., et al., "Prodrugs: Design and Clinical Applications", Nature Reviews Drug Discovery, vol. 7, Mar. 2008, pp. 255-270.

Tsonkova V.G., et al., "The EndoC-bH1 Cell Line Is a Valid Model of Human Beta Cells and Applicable for Screenings to Identify Novel Drug Target Candidates", Molecular Metabolism, vol. 8, Feb. 2018, pp. 144-157.

CERTAIN 2,5-DIAZABICYCLO[4.2.0]OCTANES AND OCTAHYDROFURO[3,4-B]PYRAZINES AS GLP-1 RECEPTOR MODULATORS

TECHNICAL FIELD

The technical field relates to certain 2,5-diazabicyclo [4.2.0]octanes and octahydrofuro[3,4-b]pyrazines, to their use in the treatment of cardiovascular disease and metabolic conditions, for example type 2 diabetes, and to pharmaceutical compositions containing them.

BACKGROUND

Obesity and type 2 diabetes (T2D) are major and growing health problems worldwide (*Lancet,* 2014, 9922, 1068-1083). The two diseases are strongly associated with each other, with obesity proceeding development of insulin resistance and T2D. T2D is associated with several comorbidities including cardiovascular disease, renal disease, hypertension, stroke, non-alcoholic fatty liver disease (NAFLD) and non-alcoholic steatohepatitis (NASH) (*Lancet,* 2005, 9468, 1415-1428).

Incretin hormones including GLP-1 (glucagon-like peptide-1) and GIP (glucose-dependent insulinotropic polypeptide) are gut peptides that are secreted after nutrient intake and stimulate insulin secretion (*Diabetes Obes Metab.,* 2018, 20 (Suppl. 1), 5-21). GLP-1 secretion from the gut is impaired in obese subjects which may indicate a role in the pathophysiology of obesity (*Regulatory Peptides,* 2004, 122, 209-217).

GLP-1 is secreted from the L-cells in the lower gut in response to food intake. GLP-1 stimulates insulin secretion from the pancreatic β-cells, in a glucose dependent manner (*Diabetologia,* 1993, 36, 741-744). GLP-1 also inhibits glucagon secretion, reduces appetite and slows down gastric emptying. The GLP-1 receptor is also present in the heart, kidneys and immune system and activation has been shown to reduce blood pressure, increase natriuresis and decrease inflammation.

GLP-1 is a 37-amino acid peptide, post-translationally processed from pro-glucagon, a 158 amino acid precursor polypeptide (www.uniprot.org, pro-glucagon entry P01275). Several other peptides are also derived from proglucagon and processed in a tissue specific manor, including glucagon and oxyntomodulin. GLP-1 has very short half-life in vivo as it is rapidly degraded by dipeptidyl peptidase-4 (DPP-IV) (*Front. Endocrinol.* 2019, 10, Article 260, 1-10).

Incretin-based glucose- and body weight-lowering medications include GLP-1 receptor agonists, DPP-IV inhibitors and more recently also combinations of GLP-1 agonists and glucose-dependent insulinotropic polypeptide (GIP) agonists (*Peptides,* 2020, 125, Article 170202). Traditionally GLP-1 analogues are peptide hormones which have been modified to minimize DPP-IV cleavage and are administered as injectables. The first oral GLP-1 peptide was recently approved but bioavailability is low and the drug needs to be administered in the fasting state, 30 min before nutrient intake which may limit patient compliance (*JAMA,* 2017, 318(15), 1460-1470). The injectable peptides show increased efficacy over the oral peptides but are limited by the route of administration. Small molecule GLP-1 receptor agonists are in development from several companies and are expected to provide a therapeutic benefit versus peptide based therapies due to early use in the treatment paradigm.

Pharmacological stimulation of GLP-1 receptors has been shown to significantly reduce HbA1c levels, provide long term weight loss and reduce blood pressure. GLP-1 receptor agonists have also been shown to reduce cardiovascular events and prolong life in high-risk patients with T2D and are therefore recommended by the European Association for the Study of Diabetes (EASD) and American Diabetes Association (ADA) in patients with multiple risk factors of cardiovascular disease (CVD) independent of the patients glycemic control (*Diabetes Care,* 2020, 43, 487-493).

There remains a need for an easily-administered prevention and/or treatment for cardiometabolic and associated diseases.

WO2018/109607 discloses 6-carboxylic acids of benzimidazoles and 4-aza-, 5-aza-, 7-aza- and 4,7-diazabenzimidazoles as GLP-1 receptor agonists, processes to make said compounds, and methods comprising administering said compounds to a mammal in need thereof.

WO2019/239319 and WO2019/239371 disclose 6-carboxylic acids of benzimidazoles and 4-aza-, 5-aza- and 7-aza-benzimidazoles as GLP-1 receptor agonists, processes to make said compounds, and methods comprising administering said compounds to a mammal in need thereof.

WO2020/103815 disclose GLP-1 receptor agonist compounds and pharmaceutical compositions thereof, for use in e.g. treating type 2 diabetes mellitus, pre-diabetes, obesity, non-alcoholic fatty liver disease, non-alcoholic steatohepatitis and cardiovascular disease.

WO2020/207474 disclose GLP-1 receptor agonist compounds and pharmaceutical compositions thereof, for use in e.g. treating type 2 diabetes mellitus, pre-diabetes, obesity, non-alcoholic fatty liver disease, non-alcoholic steatohepatitis and cardiovascular disease.

WO2020/234726 disclose combinations of GLP-1 receptor agonist compounds and pharmaceutical compositions thereof and an acetyl-CoA carboxylase (ACC) inhibitor or a diacylglycerol acyltransferase (DGAT2) inhibitor, or a ketohexokinase (KHK) inhibitor or farnesoid X receptor (FXR) agonist, for use in e.g. treating type 2 diabetes mellitus, pre-diabetes, obesity, non-alcoholic fatty liver disease, non-alcoholic steatohepatitis and related diseases.

WO2020/263695 discloses glucagon-like peptide-1 receptor agonists and therapeutic uses of the compounds to treat type II diabetes mellitus.

WO2021/081207 discloses compounds that bind to and act as agonists or modulators of the glucagon-like peptide-1 receptor (GLP-1R) and act as agonists or modulators of GLP-1R. The disclosure further relates to the use of the compounds for the treatment and/or prevention of diseases and/or conditions by said compounds.

WO2021/018023 discloses compounds for modulating a glucagon-like peptide-1 (GLP-1) receptor, and a pharmaceutical use thereof.

WO2021/096284 and WO2021/096304 discloses compounds that act as GLP-1 receptor agonists, for use as therapeutic agents for metabolic diseases.

WO2021/112538 discloses compounds which serves as a GLP-1 receptor agonist and may be useful in the prevention or treatment of a disease associated with GLP-1 activity.

WO2021/154796 discloses GLP-1R agonists, and compositions, methods, and kits thereof. Such compounds are generally useful for treating a GLP-1R mediated disease or condition.

WO2021/160127 discloses GLP-1 agonists, pharmaceutical compositions, and methods of use thereof.

WO2021116874 discloses of solid forms of 2-[[4-[(S)-2-(5-chloropyridin-2-yl)-2-methylbenzo[d][1,3]dioxol-4-yl]

piperidin-1-yl]methyl]-1-[[(S)-oxetan-2-yl]methyl]-1H-benzo[d]imidazole-6-carboxylic acid, 1,3-dihydroxy-2-(hydroxymethyl)propan-2-amine salt for pharmaceutical use.

CN113493447A discloses a compound that can be used as a GLP-1 receptor agonist. WO2021197464 discloses fused imidazole derivatives, preparation methods and medical use as a therapeutic agent, especially as GLP-1 receptor agonists.

CN113480534A discloses benzimidazole or azabenzimidazole-6-carboxylate compound that can activate GLP-1R downstream signaling pathway.

WO2021154796 discloses compounds as GLP-1R agonists, and compositions, methods, and kits thereof.

WO2021219019 discloses GLP-1 agonists of formula I, including pharmaceutically acceptable salts and solvates thereof, pharmaceutical compositions, and methods of using the same.

WO2021244645 discloses five-membered heteroaromatic imidazole compounds I and their medical use.

WO2021249492 discloses methyl-substituted benzobisoxazole compound and the use thereof in the preparation of drugs for treating related diseases.

CN113816948A discloses fused imidazole derivatives as GLP-1 receptor agonist in the treatment of diabetes.

WO2021254470 discloses preparation of 6-oxo-3,6-dihydropyridine derivative and a pharmaceutical composition containing the derivative, are used as therapeutic agents, in particular as GLP-1 receptors agonist and in the preparation of drugs for the treatment and/or prevention of diabetes.

WO2022007979 discloses a fused imidazole derivative, a preparation method therefor, a pharmaceutical composition containing the derivative, and the use of same as a therapeutic agent, in particular the use thereof as a GLP-1 receptor agonist.

CN113831337A discloses heterocyclic nitrogen compounds as GLP-1 receptor agonist.

WO2022068772 discloses a kind of benzimidazole derivative, its preparation method and application as GLP-1R agonists.

WO2022042691 discloses GLP-1 agonists, including pharmaceutically acceptable salts and solvates thereof, and pharmaceutical compositions including the same.

WO2022040600 discloses compounds that may be used as a glucagon-like peptide-1 receptors (GLP-1R) agonist.

WO2022028572 discloses GLP-1 agonists, including pharmaceutically acceptable salts and solvates thereof, and pharmaceutical compositions including the same.

WO2022031994 discloses compounds and pharmaceutical compositions thereof, for use in, e.g. treating type 2 diabetes mellitus, pre-diabetes, obesity, non-alc. fatty liver disease, non-alc. steatohepatitis, and cardiovascular disease.

CN114591308A discloses piperazine-imidazole containing GLP-1R receptor agonist compounds and application thereof.

WO2022111624 discloses benzimidazole derivatives that are agonists of a glucagon-like peptide-1 receptor (GLP-1R).

WO2022109182 discloses polyheterocyclic benzimidazole compounds and their preparation and use in the treatment of GLP-1R mediated diseases.

CN114478497A discloses a kind of aryl alkyl acid GLP-1 receptor agonist, its preparation method and application in treatment or prevention of GLP-1-mediated diseases and related diseases.

WO2022078380 discloses compounds that are GLP-1 agonists.

WO2022078407 discloses compounds that are GLP-1 agonists.

WO2022078152 discloses a kind of benzimidazolone compounds, their preparation method and application as GLP-1 receptor agonist.

CN114716423A discloses 5,6-dihydro-1,2,4-triazine compounds as GLP-1 receptor agonist.

CN114634510A discloses imidazolopyridine derivatives, which can be used to prepare drugs for treating GLP-1 receptor agonist mediated diseases.

CN114591296A discloses aromatic heterocyclic derivatives as GLP-1R agonists.

WO2022192430 discloses GLP-1R agonists and compositions, methods, and kits thereof.

WO2022192428 discloses GLP-1R agonists and compositions, methods, and kits thereof.

WO2022184849 discloses GLP-1R agonists, uses and pharmaceutical compositions thereof.

CN114907351A discloses tricyclic GLP-1 receptor agonists.

WO2022165076 discloses substituted benzimidazolecarboxylic acids which are GLP-1 receptor modulator compounds.

CN114805336A discloses fused imidazole compounds that are GLP-1 receptor agonists.

CN114763352A discloses benzimidazole derivatives and its application as GLP-1 receptor agonist. J. Med. Chem. 2022, 65, 12, 8208-8226 discloses A Small-Molecule Oral Agonist of the Human Glucagon-like Peptide-1 Receptor. Cell Research 2020, (39), 1140-1142 discloses structural insights into the activation of GLP-1R by a small molecule agonist.

An object is to provide novel GLP-1 receptor modulators useful in therapy. A further object is to provide novel compounds having improved safety profile, e.g. with regards to selectivity for the GLP-1 receptor over e.g. phosphodiesterase 3 (PDE3) and/or having improved metabolic stability in the body.

SUMMARY

There is provided compounds that are modulators of the glucagon-like peptide-1 (GLP1) receptor, their use as medicaments, pharmaceutical compositions containing them and synthetic routes to their production.

In one embodiment, there is provided a compound of Formula (I), (I)

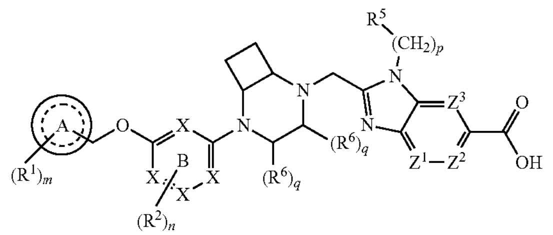

or a compound of Formula (II), (II)

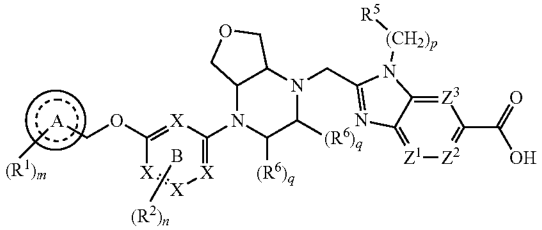

wherein

A is phenyl or pyridyl;

X is independently N or C, provided that no more than two atoms in the aromatic ring B are N;

$Z^1$ is N or $CR^3$;

$Z^2$ and $Z^3$ are each independently N or $CR^4$, provided that when $Z^1$ or $Z^3$ is N, $Z^2$ is $CR^4$;

$R^1$ is independently selected from F, Cl, Br, CN, $OCH_3$, $OCFH_2$, $OCF_2H$, $OCF_3$, $CH_3$, $CFH_2$, $CF_2H$ and $CF_3$;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$, $CFH_2$, $CF_2H$, $CF_3$, $OCH_3$, $OCFH_2$, $OCF_2H$ and $OCF_3$;

$R^5$ is selected from (4- to 6-membered)heterocycloalkyl, (5- to 6-membered)heteroaryl, CN, $C_{1-4}$alkyl, $O(C_{1-4}alkyl)$, $S(C_{1-4}alkyl)$, cyclopropyl, cyclobutyl, O(cyclopropyl) or S(cyclopropyl), wherein said (4- to 6-membered)heterocycloalkyl and (5- to 6-membered) heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

$R^6$ is independently selected from F, $C_{1-2}$alkyl and $OC_{1-2}$alkyl, wherein said $C_{1-2}$alkyl is substituted by 0, 1, 2 or 3 substituents independently selected from F;

m is 0, 1, 2 or 3;

n is 0 or 1;

p is 1, 2 or 3;

q is 0, 1 or 2;

or a pharmaceutically acceptable salt thereof.

The compounds of Formula (I) and (II) are modulators of the GLP-1 receptor. Thus, the compounds of Formula (I) and (II) can be used as a medicament, in particular for disorders, disease or conditions responsive to modulation of the GLP-1 receptor, and more specifically cardiovascular disease and metabolic conditions.

In another embodiment there is provided a compound of Formula (I) or (II), or a pharmaceutically acceptable salt of a compound of Formula (I) or (II), wherein the stereochemistry is undefined, e.g. a racemate or a mixture of diastereomers.

In another embodiment there is provided a compound of Formula (I) or (II), or a pharmaceutically acceptable salt of a compound of Formula (I) or (II), wherein the stereochemistry is defined.

In another embodiment there is provided a pharmaceutical formulation comprising a therapeutically effective amount of a compound of Formula (I) or (II), or a pharmaceutically acceptable salt of a compound of Formula (I) or (II), and a pharmaceutically acceptable diluent, excipient and/or inert carrier.

In a further embodiment there is provided a pharmaceutical formulation comprising a compound of Formula (I) or (II), or a pharmaceutically acceptable salt of a compound of Formula (I) or (II), for use in the treatment of a condition where modulation of the GLP-1 receptor would be beneficial.

In a further embodiment there is provided a compound of Formula (I) or (II), or a pharmaceutically acceptable salt of a compound of Formula (I) or (II), for use in therapy, especially in the treatment of cancer in a mammal, particularly a human.

In a further embodiment there is provided the use of a compound of Formula (I) or (II), or a pharmaceutically acceptable salt of a compound of Formula (I) or (II), for the manufacture of a medicament for the treatment of cardiovascular disease and metabolic conditions.

According to another aspect there is provided processes for the preparation of compounds of Formula (I) or (II), or pharmaceutically acceptable salts of compounds of Formula (I) or (II), and the intermediates used in the preparation thereof.

The compounds of Formula (I) and (II) described herein have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

DETAILED DESCRIPTION

This detailed description and its specific examples, while indicating embodiments, are intended for purposes of illustration only. Therefore, there is no limitation to the illustrative embodiments described in this specification. In addition, it is to be appreciated that various features that are, for clarity reasons, described in the context of separate embodiments, also may be combined to form a single embodiment. Conversely, various features that are, for brevity reasons, described in the context of a single embodiment, also may be combined to form sub-combinations thereof.

Listed below are definitions of various terms used in the specification and claims.

It is to be understood that where in this specification a group is qualified by "defined above" the said group encompasses the first occurring and broadest definition as well as each and all of the other definitions for that group.

In this specification, the term "modulator" is used to describe a compound that exhibit varying receptor agonism, either full agonism, or partial agonism.

It is to be understood that in this specification "$C_{1-4}$" means a carbon group having 1, 2, 3 or 4 carbon atoms.

It is to be understood that in this specification "$C_{1-2}$" means a carbon group having 1 or 2 carbon atoms.

In this specification, unless stated otherwise, the term "alkyl" includes both straight and branched chain alkyl groups and may be, but is not limited to, methyl, ethyl, n-propyl, i-propyl, n-butyl, sec-butyl, iso-butyl or tert-butyl.

It is to be understood that in this specification "(5- to 6-membered)heteroaryl" means an aromatic ring with 5 to 6 atoms and containing one or more heteroatoms independently selected from nitrogen, oxygen or sulphur.

It is to be understood that in this specification "(6-membered)heteroaryl" means an aromatic ring with 6 atoms and containing one or more heteroatoms independently selected from nitrogen, oxygen or sulphur.

It is to be understood that in this specification "(6-membered)heteroaryl" means for example pyridine.

It is to be understood that in this specification "(5-membered)heteroaryl" means an aromatic ring with 5 atoms and containing one or more heteroatoms independently selected from nitrogen, oxygen or sulphur.

It is to be understood that in this specification "(4- to 5-membered)heterocycloalkyl" means a partially or completely saturated ring system with 4 to 5 atoms and wherein at least one of the ring carbon atoms is replaced with a heteroatom independently selected from nitrogen, oxygen or sulphur.

It is to be understood that in this specification a "heterocycloalkyl" substituent may be attached via a nitrogen atom having the appropriate valences, or via any ring carbon atom.

It is to be understood that in this specification a "heterocycloalkyl" or "heteroaryl" substituent may be further substituted, for example by a substituent selected from $C_{1-2}$alkyl.

In this specification, unless stated otherwise, the term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

There is provided compounds of Formula (I) and (II) wherein X, $Z^1$, $Z^2$, $Z^3$, $R^1$-$R^6$, m, n, p and q are as defined in Formula (I) and (II).

In one embodiment X is independently N or C, provided that no more than two atoms in the aromatic ring B are N.

In a further embodiment X is N.

In still a further embodiment X is N or C.

In one embodiment $Z^1$ is N or $CR^3$.

In a further embodiment $Z^1$ is N.

In still a further embodiment $Z^1$ is $CR^3$.

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F.

In one embodiment $Z^2$ and $Z^3$ are each independently N or $CR^4$, provided that when $Z^1$ or $Z^3$ is N, $Z^2$ is $CR^4$.

In a further embodiment $Z^1$ and $Z^2$ are N.

In still a further embodiment $Z^1$ and $Z^3$ are N.

In still a further embodiment $Z^2$ and $Z^3$ are N.

In still a further embodiment $Z^1$ is N, $Z^2$ and $Z^3$ are $CR^4$.

In still a further embodiment $Z^2$ is N, $Z^1$ and $Z^3$ are $CR^4$.

In still a further embodiment $Z^3$ is N, $Z^1$ and $Z^2$ are $CR^4$.

In still a further embodiment $Z^1$, $Z^2$ and $Z^3$ are $CR^4$.

$R^4$ is independently selected from H, F, Cl, OH, $CH_3$, $CFH_2$, $CF_2H$, $CF_3$, $OCH_3$, $OCFH_2$, $OCF_2H$ and $OCF_3$.

In one embodiment $R^1$ is 0, 1, 2 or 3 substituents independently selected from F, Cl, Br, CN, $OCH_3$, $OCFH_2$, $OCF_2H$, $OCF_3$, $CH_3$, $CFH_2$, $CF_2H$ and $CF_3$.

In a further embodiment $R^1$ is 0, 1 or 2 substituents independently selected from F, Cl, Br, CN, $OCH_3$, $OCFH_2$, $OCF_2H$, $OCF_3$, $CH_3$, $CFH_2$, $CF_2H$ and $CF_3$.

In still a further embodiment $R^1$ is 0, 1, 2 or 3 substituents independently selected from F, Cl, Br, CN, $OCH_3$.

In still a further embodiment $R^1$ is 0, 1 or 2 substituents independently selected from F, Cl, Br, CN, $OCH_3$.

In still a further embodiment $R^1$ is 0, 1 or 2 substituents independently selected from F, Cl and CN.

In still a further embodiment $R^1$ is 0 or 1 substituents selected from F, Cl and CN.

In one embodiment $R^2$ is selected from 0 or 1 F, Cl or CN.

In one embodiment $R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F.

In a further embodiment $R^3$ is selected from H, F, Cl, $C_{1-2}$alkyl and $OC_{1-2}$alkyl, wherein said $C_{1-2}$alkyl is substituted by 0, 1, 2 or 3 F.

In still a further embodiment $R^3$ is selected from H, F, Cl, $CH_3$, $CFH_2$, $CF_2H$, $CF_3$, $OCH_3$, $OCFH_2$, $OCF_2H$ and $OCF_3$.

In still a further embodiment $R^3$ is selected from H, F, Cl, $CH_3$ and $OCH_3$.

In one embodiment $R^4$ is independently selected from H, F, Cl, OH, $CH_3$, $CFH_2$, $CF_2H$, $CF_3$, $OCH_3$, $OCFH_2$, $OCF_2H$ and $OCF_3$.

In a further embodiment $R^4$ is independently selected from H, F, Cl, OH, $CH_3$ and $OCH_3$.

In still a further embodiment $R^4$ is independently selected from H, F, Cl, $CH_3$ and $OCH_3$.

In still a further embodiment $R^4$ is independently selected from H, F and Cl.

In one embodiment $R^5$ is selected from (4- to 6-membered)heterocycloalkyl, (5- to 6-membered)heteroaryl, CN, $C_{1-4}$alkyl, $O(C_{1-4}alkyl)$, $S(C_{1-4}alkyl)$, cyclopropyl, cyclobutyl, O(cyclopropyl) or S(cyclopropyl), wherein said (4- to 6-membered)heterocycloalkyl and (5- to 6-membered) heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F.

In a further embodiment $R^5$ is selected from $C_{1-4}$alkyl, $O(C_{1-4}alkyl)$ and $S(C_{1-4}alkyl)$, wherein said $C_{1-4}$alkyl is substituted by 0 or 1 substituent selected from CN or $OCH_3$, and 0, 1, 2 or 3 F.

In still a further embodiment $R^5$ is selected from cyclopropyl, cyclobutyl, O(cyclopropyl) or S(cyclopropyl), said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F.

In still a further embodiment $R^5$ is selected from (4- to 6-membered)heterocycloalkyl and (5- to 6-membered)heteroaryl, wherein said (4- to 6-membered)heterocycloalkyl and (5- to 6-membered)heteroaryl is substituted by 0 or 1 substituent selected from $C_{1-2}$alkyl.

In still a further embodiment $R^5$ is selected from (5- to 6-membered)heteroaryl, wherein said (5- to 6-membered) heteroaryl is substituted by 0 or 1 substituent selected from $C_{1-2}$alkyl.

In still a further embodiment $R^5$ is selected from (4- to 6-membered)heterocycloalkyl, wherein said (4- to 6-membered)heterocycloalkyl is substituted by 0 or 1 substituent selected from $C_{1-2}$alkyl.

In still a further embodiment $R^5$ is oxetan-2-yl.

In one embodiment $R^6$ is independently selected from F, $C_{1-2}$alkyl and $OC_{1-2}$alkyl, wherein said $C_{1-2}$alkyl is substituted by 0, 1, 2 or 3 substituents independently selected from F.

In a further embodiment $R^6$ is independently selected from F, $C_{1-2}$alkyl and $OC_{1-2}$alkyl.

In still a further embodiment $R^6$ is independently selected from F, $CH_3$ and $OCH_3$.

In one embodiment m is 0, 1, 2 or 3.

In a further embodiment m is 0, 1, or 2.

In still a further embodiment m is 1 or 2

In still a further embodiment m is 0 or 1.

In still a further embodiment m is 1.

In still a further embodiment m is 0.

In one embodiment n is 0 or 1.

In a further embodiment n is 1.

In still a further embodiment n is 0.

In one embodiment p is 1, 2 or 3.

In a further embodiment p is 1 or 2.

In still a further embodiment p is 1.

In one embodiment q is 0, 1 or 2.

In a further embodiment q is 0 or 1.

In still a further embodiment q is 0.

In one embodiment, there is provided a compound of Formula (Ia), (Ia)

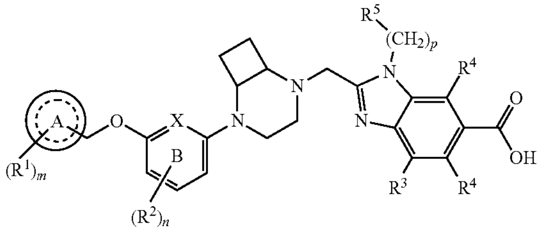

or Formula (Ha), (IIa)

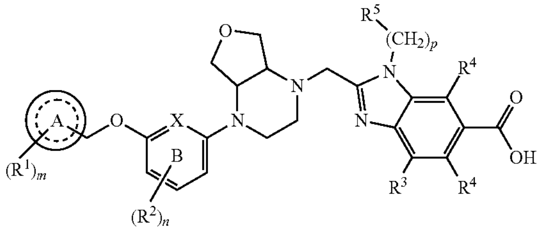

wherein

A is phenyl or pyridyl;

X is N or C;

$R^1$ is independently selected from F, Cl, Br, CN, $OCH_3$, $OCFH_2$, $OCF_2H$, $OCF_3$, $CH_3$, $CFH_2$, $CF_2H$ and $CF_3$;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$, $CFH_2$, $CF_2H$, $CF_3$, $OCH_3$, $OCFH_2$, $OCF_2H$ and $OCF_3$;

$R^5$ is selected from (4- to 6-membered)heterocycloalkyl, (5- to 6-membered)heteroaryl, CN, $C_{1-4}$alkyl, O($C_{1-4}$alkyl), S($C_{1-4}$alkyl), cyclopropyl, cyclobutyl, O(cyclopropyl) or S(cyclopropyl), wherein said (4- to 6-membered)heterocycloalkyl and (5- to 6-membered) heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

m is 0, 1, 2 or 3;

n is 0 or 1;

p is 1, 2 or 3;

q is 0, 1 or 2;

or a pharmaceutically acceptable salt thereof.

In a further embodiment, there is provided a compound of Formula (Ia) or (IIa), wherein A is phenyl;

X is N;

$R^1$ is independently selected from F, Cl and CN;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$ and $OCH_3$;

$R^5$ is selected from (4- to 6-membered)heterocycloalkyl, (5- to 6-membered)heteroaryl, CN, $C_{1-4}$alkyl, O($C_{1-4}$alkyl), S($C_{1-4}$alkyl), cyclopropyl, cyclobutyl, O(cyclopropyl) or S(cyclopropyl), wherein said (4- to 6-membered)heterocycloalkyl and (5- to 6-membered) heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

m is 0, 1 or 2;

n is 0 or 1;

p is 1, 2 or 3;

or a pharmaceutically acceptable salt thereof.

In still a further embodiment, there is provided a compound of Formula (Ia) or (IIa), wherein A is phenyl;

X is N;

$R^1$ is independently selected from F, Cl and CN;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$ and $OCH_3$;

$R^5$ is selected from (4- to 6-membered)heterocycloalkyl wherein said (4- to 6-membered)heterocycloalkyl is substituted by 0 or 1 substituent selected from $C_{1-2}$alkyl and;

m is 0, 1 or 2;

n is 0 or 1;

p is 1;

or a pharmaceutically acceptable salt thereof.

In one embodiment the compounds of Formula (I) and (II) are selected from:

2-(((1R,6S)-5-(6-((4-Cyano-2-fluorobenzyl)oxy)pyridin-2-yl)-2,5-diazabicyclo[4.2.0]octan-2-yl)methyl)-1-((1-methyl-1H-pyrazol-3-yl)methyl)-1H-benzo[d]imidazole-6-carboxylic acid, 2-(((1R*,6S*)-5-(6-((4-Cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylic acid, 2-(((1R*,6R*)-5-(6-((4-Cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylic acid, 2-(((1R*,6R*)-5-(6-((4-Cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylic acid, 2-(((1R*,6R*)-5-(6-((4-Cyano-2-fluorobenzyl)oxy)pyridin-2-yl)-2,5-diazabicyclo[4.2.0]octan-2-yl)methyl)-5-fluoro-1-(((S)-oxetan-2-yl)methyl)-1H-benzo[d]imidazole-6-carboxylic acid, rel-4-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, rel-5-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, rel-7-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, 2-(((1R*,6R*)-5-(6-((4-Chloro-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylic acid, rac-1-(2-(tert-Butoxy)ethyl)-2-(((1R,6S)-5-(6-((4-cyano-2-fluorobenzyl)oxy)pyridin-2-yl)-2,5-diazabicyclo[4.2.0]octan-2-yl)methyl)-1H-benzo[d]imidazole-6-carboxylic acid, rac-1-(2-Butoxyethyl)-2-(((1R,6S)-5-(6-((4-cyano-2-fluorobenzyl)oxy)pyridin-2-yl)-2,5-diazabicyclo[4.2.0]octan-2-yl)methyl)-1H-benzo[d]imidazole-6-carboxylic acid, rel-2-(((1R,6R)-5-(6-((4-Chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylic acid, rac-2-(((1R,6S)-5-(6-((4-Cyano-2-fluorobenzyl)oxy)pyridin-2-yl)-2,5-diazabicyclo[4.2.0]octan-2-yl)methyl)-1-((5-methylisoxazol-3-yl)methyl)-1H-benzo[d]imidazole-6-carboxylic acid, rac-2-(((1R,6S)-5-(6-((4-Cyano-2-fluorobenzyl)oxy)pyridin-2-yl)-2,5-diazabicyclo[4.2.0]octan-2-yl)methyl)-1-((4-methylpyridin-2-yl)methyl)-1H-benzo[d]imidazole-6-carboxylic acid, 2-(((4aRS,7aSR)-4-(6-((4-Chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid, 2-(((4aR*,7aS*)-4-(6-((4-Chloro-2-fluorobenzyl)oxy)pyridin-2-yl)hexahydrofuro[3,4-b]pyrazin-1(2H)-yl)methyl)-4-methoxy-1-(((S)-oxetan-2-yl)methyl)-1H-benzo[d]imidazole-6-carboxylic acid, 2-(((4aRS,7aSR)-4-(6-((4-Cyano-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid, rel-2-(((4aR,7aS)-4-(6-((4-Chloro-2-fluorobenzyl)oxy)pyridin-2-yl)hexahydrofuro[3,4-b]pyrazin-1(2H)-yl)methyl)-4-fluoro-1-(((S)-tetrahydrofuran-3-yl)methyl)-1H-benzo[d]imidazole-6-carboxylic acid, 2-(((4aR*,7aS*)-4-(6-((4-Chloro-2-fluorobenzyl)oxy)pyridin-2-yl)hexahydrofuro[3,4-b]pyrazin-1(2H)-yl)methyl)-4-fluoro-1-(((S)-oxetan-2-yl)methyl)-1H-benzo[d]imidazole-6-carboxylic acid, rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(oxazol-4-ylmethyl)-1H-benzo[d]imidazole-6-carboxylic acid, rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(pyridin-3-ylmethyl)-1H-benzo[d]imidazole-6-carboxylic acid, 4-Chloro-2-(((4aR*,7aS*)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid, rel-2-(((4aR,7aS)-4-(6-((4-Chloro-2-fluorobenzyl)oxy)pyridin-2-yl)hexahydrofuro[3,4-b]pyrazin-1(2H)-yl)methyl)-4-fluoro-1-(2-(2-methyl-1H-imidazol-1-yl)ethyl)-1H-benzo[d]imidazole-6-carboxylic acid, rel-4-Chloro-2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylic acid, rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylic acid, and pharmaceutically acceptable salts thereof.

It shall be noted that any one of these specific compounds may be disclaimed from any of the herein mentioned embodiments.

In one embodiment there is provided processes for the preparation of compounds of Formula (I) or (II), or pharmaceutically acceptable salts of compounds of Formula (I) or (II), and the intermediates used in the preparation thereof.

Another embodiment is a product obtainable by any of the processes or examples disclosed herein.

Medical and Pharmaceutical Use

The compounds of Formula (I) and (II) and their pharmaceutically acceptable salts are believed to be useful in the prevention or treatment of cardiovascular disease and metabolic conditions, including but not limited to type 2 diabetes (T2D), obesity, non-alcoholic fatty liver disease (NAFLD) and non-alcoholic steatohepatitis (NASH), in a mammal, particularly a human.

For the avoidance of doubt, as used herein, the term "treatment" includes therapeutic and/or prophylactic treatment.

When a compound or salt described herein is administered as therapy for treating a disorder, a "therapeutically effective amount" is an amount sufficient to reduce or completely alleviate symptoms or other detrimental effects of the disorder, cure the disorder, reverse, completely stop, or slow the progress of the disorder or reduce the risk of the disorder getting worse.

The compounds described herein are thus indicated both in the therapeutic and/or prophylactic treatment of these conditions.

The compounds described herein have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

For the above-mentioned therapeutic indications, the dosage administered will vary with the compound employed, the mode of administration and the treatment desired. However, in general, satisfactory results are obtained when the compounds are administered at a dosage of the solid form of between 1 mg and 2000 mg per day.

The compounds of Formula (I) or (II), and pharmaceutically acceptable derivatives thereof, may be used on their own, or in the form of appropriate pharmaceutical compositions in which the compound or derivative is in admixture with a pharmaceutically acceptable adjuvant, diluent or carrier. Thus, another aspect concerns a pharmaceutical composition comprising a novel compound of Formula (I) or (II), or a pharmaceutically acceptable salt thereof, in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical Formulations are described in, for example, *Pharmaceuticals—The Science of Dosage Form Designs*, M. E. Aulton, Churchill Livingstone, 2nd Ed. 2002. In one embodiment the composition preferably comprises less than 80% and in another embodiment less than 50% of a compound of Formula (I) or (II), or a pharmaceutically acceptable salt thereof.

In one embodiment there is provided a compound selected from any one of the compounds of Formula (I) or (II), or a pharmaceutically acceptable salt of a compound of Formula (I) or (II), for use in therapy, especially in the prevention or treatment of cardiovascular disease and metabolic conditions, including but not limited to type 2 diabetes (T2D), obesity, non-alcoholic fatty liver disease (NAFLD) and non-alcoholic steatohepatitis (NASH).

These and other embodiments are described in greater detail herein below, where further aspects will be apparent to one skilled in the art from reading this specification.

Combination Therapy

The compounds of Formula (I) or (II), or pharmaceutically acceptable salts thereof, may also be administered in conjunction with other compounds used for the treatment of the above conditions.

In another embodiment, there is a combination therapy wherein a compound selected from any one of the compounds of Formula (I) or (II), or a pharmaceutically acceptable salt thereof, and a second active ingredient are administered concurrently, sequentially or in admixture, for the treatment of one or more of the conditions listed above. Such a combination may be used in combination with one or more further active ingredients.

When used in a combination therapy, it is contemplated that the a compound selected from any one of the compounds of Formula (I) or (II), or pharmaceutically acceptable salts thereof, and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

Pharmaceutical Compositions

There is provided a method of treatment of a condition where modulation of GLP-1 receptor is required, which method comprises administration of a therapeutically effective amount of a compound selected from any one of the compounds of Formula (I) or (II) to a person suffering from, or susceptible to, such a condition.

The compounds of Formula (I) or (II) will normally be administered via the oral, topical, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt thereof, in a pharmaceutically acceptable dosage form. Depending upon the disorder and patient to be treated and the route of administration, the compositions may be administered at varying doses. Conventional procedures for the selection and preparation of suitable pharmaceutical Formulations are described in, for example, *Pharmaceuticals—The Science of Dosage Form Designs*, M. E. Aulton, Churchill Livingstone, 2nd Ed. 2002.

In one embodiment suitable daily doses of the compounds of Formula (I) or (II) in therapeutical treatment of humans are about 0.0001-100 mg/kg body weight, in another embodiment about 0.01-10 mg/kg body weight.

The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the Formulation; and various other factors known to physicians and others skilled in the art.

According to a further aspect there is thus provided a pharmaceutical Formulation comprising a compound selected from any one of the compounds of Formula (I) or (II), or pharmaceutically acceptable derivatives thereof, in admixture with a pharmaceutically acceptable adjuvant, diluent and/or carrier.

The compound of Formula (I) or (II) may be present in the pharmaceutical Formulation in a concentration from 0.1 to 99.5%, such as from 0.5 to 95%, by weight of the total Formulation.

Preparation of the Compounds

The protection and deprotection of functional groups is described in *Protective Groups in Organic Synthesis*, 4th Ed, T. W. Greene and P. G. M. Wuts, Wiley-Interscience (2006) and *Protecting Groups*, 3rd Ed, P. J. Kocienski, Georg Thieme Verlag (2005).

A further embodiment encompasses pharmaceutically acceptable salts of the compounds of Formula (I) or (II).

A salt of a compound selected from any one of Formula (I) may be advantageous due to one or more of its chemical or physical properties, such as stability in differing temperatures and humidities, or a desirable solubility in $H_2O$, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

The term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

Where the compound is sufficiently basic, pharmaceutically acceptable salts include, but are not limited to, inorganic or organic acid addition salts.

For reviews on suitable salts, see Berge et al., *J. Pharm. Sci.*, 1977, 66, 1-19 or *Handbook of Pharmaceutical Salts: Properties, selection and use*, P. H. Stahl, P. G. Vermuth, IUPAC, Wiley-VCH, 2002.

Where an acid co-former is a solid at r.t. and there is no or only partial proton transfer between the compound of Formula (I) or (II) and such an acid co-former, a co-crystal of the co-former and compound of Formula (I) or (II) may result rather than a salt. All such co-crystal forms of the compound of Formula (I) or (II) are encompassed herein.

It is also to be understood that certain compounds of Formula (I) or (II) may exist in solvated form, e.g. hydrates, including solvates of a pharmaceutically acceptable salt of a compound of Formula (I) or (II).

In a further embodiment, certain compounds of Formula (I) or (II) may exist as racemates and racemic mixtures, single enantiomers, individual diastereomers and diastereomeric mixtures. Certain compounds of Formula (I) or (II) may also contain linkages (e.g. carbon-carbon bonds, carbon-nitrogen bonds such as amide bonds) wherein bond rotation is restricted about that particular linkage, e.g. restriction resulting from the presence of a ring bond or double bond. Stereoisomers may be separated using conventional techniques, e.g. chromatography or fractional crystallization, or the stereoisomers may be made by stereoselective synthesis.

In a further embodiment, the compounds of Formula (I) or (II) encompass any isotopically-labelled (or "radio-labelled") derivatives of a compound of Formula (I) or (II). Such a derivative is a derivative of a compound of Formula (I) or (II) wherein one or more atoms are replaced by an atom having an atomic mass or mass number different from the atomic mass or mass number typically found in nature. Examples of isotopes that may be incorporated include $^2H$ (also written as "D" for deuterium).

In a further embodiment, the compounds of Formula (I) or (II) may be administered in the form of a prodrug which is broken down in the human or animal body to give a compound of the Formula (I) or (II).

Various forms of prodrugs are known in the art. For examples of prodrug derivatives, see: *Nature Reviews Drug Discovery* 2008, 7, 255 and references cited therein. Intermediate compounds may also exist in enantiomeric forms and may be used as purified enantiomers, diastereomers, racemates or mixtures.

EXAMPLES

The following examples are non-limiting examples.

General Conditions (i) operations were carried out at room temperature (rt), i.e. in the range 17 to 25° C. and under an atmosphere of an inert gas such as $N_2$ unless otherwise stated;

(ii) where reactions refer to being degassed or purged, this can be performed for example by purging the reaction solvent with a constant flow of nitrogen for a suitable period of time (for example 5 to 10 min) or by repeatedly evacuating the vessel and backfill with appropriate inert atmosphere (for example nitrogen (g) or argon (g));

(iii) where reactions refer to the use of a microwave reactor, one of the following microwave reactors were used: Biotage Initiator, Personal Chemistry Emrys Optimizer, Personal Chemistry Smith Creator or CEM Explorer;

(iv) in general, the course of reactions was followed by thin layer chromatography (TLC) and/or analytical high performance liquid chromatography (HPLC or UPLC) which was usually coupled to a mass spectrometer (LCMS);

(v) when necessary, organic solutions were dried over anhydrous $MgSO_4$ or $Na_2SO_4$, or by using ISOLUTE® Phase Separator, and work-up procedures were carried out using traditional phase separating techniques;

(vi) It is understood that washing solutions used in the work-up procedures or reagent used for acidifying such as e.g. Brine, $NaHCO_3$, $NH_4Cl$, HCl, $NaH_2PO_4$ are presumed to be aqueous solutions unless otherwise stated;

(vii), evaporations were carried out either by rotary evaporation in vacuo or in a Genevac HT-4/EZ-2 or Biotage V10;

(viii) unless otherwise stated, flash column chromatography was performed on straight phase silica, using either Merck Silica Gel (Art. 9385) or prep-packed cartridges such as Biotage® SNAP cartridges (40-63 μm silica, 4-330 g), Biotage® Sfar Silica HC D cartridges (20 μm, 10-100 g), Interchim puriFlash™ cartridges (25 μm, 4-120 g), Interchim puriFlash™ cartridges (50 μm, 25-330 g), Grace™ GraceResolv™ Silica Flash Cartridges (4-120 g) or Agela Flash Colum Silica-CS cartridges (80-330 g), or on reversed phase silica using Agela Technologies C-18, spherical cartridges (20-35 μm, 100A, 80-330 g), manually or automated using a Grace Reveleris® X2 Flash system or similar system;

(ix) preparative reverse phase HPLC and preparative reverse phase SFC were performed using standard HPLC and SFC instruments, respectively, equipped with either a MS and/or UV triggered fraction collecting instrument, using either isocratic or a gradient of the mobile phase as described in the experimental section, and one of the following methods as described below;

HPLC Prep Methods:

PrepMethod A: The compound was purified by preparative HPLC on a Kromasil C8 column (10 μm, 250×20 mm ID) using a gradient of MeCN in $H_2O$/MeCN/FA (95/5/0.2) as mobile phase.

PrepMethod B: The compound was purified by preparative HPLC on a Waters™ Sunfire™ C18 OBD column (5 m, 150×30 mm ID) using a gradient of MeCN in $H_2O$/FA (0.1 M) as mobile phase.

PrepMethod C: The compound was purified by preparative HPLC on a XSelect CSH OBD column (5 μm, 150×30 mm ID) using a gradient of MeCN in $H_2O$/TFA (0.05%) as mobile phase.

PrepMethod D: The compound was purified by preparative SFC on a Waters™ BEH, (5 m, 250×30 mm ID) using (MeOH:$H_2O$ 97:3, 20 mM $NH_3$) in $CO_2$ as mobile phase.

PrepMethod E: The compound was purified by preparative HPLC on a SunFire column (5 μm, 100×19 mm ID) using a gradient of MeCN in $H_2O$ as mobile phase.

PrepMethod F: The compound was purified by preparative HPLC on a YMC Triart C18 column (5 μm, 100×20 mm ID) using a gradient of MeCN in $H_2O$ as mobile phase.

PrepMethod G: The compound was purified by preparative HPLC on a Waters™ Sunfire™ C18 OBD column (5 m, 100×19 mm ID) using a gradient of MeCN in $H_2O$ as mobile phase.

PrepMethod H: The compound was purified by preparative HPLC on a XSelect CSH OBD column (5 μm, 150×30 mm ID) using a gradient of MeCN in $H_2O$/FA (0.1%) as mobile phase.

PrepMethod I: The compound was purified by preparative HPLC on an Xbridge Prep OBD C18 column (5 μm, 150×30 mm ID) using a gradient of MeCN in a $H_2O$/$NH_4HCO_3$ (10 mM)/$NH_3$ (0.1%, aq) buffer system as mobile phase.

PrepMethod J: The compound was purified by preparative HPLC on a YMC Triart C18 column (5 μm, 100×20 mm ID) using a gradient of $H_2O$/MeCN/0.1% $NH_4OH$ as mobile phase.

PrepMethod K: The compound was purified by preparative HPLC on a XBridge™ C18 column (10 m, 250×19 mm ID) using a gradient of MeCN in $H_2O$/MeCN/$NH_3$ (95/5/0.2) as mobile phase.

PrepMethod L: The compound was purified by preparative HPLC on a SunFire column (5 μm, 150×30 mm ID) using a gradient of MeCN in 0.15 M TFA (aq) at pH3 as mobile phase.

PrepMethod M: The compound was purified by preparative HPLC on a SunFire C18 ODB column (5 μm, 150×30 mm ID) using a gradient of MeCN in FA (aq) at pH3 as mobile phase.

PrepMethod N: The compound was purified by preparative HPLC on a SunFire column (5 μm, 100×19 mm ID) using a gradient of MeCN in $H_2O$ (0.1% FA) (aq) as mobile phase.

Relevant fractions were collected, combined and freeze-dried to give the purified compound or relevant fractions were collected, combined and concentrated at reduced pressure, extracted with DCM or EtOAc, and the organic phase was dried either over $Na_2SO_4$ or by using a phase-separator, and then concentrated at reduced pressure to give the purified compound.

(x) chiral preparative chromatography was carried out using HPLC or SFC on a standard HPLC or SFC instruments, respectively, and using either isocratic or gradient run with mobile phase as described in the experimental section;

(xi) yields, where present, are not necessarily the maximum attainable, and when necessary, reactions were repeated if a larger amount of the reaction product was required;

(xii) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xiii) in general, the structures of the end-products of the Formula (I) were confirmed by nuclear magnetic resonance (NMR) and/or mass spectral techniques; proton NMR chemical shift values were measured on the delta scale using Bruker Avance III 300, 400, 500 and 600 spectrometers, operating at $^1H$ frequencies of 300, 400, 500 and 600 MHz, respectively. The experiments were typically recorded at 25° C. Chemical shifts are given in ppm with the solvent as internal standard. Protons on heteroatoms such as NH and OH protons are only reported when detected in NMR and can therefore be missing. In certain instances, protons can be masked or partially masked by solvent peaks and will therefore either be missing and not reported or reported as multiplets overlapping with solvent. The following abbreviations have been used (and derivatives thereof, e.g. dd, doublet of doublets, ddd, doublet of doublet of doublets, dt, doublet of triplets, dq, doublet of quartet etc.): s, singlet; d, doublet; t, triplet; q, quartet; m, multiplet; br, broad; qn, quintet; p, pentet; brs, broad singlet. It is understood, where the NMR spectra contains residual impurities and/or residual solvent(s), this is not reported unless it coincides or partially coincides with peaks of Intermediates and/or structures of Formula (I), in which case they are reported as multiplets, partially overlapping with said solvent or impurity. In some cases, the structures of the end-products of the Formula (I) might appear as rotamers in the NMR-spectrum, in which instances only peaks of the major rotamer are reported. In some cases, the structures of the end-products of Formula (I) might appear as rotamers in more equal portions, in such instances the peaks of such rotamers are either reported as multiplets, if the signals of said rotamers are partially overlapping, or as individual peaks, if the signals of said rotamers are well separated. Electrospray mass spectral data were obtained using a Waters Acquity UPLC coupled to a Waters single quadrupole mass spectrometer or similar equipment, acquiring both positive and negative ion data, and generally, only ions relating to the parent structure are reported; high resolution electrospray mass spectral data were obtained using a Waters XEVO qToF mass spectrometer or similar equipment, coupled to a Waters Acquity UPLC, acquiring either positive and negative ion data, and generally, only ions relating to the parent structure are reported;

(xiv) intermediates were not necessarily fully purified but their structures and purity were assessed by TLC, analytical HPLC/UPLC, and/or NMR analysis and/or mass spectrometry;

(xv) unless stated otherwise compounds containing an asymmetric carbon and/or sulfur atom were not resolved;

(xvi) in general Examples and Intermediate compounds are named using ChemDraw Professional version 20.0.2.51 or version 21.0.0 from PerkinElmer. ChemDraw Professional version 20.0.2.51 or version 21.0.0 generates the names of chemical structures using the Cahn-Ingold-Prelog (CIP) rules for stereochemistry and follows IUPAC rules as closely as possible when generating chemical names. Stereoisomers are differentiated from each other by stereodescriptors cited in names and assigned in accordance with the CIP rules.

ChemDraw is optionally using labels in the graphical representation of stereocenters such as '&' and 'or' to describe the configuration of the stereochemical centers present in the structure.

In general chemical structures of Examples and Intermediates containing the label '&' at a stereocenter, means the configuration of such Example or Intermediate at that stereocenter is a mixture of both (R) and (S); and a label 'or' means the configuration of such Example or Intermediate at that stereocenter is either (S) or (R). Absolute, unspecified, '&', and 'or' stereocenters can all be present in a single structure.

In general for structures of Examples and Intermediates where all of the stereocenters are designated as '&', the structure is named with a "rac-" prefix. For structures of Examples and Intermediates where all of the stereocenters are designated as 'or', the structure is named with a "rel-" prefix.

In general Examples and Intermediate compounds are named using the descriptors (RS) and (SR) to denote general '&' centers for chemical structures with multiple chiral centers where only some are designated as '&'. The descriptors (R*) and (S*) are used to denote the general 'or' centers for chemical structures with multiple chiral centers where only some are designated as 'or'.

In general Examples and Intermediate compounds containing stereocenters having a relationship that is either cis or trans, are named using the descriptors (RS, SR) or (RS, RS), to denote chemical structures with multiple chiral centers where only some are designated as '&'. In general, for structures of Examples and Intermediates where all stereocenters present are racemic, no flag is designated to the stereocenter(s) and the structure is drawn with straight bond(s) at each stereocenter.

In general, for structures of Examples and Intermediates where two or more stereocenters are present in a ring and fixed to each other and do not vary independently of each other, e.g. are cis or trans to each other, said stereocenters are drawn with stereobonds representing their internal relationship. Said stereocenters are labelled with an "&1" flag representing a mixture of cis-configuration or a mixture of trans-configuration, or an "or1" flag representing a single cis-isomer or a single trans-isomer with unknown absolute stereochemistry. In general, should the structure of said Example or Intermediate further contain one or more stereocenters that are racemic and not fixed in relation to the former stereocenters, said stereocenter(s) is drawn with straight bond(s) at said stereocenters.

In general the descriptors (r) and (s) are used to describe the absolute configuration of any pseudoasymmetric centers in the structures of Examples and Intermediates.

In general the label "Isomer 1" corresponds to the first eluted isomer, and "Isomer 2" corresponds to the second eluted isomer, on a given chiral HPLC column and eluent, and are used to distinguish two isomers containing one or more stereocenters with absolute unknown configuration;

(xvii) in addition to the ones mentioned above, the following abbreviations and units have been used:

Abbreviations

AcOH acetic acid
aq aqueous
$BF_3 \cdot OEt_2$ boron trifluoride diethyl etherate
calcd calculated
DCM dichloromethane
DEA diethyl amine
DIPEA N,N-diisopropylethylamine
DMAP 4-dimethylaminopyridine
DMF N,N-dimethylformamide
DMSO dimethyl sulfoxide
dppp 1,3-bis(diphenylphosphaneyl)propane
EC50 half maximal effective concentration
ESI electrospray ionization
EtOAc ethyl acetate
EtOH ethanol
$Et_2O$ diethyl ether
FA formic acid
g gram
(g) gas
HPLC high performance liquid chromatography
HRMS high resolution mass spectrometry
IC50 half maximal inhibitory concentration
ID inner diameter
IPA 2-methylpropan-2-ol
(l) liquid
LCMS liquid chromatography mass spectrometry
MeCN acetonitrile
MeOH methanol
MS mass spectrometry
MTBE 2-methoxy-2-methylpropane
NMR nuclear magnetic resonance
$Pd_2(dba)_3$ Tris(dibenzylideneacetone)dipalladium(O)
$Pd(dppf)Cl_2$ [1,1'-Bis(diphenylphosphino)ferrocene]dichloropalladium(II)
pTsOH para-toluenesulfonic acid
Rochelle salt potassium sodium tartrate
rt room temperature
RuPhos dicyclohexyl(2',6'-diisopropoxy-[1,1'-biphenyl]-2-yl)phosphane
(s) solid
sat saturated
SFC supercritical fluid chromatography
TFA trifluoroacetic acid
THE tetrahydrofuran
TLC thin layer chromatography
UPLC ultra performance liquid chromatography
UV ultraviolet
XantPhos (9,9-Dimethyl-9H-xanthene-4,5-diyl)bis(diphenylphosphane)

Units atm atmosphere
C Celcius
g gram
h hour(s)
L liter
M mole per liter
mg milligram
MHz megaherz
min minute(s)
mL milliliter
mm millimeter
mM millimole per liter
mmol millimole(s)
mol mole
μCi microcurie
μL microliter
μm micrometer
μM micromole per liter
nL nanoliter
N equivalents per liter
nm nanometer
nM nanomole per liter
pM picomole per liter
ppm parts per million
W/v weight by volume Intermediates Intermediate 1

Di-tert-butyl 5,8-dioxo-4,7-diazaspiro[2.5]octane-4,7-dicarboxylate

DMAP (16 g, 130.97 mmol) was added to a solution of 4,7-diazaspiro[2.5]octane-5,8-dione (185 g, 1.32 mol) in DCM (2.5 L). Di-tert-butyl dicarbonate (576 g, 2.64 mol) was added in several batches, and the resulting solution was stirred at rt for 2 h. The reaction was quenched by the addition of sat $NH_4Cl$ (2.0 mL). The organic layer was combined and washed with brine (1.0 mL). The organic layer was dried over anhydrous $Na_2SO_4$, and concentrated under vacuum. The residue was purified by silica gel column chromatography (EtOAc:petroleum ether, 1:6) to give the title compound (380 g, 85%) as a white solid.

Intermediate 2

Di-tert-butyl 5,8-dihydroxy-4,7-diazaspiro[2.5]octane-4,7-dicarboxylate

A solution of diisobutylaluminium hydride in toluene (1 N, 1.47 L, 103.36 mmol) was added dropwise with stirring at −78° C. to a solution of 4,7-di-tert-butyl 5,8-dioxo-4,7-diazaspiro[2.5]octane-4,7-dicarboxylate Intermediate 1 (125 g, 367.25 mmol) in THE (1.5 L), and the reaction mixture was stirred at −78° C. for 2 h. The reaction was quenched by the addition of Rochelle salt (2 N, 1.5 L). The mixture was diluted with of DCM (2 L), and the solids were filtered out. The filtrate was dried over anhydrous $Na_2SO_4$ and concentrated under vacuum. The residue was purified by silica gel column chromatography (DCM:MeOH, 50:1) to give the title compound (340 g, 90%) as a light yellow semi-solid; MS (ESI) m/z $[M+H]^+$ 345.

Intermediate 3

Di-tert-butyl (1R,6S)-2,5-diazabicyclo[4.2.0]octane-2,5-dicarboxylate $BF_3 \cdot OEt_2$ (124 g, 873.68 mmol) and triethylsilane (101 g, 868.62 mmol) was added in several batches, at −78° C., to a solution of 4,7-di-tert-butyl 5,8-dihydroxy-4,7-diazaspiro[2.5]octane-4,7-dicarboxylate Intermediate 2 (75 g, 217.77 mmol) in DCM (750 mL). The resulting solution was stirred at −78° C. for 2 h. Another batch was prepared as described above. The reaction was then quenched by the addition of water/ice (500 mL). The resulting solution was extracted with DCM (2×500 mL) and the combined organic layer was dried over anhydrous $Na_2SO_4$ and concentrated under vacuum. The residue was purified by silica gel column chromatography (EtOAc:hexane, 1:20-1:10), to give the title compound (75 g, 55%) as an off-white solid; $^1H$ NMR ($CDCl_3$) δ 4.3 (s, 1H), 3.4 (m, 2H), 2.1 (s, 2H), 1.47 (s, 9H).

Intermediate 4 rac-tert-Butyl (1R,6S)-2,5-diazabicyclo[4.2.0]octane-2-carboxylate pTsOH (22 g, 127.76 mmol) was added to a solution of di-tert-butyl (1R,6S)-2,5-diazabicyclo[4.2.0]octane-2,5-dicarboxylate Intermediate 3 (40 g, 128.04 mmol) in THE (400 mL). The resulting solution was stirred at 60° C. for 3 h. Three more batches were prepared as described above. The reaction mixture was cooled to rt, and the solids were filtered out. $K_2CO_3$ (320 g) was added with stirring to the resulting solution and stirred at rt for 1 h. The solids were filtered out. The resulting mixture was concentrated under vacuum. The residue was purified by silica gel column chromatography (DCM:MeOH, 1:0-10:1) to give the title compound (45 g, 41%) as yellow oil; MS (ESI) m/z $[M+H]^+$ 213.

Intermediate 5

Methyl 3-(((1-methyl-1H-pyrazol-3-yl)methyl)amino)-4-nitrobenzoate $K_2CO_3$ (5.21 g, 37.66 mmol) was added to a solution of (1-methyl-1H-pyrazol-3-yl)methanamine (1.26 g, 11.30 mmol) and methyl 3-fluoro-4-nitrobenzoate (1.5 g, 7.53 mmol) in MeCN (20 mL) under an atmosphere of $N_2$(g), and the reaction mixture was stirred at 20° C. for 2 h. The reaction was quenched with sat brine (aq, 200 mL) and extracted with EtOAc (3×250 mL). The combined organic layer was dried over $Na_2SO_4$, filtered and evaporated at reduced pressure. The crude product was purified by straight phase flash chromatography on silica (gradient: 0-100% EtOAc in petroleum ether) to give the title compound (1.80 g, 82%) as a yellow solid; MS (ESI) m/z $[M+H]^+$ 291.

Intermediate 6

Methyl 4-amino-3-(((1-methyl-1H-pyrazol-3-yl)methyl)amino)benzoate

A suspension of methyl 3-(((1-methyl-1H-pyrazol-3-yl)methyl)amino)-4-nitrobenzoate Intermediate 5 (900 mg, 3.10 mmol) and 10% Pd—C (99 mg, 0.09 mmol) in THE (20 mL) was stirred under an atmosphere of $H_2$(g) at 20° C. for 2 h. The reaction mixture was filtered through celite and the filter cake was washed with EtOAc (200 mL). The filtrate was concentrated under reduced pressure, and the residue was purified by preparative TLC (EtOAc:petroleum ether, 2:1) to give the title compound (0.80 g, 99%) as a colourless gum; MS (ESI) m/z $[M+H]^+$ 261.

Intermediate 7

Methyl 2-(chloromethyl)-1-((1-methyl-1H-pyrazol-3-yl)methyl)-1H-benzo[d]imidazole-6-carboxylate Methyl 4-amino-3-(((1-methyl-1H-pyrazol-3-yl)methyl)amino)benzoate Intermediate 6 (500 mg, 1.92 mmol) was added to a solution of 2-chloro-1,1,1-trimethoxyethane (356 mg, 2.31 mmol) and pTsOH (66 mg, 0.38 mmol) in MeCN (10 mL) and the reaction mixture was stirred at 20° C. for 2 h. The reaction mixture was quenched with sat brine (aq, 100 mL) and extracted with EtOAc (3×150 mL). The combined organic layer was dried over $Na_2SO_4$, filtered and evaporated. The residue was purified by preparative TLC (DCM:MeOH, 30:1), to give the title compound (0.410 g, 67%) as an orange solid; MS (ESI) m/z $[M+H]^+$ 319.

Intermediate 8 rac-tert-Butyl (1R,6S)-5-(6-((4-cyano-2-fluorobenzyl)oxy)pyridin-2-yl)-2,5-diazabicyclo[4.2.0]octane-2-carboxylate rac-tert-Butyl (1R,6S)-2,5-diazabicyclo[4.2.0]octane-2-carboxylate Intermediate 4 (800 mg, 3.77 mmol) was added to a suspension of 4-(((6-bromopyridin-2-yl)oxy)methyl)-3-fluorobenzonitrile (WO2021081207) (1.389 g, 4.52 mmol), dppp (311 mg, 0.75 mmol), sodium 2-methylpropan-2-olate (905 mg, 9.42 mmol) and $Pd_2(dba)_3$ (345 mg, 0.38 mmol) in toluene (20 mL) under an atmosphere of $N_2$(g), and the reaction mixture was stirred at 100° C. for 2 h. The reaction mixture was quenched with water (100 mL), and extracted with EtOAc (3×100 mL). The combined organic layer was dried over $Na_2SO_4$, filtered and evaporated and the crude product was purified by straight phase flash column chromatography on silica (gradient: 0-50% EtOAc in petroleum ether) to give the title compound (1.40 g, 85%) as a yellow gum; MS (ESI) m/z $[M+H]^+$ 439.

Intermediate 9 rac-4-(((6-((1R,6S)-2,5-Diazabicyclo[4.2.0]octan-2-yl)pyridin-2-yl)oxy)methyl)-3-fluorobenzonitrile rac-tert-Butyl (1R,6S)-5-(6-((4-cyano-2-fluorobenzyl)oxy)pyridin-2-yl)-2,5-diazabicyclo[4.2.0]octane-2-carboxylate Intermediate 8 (1.5 g, 3.42 mmol) was dissolved in HCl in dioxane (4 M, 5 mL), and the reaction mixture was stirred at 25° C. for 2 h. The reaction mixture was concentrated under reduced pressure to give the title compound (1.5 g, 98%) as a pink solid; MS (ESI) m/z $[M+H]^+$ 339.

Intermediate 10 rac-Methyl 2-(((1R,6S)-5-(6-((4-cyano-2-fluorobenzyl)oxy)pyridin-2-yl)-2,5-diazabicyclo[4.2.0]octan-2-yl)methyl)-1-((1-methyl-1H-pyrazol-3-yl)methyl)-1H-benzo[d]imidazole-6-carboxylate rac-4-(((6-((1R,6S)-2,5-Diazabicyclo[4.2.0]octan-2-yl)pyridin-2-yl)oxy)methyl)-3-fluorobenzonitrile Intermediate 9 (80 mg, 0.24 mmol) was added to a solution of methyl 2-(chloromethyl)-1-((1-methyl-1H-pyrazol-3-yl)methyl)-1H-benzo[d]imidazole-6-carboxylate Intermediate 7 (75 mg, 0.24 mmol) and $K_2CO_3$ (131 mg, 0.95 mmol) in MeCN (3 mL) and the reaction mixture was stirred at 60° C. for 3 h. The reaction mixture was quenched with sat brine (50 mL) and extracted with EtOAc (3×100 mL). The combined organic layer was dried over $Na_2SO_4$, filtered and concentrated in vacuo. The residue was purified by preparative TLC (DCM:MeOH, 15:1), to give the title compound (0.130 g, 89%) as a yellow solid; MS (ESI) m/z $[M+H]^+$ 621.

Intermediate 11

Methyl 2-(((1RS,6SR)-5-(6-((4-cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylate Methyl (S)-2-(chloromethyl)-1-(oxetan-2-ylmethyl)-1H-benzo[d]imidazole-6-carboxylate (500 mg, 1.70 mmol) was added to a solution of $K_2CO_3$ (938 mg, 6.79 mmol) and rac-4-(((6-((1R,6S)-2,5-diazabicyclo[4.2.0]octan-2-yl)pyridin-2-yl)oxy)methyl)-3-fluorobenzonitrile Intermediate 9 (760 mg, 1.70 mmol) in MeCN (10 mL) and the reaction mixture was stirred at 80° C. for 3 h. The reaction mixture was quenched with water (100 mL) and extracted with EtOAc (3×100 mL). The combined organic layer was dried over $Na_2SO_4$, filtered and concentrated in vacuo. The residue was purified by preparative TLC (DCM:MeOH, 15:1), to give the title compound (900 mg, 89%) as a yellow gum; MS (ESI) m/z $[M+H]^+$ 597.

Intermediate 12

Methyl 2-(((1R*,6S*)-5-(6-((4-cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylate, Isomer 1

Intermediate 13

Methyl 2-(((1R*,6S*)-5-(6-((4-cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylate, Isomer 2

The diastereomers of methyl 2-(((1RS,6SR)-5-(6-((4-cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylate Intermediate 11 (420 mg, 0.70 mmol) were separated by chiral chromatography on a CHIRALPAK© IG column (5 μm, 250×20 mm ID), using an isocratic run of 30% EtOH in hexane/DCM (3:1, containing 0.5% 2 M $NH_3$ in MeOH) as eluant; the first eluted compound was collected and evaporated to give the title compound Isomer 1, Intermediate 12 (150 mg); MS (ESI) m/z $[M+H]^+$ 597; the second eluted compound was collected and evaporated to give the title compound Isomer 2, Intermediate 13 (180 mg) as a white solid; MS (ESI) m/z $[M+H]^+$ 597.

Intermediate 14

Methyl (S)-3-fluoro-4-nitro-5-((oxetan-2-ylmethyl)amino)benzoate

DIPEA (8.45 mL, 48.36 mmol) was added to a solution of methyl 3,5-difluoro-4-nitrobenzoate (3.50 g, 16.12 mmol) and (S)-oxetan-2-ylmethanamine (1.40 g, 16.12 mmol) in THF/DMF (125 mL, 5:2), and the reaction mixture was stirred at 20° C. for 4 h. The solvent was removed under reduced pressure, and the residue was suspended in water (300 mL). The aqueous layer was extracted with EtOAc (3×500 mL), and the combined organic layer was dried over $Na_2SO_4$, filtered and evaporated. The crude product was purified by straight phase flash chromatography on silica (gradient: 10-20% EtOAc in petroleum ether) to give the title compound (4.50 g, 98%) as a yellow solid; MS (ESI) m/z $[M+H]^+$ 285.0.

Intermediate 15

Methyl (S)-4-amino-3-fluoro-5-((oxetan-2-ylmethyl)amino)benzoate

A suspension of methyl (S)-3-fluoro-4-nitro-5-((oxetan-2-ylmethyl)amino)benzoate Intermediate 14 (4.2 g, 14.78 mmol) and 10% Pd—C (1.57 g, 1.48 mmol) in THE (150 mL) was stirred under an atmosphere of $H_2$ (g) at 3 atm and 25° C. for 2 h. The reaction mixture was filtered through celite and the filter cake was washed with MeOH (3×100 mL). The filtrate was concentrated under reduced pressure. The crude product was purified by straight phase flash chromatography on silica (gradient: 70-80% EtOAc in petroleum ether), to give the title compound (3.20 g, 85%) as a light red solid; MS (ESI) m/z $[M+H]^+$ 254.95.

Intermediate 16

Methyl (S)-2-(chloromethyl)-4-fluoro-1-(oxetan-2-ylmethyl)-1H-benzo[d]imidazole-6-carboxylate pTsOH (0.108 g, 0.57 mmol) was added to a solution of methyl (S)-4-amino-3-fluoro-5-((oxetan-2-ylmethyl)amino)benzoate Intermediate 15 (1.45 g, 5.70 mmol) and 2-chloro-1,1,1-trimethoxyethane (1.06 g, 6.84 mmol) in MeCN (10 mL) and the reaction mixture was stirred at rt for 18 h. The solvent was evaporated at reduced pressure and the crude compound was purified by straight phase flash chromatography on silica (gradient: 50-100% EtOAc in heptane) to give the title compound (1.54 g, 86%); MS (ESI) m/z $[M+H]^+$ 313.26.

Intermediate 17 rac-tert-Butyl (1R,6R)-5-(6-bromopyridin-2-yl)-2,5-diazabicyclo[4.2.0]octane-2-carboxylate rac-tert-Butyl (1R,6R)-2,5-diazabicyclo[4.2.0]octane-2-carboxylate (7.25 g, 34.14 mmol) and $K_2CO_3$ (10.38 g, 75.11 mmol) were added to a solution of 2-bromo-6-fluoropyridine (7.21 g, 40.97 mmol) in DMF (100 mL) at rt, and the reaction mixture was stirred at 90° C. for 24 h. After cooling to rt, water (500 mL) was added, and the mixture was extracted with EtOAc (2×300 mL). The combined organic layer was washed with brine (300 mL), dried over $Na_2SO_4$, filtered and evaporated. The crude product was purified by flash chromatography on silica (hexane:EtOAc, 1:1) to give the title compound (8.2 g, 65%); MS (ESI) m/z $[M+H]^+$ 368.0.

Intermediate 18 rac-tert-Butyl (1R,6R)-5-(6-((4-cyano-2-fluorobenzyl)oxy)pyridin-2-yl)-2,5-diazabicyclo[4.2.0]octane-2-carboxylate XantPhos (79 mg, 135.8 μmol), Palladium (II) acetate (15 mg, 68 μmol) and $Cs_2CO_3$ (885 mg, 2.72 mmol) were added to a stirred solution of rac-tert-butyl (1R,6R)-5-(6-bromopyridin-2-yl)-2,5-diazabicyclo[4.2.0]octane-2-carboxylate Intermediate 17 (500 mg, 1.36 mmol) and 3-fluoro-4-(hydroxymethyl)benzonitrile (411 mg, 2.72 mmol) in dry toluene (10 mL) under an atmosphere of Ar (g) at 15° C. The reaction mixture was degassed and backfilled with Ar (g) (×3), and then heated at 100° C. under an atmosphere of Ar (g) for 18 h. The reaction mixture was cooled to rt and DCM (20 mL) was added. The mixture was filtered and the filtrate was collected and concentrated at reduced pressure. The crude product was purified by preparative HPLC, Prep-Method E, (gradient: 60-85%) to give the title compound (100 mg, 17%); MS (ESI) m/z $[M+H]^+$ 439.2.

Intermediate 19 rac-4-(((6-((1R,6R)-2,5-Diazabicyclo[4.2.0]octan-2-yl)pyridin-2-yl)oxy)methyl)-3-fluorobenzonitrile rac-tert-Butyl (1R,6R)-5-(6-((4-cyano-2-fluorobenzyl)oxy)pyridin-2-yl)-2,5-diazabicyclo[4.2.0]octane-2-carboxylate Intermediate 18 (100 mg, 228 μmol) was dissolved in $Et_2O$ (5 mL), and a solution of HCl in $Et_2O$ (2M, 3 mL) was added. The reaction mixture was stirred at rt for 16 h. The precipitate was collected by filtration, and washed with $Et_2O$, to give the hydrochloride of the title compound (70 mg, 82%); MS (ESI) m/z $[M+H]^+$ 339.2.

Intermediate 20

Methyl 2-(((1RS,6RS)-5-(6-((4-cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylate Methyl (S)-2-(chloromethyl)-4-fluoro-1-(oxetan-2-ylmethyl)-1H-benzo[d]imidazole-6-carboxylate Intermediate 16 (375 mg, 1.2 mmol) and DIPEA (760 mg, 6.0 mmol) were added to a solution of rac-4-(((6-((1R,6R)-2,5-diazabicyclo[4.2.0]octan-2-yl)pyridin-2-yl)oxy)methyl)-3-fluorobenzonitrile hydrochloride Intermediate 19 (450 mg, 1.2 mmol) in MeCN (7 mL) at rt, and the reaction mixture was stirred at rt for 14 h. The solvent was evaporated, and the residue was dissolved in DMSO, and purified by preparative HPLC, PrepMethod E, (gradient 50-70%), to give the title compound (231 mg, 31%); MS (ESI) m/z $[M+H]^+$ 615.2.

Intermediate 21

Methyl 2-(((1R*,6R*)-5-(6-((4-cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylate, Isomer 1

Intermediate 22

Methyl 2-(((1R*,6R*)-5-(6-((4-cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylate, Isomer 2

The stereoisomers of methyl 2-(((1RS,6RS)-5-(6-((4-cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylate Intermediate 20 were separated by chiral chromatography on a Chiralpack IJ column (5 μm, 250×21 mm ID), using an isocratic run, eluted with 80% MeOH in $CO_2$, and with a flow rate of 50 mL/min;

the first eluted compound was collected and evaporated to give the title compound Isomer 1, Intermediate 21 (72 mg); MS (ESI) m/z $[M+H]^+$ 615.2; and the second eluted compound was collected and evaporated to give the title compound Isomer 2, Intermediate 22 (63 mg); MS (ESI) m/z $[M+H]^+$ 615.2.

Intermediate 23

Methyl (S)-3-methoxy-4-nitro-5-((oxetan-2-ylmethyl)amino)benzoate $K_2CO_3$ (5.43 g, 39.27 mmol) was added to a solution of methyl 3-fluoro-5-methoxy-4-nitrobenzoate (3 g, 13.09 mmol) and (S)-oxetan-2-ylmethanamine (1.14 g, 13.09 mmol) in THF/DMF (5:2, 110 mL) and the reaction mixture was stirred at 90° C. for 16 h. The solvent was removed under reduced pressure, and the residue was suspended in water (250 mL). The aqueous layer was extracted with EtOAc (3×250 mL), and the combined organic layer was dried over $Na_2SO_4$, filtered and concentrated at reduced pressure. The crude product was purified by straight phase flash column chromatography on silica (10-20% EtOAc in petroleum ether) to give the title compound (1.8 g, 46%) as a yellow solid; MS (ESI) m/z $[M+H]^+$ 297.1.

Intermediate 24

Methyl (S)-4-amino-3-methoxy-5-((oxetan-2-ylmethyl)amino)benzoate

A suspension of Pd—C (0.144 g, 1.35 mmol) and methyl (S)-3-methoxy-4-nitro-5-((oxetan-2-ylmethyl)amino)benzoate Intermediate 23 (4 g, 13.50 mmol) in THE (100 mL) was stirred under an atmosphere of $H_2$(g) at 2 atm and 15° C. for 3 h. The reaction mixture was filtered through celite and the filter cake was washed with MeOH (3×300 mL). The filtrate was concentrated under reduced pressure. The crude product was purified by straight phase flash column chromatography on silica (50-70% EtOAc in petroleum ether) to give the title compound (3.00 g, 83%) as a light yellow solid; MS (ESI) m/z $[M+H]^+$ 267.3.

Intermediate 25

Methyl (S)-2-(chloromethyl)-4-methoxy-1-(oxetan-2-ylmethyl)-1H-benzo[d]imidazole-6-carboxylate pTsOH (0.119 g, 0.63 mmol) was added to a solution of methyl (S)-4-amino-3-methoxy-5-((oxetan-2-ylmethyl)amino)benzoate Intermediate 24 (0.333 g, 1.25 mmol) and 2-chloro-1,1,1-trimethoxyethane (0.387 g, 2.50 mmol) in MeCN (10 mL) and the reaction mixture was stirred at 45° C. for 30 min. The reaction mixture was concentrated under reduced pressure and the residue was purified by straight phase flash column chromatography on silica (50-100% EtOAc in heptane) to give the title compound (0.155 g, 38%); MS (ESI) m/z $[M+H]^+$ 325.0.

Intermediate 26

Methyl 2-(((1RS,6RS)-5-(6-((4-cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylate Methyl (S)-2-(chloromethyl)-4-methoxy-1-(oxetan-2-ylmethyl)-1H-benzo[d]imidazole-6-carboxylate Intermediate 25 (119 mg, 0.36 mmol) and DIPEA (238 mg, 1.8 mmol) were added to a solution of rac-4-(((6-((1R,6R)-2,5-diazabicyclo[4.2.0]octan-2-yl)pyridin-2-yl)oxy)methyl)-3-fluorobenzonitrile hydrochloride Intermediate 19 (151 mg, 0.36 mmol) in MeCN (5 mL) and the reaction mixture was stirred at rt for 14 h. The solvent was evaporated, and the crude product was purified by preparative HPLC, PrepMethod E, (gradient: 50-70%) to give the title compound (159 mg, 71%); MS (ESI) m/z $[M+H]^+$ 627.2.

Intermediate 27

Methyl 2-(((1R*,6R*)-5-(6-((4-cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylate, Isomer 1

Intermediate 28

Methyl 2-(((1R*,6R*)-5-(6-((4-cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylate, Isomer 2

The stereoisomers of methyl 2-(((1RS,6RS)-5-(6-((4-cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylate Intermediate 26 were separated by chiral chromatography on a Chiralpak IA column (5 μm, 250×20 mm) eluted with IPA/MeOH (50:50), and at a flow rate of 10 mL/min;

the first eluted compound was collected and evaporated to give the title compound Isomer 1, Intermediate 27 (74 mg); MS (ESI) m/z $[M+H]^+$ 627.2; and the second eluted compound was collected and evaporated to give the title compound Isomer 2; Intermediate 28 (64 mg); MS (ESI) m/z $[M+H]^+$ 627.2.

Intermediates 29 to 35

The following Intermediates 29 to 35 were prepared as described in General Synthesis Scheme 1 and General Preparation Method A, B or C or as described in General Synthesis Scheme 2 and General Preparation Method D from appropriate Intermediates (SM 1 and SM 2) as described below in Table 4.

General Synthesis Scheme 1

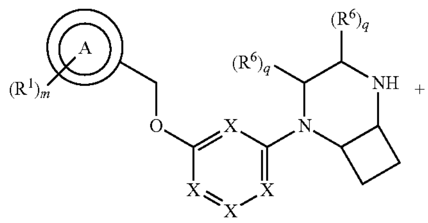

SM 1

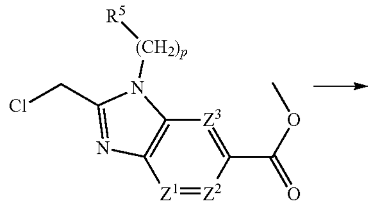

SM 2

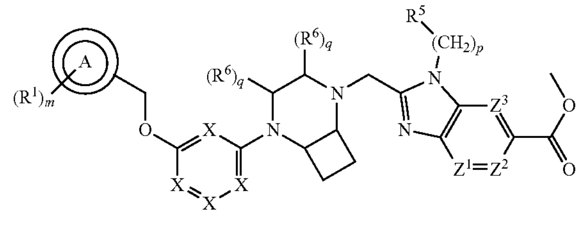

Preparation Method A: DIPEA (4 eq) was added to a solution of SM 1 (1 eq) and SM 2 (1 eq) in MeCN (0.1-0.2 M), and the reaction mixture was stirred at rt for 14 h. The reaction mixture was optionally concentrated at reduced pressure and used as crude in the next step or worked up by extractive purification using water and EtOAc, and the crude product purified by preparative HPLC, Prepmethod E (59% MeCN in $H_2O$).

Preparation Method B: DIPEA (4 eq) and a catalytic amount of NaI was added to a solution of SM 1 (1 eq) and SM 2 (1 eq) in MeCN (0.1-0.2 M), and the reaction mixture was stirred at rt-40° C. for 16 h. The reaction mixture was optionally concentrated at reduced pressure and worked up by extractive purification using water and EtOAc, and the crude product was purified by preparative HPLC, PrepMethod E (40-65% MeCN in $H_2O$).

Preparation Method C: $K_2CO_3$ (3-6 eq) was added to a solution of SM 1 (1 eq) and SM 2 (1 eq) in MeCN (0.1-0.2 M), and the reaction mixture was heated at 60-80° C. for 2-3 h. The reaction mixture was optionally concentrated at reduced pressure and worked up by extractive purification using water and EtOAc, and the crude product was purified by preparative TLC using either petroleum ether:EtOAc (1:3 or 1:1) or DCM:MeOH (15:1) as eluant.

General Synthesis Scheme 2

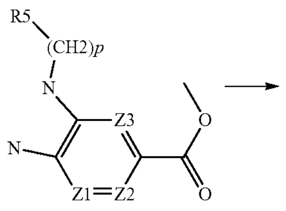

SM 2

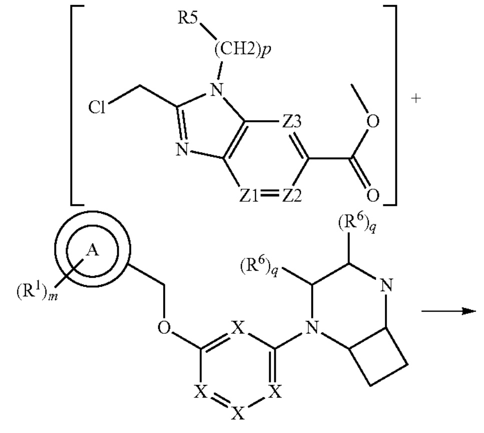

SM 1

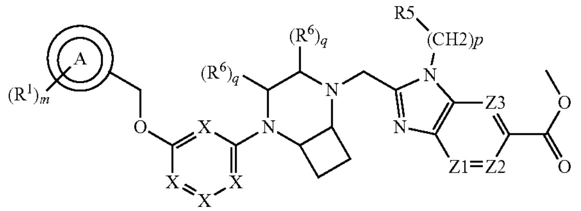

Preparation Method D: 2-Chloro-1,1,1-trimethoxyethane (1.1 eq) and pTsOH (0.1 eq) was added to a solution of SM 2 (1 eq) in MeCN (0.1 M) and the reaction mixture was stirred at rt for 3 h. $K_2CO_3$ (4 eq), SM 1 (1 eq) and MeCN (0.1 M) was added to the reaction mixture and the mixture was stirred at 80° C. for 3 h. Water was added and the reaction mixture was extracted with EtOAc. The organic layer was dried over $Na_2SO_4$, filtered and concentrated at reduced pressure and the crude product was purified by flash chromatography on a C18 column (20-100% MeCN in $H_2O$).

TABLE 4

| Intermediates 29 to 35 | | | | | |
|---|---|---|---|---|---|
| Intermediate No | Name | MS (ESI) m/z [M + H]$^+$ | SM 1 Intermediate No | SM 2 Intermediate No | Method |
| 29 | Methyl 2-(((1RS,6RS)-5-(6-((4-cyano-2-fluorobenzyl)oxy)pyridin-2-yl)-2,5-diazabicyclo[4.2.0]octan-2-yl)methyl)-5-fluoro-1-(((S)-oxetan-2-yl)methyl)-1H-benzo[d]imidazole-6-carboxylate | 615.4 | 19 | 67 | A |
| 30 | rac-Methyl 4-chloro-2-(((1R,6S)-5-(6-((4-cyano-2-fluorobenzyl)oxy)pyridin-2-yl)-2,5-diazabicyclo[4.2.0]octan-2-yl)methyl)-1-(oxetan-2-ylmethyl)-1H-benzo[d]imidazole-6-carboxylate | 631 | 9 | 71 | C |
| 31 | rac-Methyl 5-chloro-2-(((1R,6S)-5-(6-((4-cyano-2-fluorobenzyl)oxy)pyridin-2-yl)-2,5-diazabicyclo[4.2.0]octan-2-yl)methyl)-1-(oxetan-2-ylmethyl)-1H-benzo[d]imidazole-6-carboxylate | 631 | 9 | 78 | D |
| 32 | rac-Methyl 7-chloro-2-(((1R,6S)-5-(6-((4-cyano-2-fluorobenzyl)oxy)pyridin-2-yl)-2,5-diazabicyclo[4.2.0]octan-2-yl)methyl)-1-(oxetan-2-ylmethyl)-1H-benzo[d]imidazole-6-carboxylate | 631 | 9 | 75 | C |
| 33 | Methyl 2-(((1RS,6RS)-5-(6-((4-chloro-2-fluorobenzyl)oxy)pyridin-2-yl)-2,5-diazabicyclo[4.2.0]octan-2-yl)methyl)-4-methoxy-1-(((S)-oxetan-2-yl)methyl)-1/-benzo[d]imidazole-6-carboxylate | 636.0 | 55 | 25 | B |
| 34 | rac-Methyl 1-(2-(tert-butoxy)ethyl)-2-(((1R,6S)-5-(6-((4-cyano-2-fluorobenzyl)oxy)pyridin-2-yl)-2,5-diazabicyclo[4.2.0]octan-2-yl)methyl)-1H-benzo[d]imidazole-6-carboxylate | 627 | 9 | 76 | C |
| 35 | rac-Methyl 1-(2-butoxyethyl)-2-(((1R,6S)-5-(6-((4-cyano-2-fluorobenzyl)oxy)pyridin-2-yl)-2,5-diazabicyclo[4.2.0]octan-2-yl)methyl)-1H-benzo[d]imidazole-6-carboxylate | 627.3 | 9 | 77 | A |

Intermediate 36

Methyl 2-(((1R*,6R*)-5-(6-((4-cyano-2-fluorobenzyl)oxy)pyridin-2-yl)-2,5-diazabicyclo[4.2.0]octan-2-yl)methyl)-5-fluoro-1-(((S)-oxetan-2-yl)methyl)-1H-benzo[d]imidazole-6-carboxylate, Isomer 1

Intermediate 37

Methyl 2-(((1R*,6R*)-5-(6-((4-cyano-2-fluorobenzyl)oxy)pyridin-2-yl)-2,5-diazabicyclo[4.2.0]octan-2-yl)methyl)-5-fluoro-1-(((S)-oxetan-2-yl)methyl)-1H-benzo[d]imidazole-6-carboxylate, Isomer 2

The diastereomers of methyl 2-(((1RS,6RS)-5-(6-((4-cyano-2-fluorobenzyl)oxy)pyridin-2-yl)-2,5-diazabicyclo[4.2.0]octan-2-yl)methyl)-5-fluoro-1-(((S)-oxetan-2-yl)methyl)-1H-benzo[d]imidazole-6-carboxylate Intermediate 29 were separated by chiral chromatography on a Chiralpak IA-II column (250×30 mm, 5 μm) eluted with hexane/IPA/MeOH (60/20/20), at a flow rate of 12 mL/min;

the first eluted compound was collected and evaporated to give the title compound, Isomer 1 Intermediate 36 (75 mg); MS (ESI) m/z $[M+H]^+$ 615.4; and the second eluted compound was collected and evaporated to give the title compound, Isomer 2 Intermediate 37 (63 mg); MS (ESI) m/z $[M+H]^+$ 615.4.

Intermediate 38 rel-Methyl 4-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer 1

Intermediate 39 rel-Methyl 4-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer 2

Intermediate 40 rel-Methyl 4-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer 3

Intermediate 41 rel-Methyl 4-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer 4

The stereoisomers of rac-methyl 4-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate Intermediate 30 (290 mg) were separated by chiral chromatography on a Chiralpak IG column (250×20 mm, 5 μm) eluted with 50% EtOH in hexane:DCM (3:1, containing 0.5% 2M $NH_3$ in MeOH), at a flow rate of 17 mL/min and detected at 220 nm and 254 nm;

the first eluted compound was collected and evaporated to give the title compound, Isomer 1, Intermediate 38 (57 mg, 20%); MS (ESI) m/z $[M+H]^+$ 631;

the second eluted compound was collected and evaporated to give the title compound, Isomer 2 Intermediate 39 (50 mg, 17%); MS (ESI) m/z $[M+H]^+$ 631;

the third eluted compound was collected and evaporated to give the title compound, Isomer 3 Intermediate 40 (70 mg, 24%); MS (ESI) m/z $[M+H]^+$ 631; and the fourth eluted compound was collected and evaporated to give the title compound, Isomer 4 Intermediate 41 (80 mg, 28%); MS (ESI) m/z $[M+H]^+$ 631.

Intermediate 42 rel-Methyl 5-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer 1

Intermediate 43 rel-Methyl 5-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer 2

Intermediate 44 rel-Methyl 5-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer The stereoisomers of rac-methyl 5-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate Intermediate 31 were separated by chiral chromatography on a Chiralpak IG column (250×20 mm, 5 μm), eluted with 20% EtOH in hexane:DCM (3:1, containing 0.5% 2M $NH_3$ in MeOH), at a flow rate of 20 mL/min and detected at 220 nm and 254 nm;

the first eluted compound was collected and evaporated to give the title compound, Isomer 1, Intermediate 42 (65 mg, 14%);

the second eluted compound was collected and evaporated to give the title compound, Isomer 2 Intermediate 43 (85 mg, 18%);

the fourth eluted compound was collected and evaporated to give the title compound, Isomer 4 Intermediate 44 (70 mg, 25%).

Intermediate 45 rel-Methyl 7-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer 1

Intermediate 46 rel-Methyl 7-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer 2

Intermediate 47 rel-Methyl 7-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate, Isomer 4

The stereoisomers of rac-Methyl 7-chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylate Intermediate 32 were separated by chiral chromatography on a Chiralpak IF-2 column (250×20 mm, 5 μm), eluted with 50% EtOH in hexane:DCM (3:1, containing 0.5% 2M $NH_3$ in MeOH), at a flow rate of 16 mL/min and detected at 220 nm and 254 nm;

- the first eluted compound was collected and evaporated to give the title compound, Isomer 1, Intermediate 45 (75 mg, 12%);
- the second eluted compound was collected and evaporated to give the title compound, Isomer 2 Intermediate 46 (100 mg, 17%);
- the fourth eluted compound was collected and evaporated to give the title compound, Isomer 4 Intermediate 47 (120 mg, 20%).

Intermediate 48

Methyl 2-(((1R*,6R*)-5-(6-((4-chloro-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylate, Isomer 1

Intermediate 49

Methyl 2-(((1R*,6R*)-5-(6-((4-chloro-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylate, Isomer 2

The diastereomers of methyl 2-(((1RS,6RS)-5-(6-((4-chloro-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylate Intermediate 33 were separated by chiral chromatography on a Chiralpak IA column (250×4.6 mm, 5 μm) eluted with IPA-MeOH (50/50), at a flow rate 0.6 mL/min;

- the first eluted compound was collected and evaporated to give the title compound, Isomer 1 Intermediate 48 (111 mg); MS (ESI) m/z $[M+H]^+$ 636.2; and
- the second eluted compound was collected and evaporated to give the title compound, Isomer 2 Intermediate 49 (101 mg); MS (ESI) m/z $[M+H]^+$ 636.2.

Intermediate 50

Methyl 3-(((1-ethyl-1H-imidazol-5-yl)methyl)amino)-5-methoxy-4-nitrobenzoate

A solution of methyl 3-fluoro-5-methoxy-4-nitrobenzoate (1.4 g, 6.11 mmol) in DMF (5 mL) was slowly added dropwise to a solution (1-ethyl-1H-imidazol-5-yl)methanamine dihydrochloride (1.33 g, 6.72 mmol) and DIPEA (3.95 g, 30.54 mmol) in DMF (5 mL) and the reaction mixture was heated under stirring at 60° C. for 16 h. The reaction mixture was allowed to cool to rt, diluted with water (30 mL), and the mixture was extracted with DCM (3×30 mL). The combined organic layer was washed with brine (50 mL) and water (50 mL), dried over $Na_2SO_4$, filtered, and concentrated in vacuo. The crude product was purified by flash chromatography on silica (10% EtOAc in hexane) to give the title compound (1.9 g, 93%) as yellow solid; MS (ESI) m/z $[M+H]^+$ 335.1.

Intermediate 51

Methyl 4-amino-3-(((1-ethyl-1H-imidazol-5-yl)methyl)amino)-5-methoxybenzoate

10% Pd/C (0.2 g) was added to a solution of methyl 3-(((1-ethyl-1H-imidazol-5-yl)methyl)amino)-5-methoxy-4-nitrobenzoate Intermediate 50 (1.9 g, 5.0 mmol) in MeOH (20 mL), and the reaction mixture was stirred under an atmosphere of $H_2$(g) (1 atm) at rt for 36 h. The reaction mixture was filtered through a pad of celite, the filtrate was concentrated in vacuo, and the crude product was purified by flash chromatography on silica (0-95% MeOH in MTBE) to give the title compound (1.5 g, 87%) as yellow solid; MS (ESI) m/z $[M+H]^+$ 305.2.

Intermediate 52

Methyl 1-((1-ethyl-1H-imidazol-5-yl)methyl)-2-(hydroxymethyl)-4-methoxy-1H-benzo[d]imidazole-6-carboxylate 2,2,2-Triethoxyethan-1-ol (2.63 g, 14.78 mmol) and pTsOH (424 mg, 2.46 mmol) were added to a solution of methyl 4-amino-3-(((1-ethyl-1H-imidazol-5-yl)methyl)amino)-5-methoxybenzoate Intermediate 51 (1.5 g, 4.93 mmol) in MeCN (7 mL), and the reaction mixture was heated under stirring at 60° C. for 1 h. The reaction mixture was allowed to cool to rt and concentrated in vacuo, and the residue was purified by flash chromatography on silica (0-95% MeOH in MTBE) to give the title compound (1.4 g, 75%); $^1$H NMR (400 MHz, DMSO-$d_6$) δ 7.74 (s, 1H), 7.65 (s, 1H), 7.26 (s, 1H), 6.52 (s, 1H), 5.75 (s, 1H), 5.65 (s, 2H), 4.70 (d, 2H), 3.95 (d, 5H), 3.83 (s, 3H), 1.11 (t, 3H).

Intermediate 53

Methyl 2-(chloromethyl)-1-((1-ethyl-1H-imidazol-5-yl)methyl)-4-methoxy-1H-benzo[d]imidazole-6-carboxylate A catalytic amount of DMF followed by $SOCl_2$ (2.42 g, 20.32 mmol) were added dropwise under vigorous stirring to a solution of methyl 1-((1-ethyl-1H-imidazol-5-yl)methyl)-

2-(hydroxymethyl)-4-methoxy-1H-benzo[d]imidazole-6-carboxylate Intermediate 52 (1.4 g, 4.07 mmol) in DCM (20 mL), and the reaction mixture was stirred at rt for 1 h. The reaction solution was concentrated in vacuo and the obtained solid was dried in vacuo to give the dihydrochloride salt of the title compound (1.70 g, 96%) as beige solid; MS (ESI) m/z $[M+H]^+$ 363.2.

Intermediate 54 rac-tert-Butyl (1R,6R)-5-(6-((4-chloro-2-fluorobenzyl)oxy)pyridin-2-yl)-2,5-diazabicyclo[4.2.0]octane-2-carboxylate Xantphos (817 mg, 1.41 mmol), palladium (II) acetate (159 mg, 706 μmol) and $Cs_2CO_3$ (9.2 g, 28.24 mmol) were added to a stirred solution of rac-tert-butyl (1R,6R)-5-(6-bromopyridin-2-yl)-2,5-diazabicyclo[4.2.0]octane-2-carboxylate Intermediate 17 (5.2 g, 14.12 mmol) and (4-chloro-2-fluorophenyl)methanol (4.53 g, 28.24 mmol) in toluene (140 mL) under an atmosphere of Ar(g) and at rt. The reaction mixture was degassed and backfilled with Ar(g) (×3), and the resulting mixture was heated under an atmosphere of Ar(g) at 100° C. for 18 h. The reaction mixture was cooled to rt. DCM (150 mL) was added and the reaction mixture was filtered. The filtrate was evaporated at reduced pressure, and the crude product was purified by flash chromatography on silica (EtOAc:hexane, 1:1) to give the title compound (4.0 g, 60%); $^1H$ NMR (400 MHz, $CDCl_3$) δ 7.37 (q, 2H), 7.14-7.04 (m, 2H), 6.11 (d, 1H), 5.97 (d, 1H), 5.33 (s, 2H), 3.97-3.85 (m, 1H), 3.83-3.31 (m, 5H), 2.35 (d, 1H), 1.85 (td, 2H), 1.45 (s, 9H), 1.25 (s, 1H).

Intermediate 55 rac-(1R,6R)-2-(6-((4-Chloro-2-fluorobenzyl)oxy)pyridin-2-yl)-2,5-diazabicyclo[4.2.0]octane 2 M HCl in $Et_2O$ (20 mL) was added to a stirred solution of rac-tert-butyl (1R,6R)-5-6-[(4-chloro-2-fluorophenyl)methoxy]pyridin-2-yl-2,5-diazabicyclo[4.2.0]octane-2-carboxylate Intermediate 54 (4.0 g, 8.93 mmol) in $Et_2O$ (50 mL) and the reaction mixture was stirred at rt for 1 h. The reaction mixture was cooled to +5° C., and the resultant solid precipitate was slurried for 16 h, and then collected by filtration and dried under reduced pressure to give the hydrochloride salt of the title compound (3.0 g, 89%) as a white solid; MS (ESI) m/z $[M+H]^+$ 348.2.

Intermediate 56 rac-Methyl 2-(((1R,6R)-5-(6-((4-chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylate Methyl 2-(chloromethyl)-1-((1-ethyl-1H-imidazol-5-yl)methyl)-4-methoxy-1H-benzo[d]imidazole-6-carboxylate dihydrochloride Intermediate 53 (1.7 g, 4.05 mmol) was added to a suspension of rac-(1R,6R)-2-(6-((4-chloro-2-fluorobenzyl)oxy)pyridin-2-yl)-2,5-diazabicyclo[4.2.0]octane dihydrochloride Intermediate 55 (0.6 g, 1.4 mmol) and $K_2CO_3$ (1.18 g, 8.56 mmol) in DMF (10 mL) and the reaction mixture was stirred at 50° C. for 16 h. The reaction mixture was allowed to cool to rt, diluted with water (10 mL), and extracted with EtOAc (3×10 mL). The combined organic layer was washed with brine (20 mL) and water (10 mL), dried over $Na_2SO_4$, filtered, and concentrated in vacuo. The crude product was purified by preparative HPLC, Prep-Method F, (gradient: 0-55%), to give the title compound (143 mg, 16%) as a brown solid; $^1H$ NMR (400 MHz, DMSO-$d_6$) δ 8.13 (d, 1H), 7.83 (d, 1H), 7.68 (s, 1H), 7.53-7.39 (m, 3H), 7.30 (d, 1H), 6.50 (s, 1H), 6.18-6.09 (m, 2H), 5.92-5.70 (m, 2H), 5.26 (s, 2H), 4.00 (q, 3H), 3.91-3.69 (m, 5H), 2.97 (d, 1H), 2.66 (d, 2H), 2.40-2.21 (m, 3H), 2.07 (d, 3H), 2.04-1.90 (m, 1H), 1.64 (d, 1H), 1.25 (t, 1H), 1.19 (t, 3H).

Intermediate 57 rel-Methyl 2-(((1R,6R)-5-(6-((4-chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylate Isomer 1

Intermediate 58 rel-Methyl 2-(((1R,6R)-5-(6-((4-chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylate Isomer 2

The stereoisomers of rac-methyl 2-(((1R,6R)-5-(6-((4-chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylate Intermediate 56 were separated by chiral chromatography on a CHIRALPAK IC-III column (5 μm, 250×20 mm), using an isocratic run of hexane:IPA:MeOH (50:25:25) as eluant;

- the first eluted compound was collected and concentrated at reduced pressure to give the title compound Isomer 1, Intermediate 57 (21 mg); MS (ESI) m/z $[M+H]^+$ 674.2; and
- the second eluted compound was collected and concentrated at reduced pressure to give the title compound Isomer 2, Intermediate 58 (17 mg); MS (ESI) m/z $[M+H]^+$ 674.2.

Intermediate 59

Methyl 3-(((5-methylisoxazol-3-yl)methyl)amino)-4-nitrobenzoate

Methyl 3-fluoro-4-nitrobenzoate (1.0 g, 5.02 mmol) was added in one portion to a solution of (5-methylisoxazol-3-yl)methanamine (0.563 g, 5.02 mmol) and $K_2CO_3$ (2.08 g, 15.06 mmol) in MeCN (20 mL), and the reaction mixture was stirred at 25° C. for 2 h. The reaction was quenched with sat brine (100 mL), and the reaction mixture was extracted with EtOAc (3×125 mL). The combined organic layer was dried over $Na_2SO_4$, filtered and concentrated at reduced pressure. The crude product was purified by flash chromatography on silica (0-50% EtOAc in petroleum ether) to give the title compound (0.800 g, 55%) as a yellow solid; MS (ESI) m/z $[M+H]^+$ 292.

Intermediate 60

Methyl 4-amino-3-(((5-methylisoxazol-3-yl)methyl)amino)benzoate

10% Pd—C (0.219 g, 0.21 mmol) was added to a solution of methyl 3-(((5-methylisoxazol-3-yl)methyl)amino)-4-nitrobenzoate Intermediate 59 (0.60 g, 2.06 mmol) in MeOH (10 mL) under an atmosphere of $N_2$(g). The reaction mixture was evacuated and backfilled with $H_2$(g) (×3) and the reaction mixture was stirred under an atmosphere of $H_2$(g) (3 atm) at 25° C. for 2 h. The reaction mixture was filtered through celite, washed with MeOH (100 mL) and the filtrate was collected and evaporated at reduced pressure. The residue was purified by preparative TLC (EtOAc:petroleum ether, 1:1), to give the title compound (0.400 g, 74%) as a yellow solid; MS (ESI) m/z $[M+H]^+$ 262.

Intermediate 61

Methyl 2-(chloromethyl)-1-((5-methylisoxazol-3-yl)methyl)-1H-benzo[d]imidazole-6-carboxylate Methyl 4-amino-3-(((5-methylisoxazol-3-yl)methyl)amino)benzoate Intermediate 60 (0.28 g, 1.07 mmol) was added in one portion to a solution of 2-chloro-1,1,1-trimethoxyethane (0.331 g, 2.14 mmol) and pTsOH monohydrate (0.020 g, 0.11 mmol) in MeCN (10 mL), and the reaction mixture was stirred at 25° C. for 4 h. The reaction was quenched with sat brine (100 mL), and the reaction mixture was extracted with EtOAc (3×75 mL). The combined organic layer was dried over $Na_2SO_4$, filtered and concentrated at reduced pressure. The residue was purified by preparative TLC (EtOAc:petroleum ether, 1:1) to give the title compound (0.150 g, 44%) as a yellow solid; MS (ESI) m/z $[M+H]^+$ 320.

Intermediate 62 rac-Methyl 2-(((1R,6S)-5-(6-((4-cyano-2-fluorobenzyl)oxy)pyridin-2-yl)-2,5-diazabicyclo[4.2.0]octan-2-yl)methyl)-1-((5-methylisoxazol-3-yl)methyl)-1H-benzo[d]imidazole-6-carboxylate Methyl 2-(chloromethyl)-1-((5-methylisoxazol-3-yl)methyl)-1H-benzo[d]imidazole-6-carboxylate Intermediate 61 (0.11 g, 0.34 mmol) was added in one portion to a solution of rac-4-(((6-((1R,6S)-2,5-diazabicyclo[4.2.0]octan-2-yl)pyridin-2-yl)oxy)methyl)-3-fluorobenzonitrile hydrochloride Intermediate 9 (0.129 g, 0.34 mmol) and $K_2CO_3$ (0.190 g, 1.38 mmol) in MeCN (4 mL) and the reaction mixture was stirred at 60° C. for 4 h. The reaction was quenched with sat brine (100 mL) and the reaction mixture was extracted with EtOAc (3×75 mL). The combined organic layer was dried over $Na_2SO_4$, filtered and concentrated at reduced pressure. The residue was purified by preparative TLC (EtOAc:petroleum ether, 1:1) to give the title compound (0.100 g, 47%) as a yellow solid; MS (ESI) m/z $[M+H]^+$ 622.

Intermediate 63

Methyl 3-(((4-methylpyridin-2-yl)methyl)amino)-4-nitrobenzoate

Methyl 3-fluoro-4-nitrobenzoate (0.5 g, 2.51 mmol) was added in one portion to a solution of (4-methylpyridin-2-yl)methanamine (0.307 g, 2.51 mmol) and $K_2CO_3$ (1.041 g, 7.53 mmol) in MeCN (10 mL) and the reaction mixture was stirred at 25° C. for 4 h. The reaction was quenched with sat brine (100 mL) and the reaction mixture was extracted with EtOAc (3×75 mL). The combined organic layer was dried over $Na_2SO_4$, filtered and concentrated at reduced pressure. The residue was purified by preparative TLC (EtOAc: petroleum ether, 1:1) to give the title compound (0.400 g, 53%) as a yellow solid. MS (ESI) m/z $[M+H]^+$ 302.

Intermediate 64

Methyl 4-amino-3-(((4-methylpyridin-2-yl)methyl)amino)benzoate

10% Pd—C (0.318 g, 0.30 mmol) was added to a solution of methyl 3-(((4-methylpyridin-2-yl)methyl)amino)-4-nitrobenzoate Intermediate 63 (0.9 g, 2.99 mmol) in MeOH (40 mL) under an atmosphere of $N_2$(g). The reaction mixture was evacuated and backfilled with $H_2$(g) (×3) and the reaction mixture was stirred under an atmosphere of $H_2$(g) (3 atm) at 25° C. for 2 h. The reaction mixture was filtered through celite, the filtercake was washed with MeOH (100 mL) and the filtrate was collected and concentrated at reduced pressure. The residue was purified by preparative TLC (DCM:MeOH, 10:1) to give the title compound (0.800 g, 99%) as a yellow solid; MS (ESI) m/z $[M+H]^+$ 272.

Intermediate 65

Methyl 2-(chloromethyl)-1-((4-methylpyridin-2-yl)methyl)-1H-benzo[d]imidazole-6-carboxylate Methyl 4-amino-3-(((4-methylpyridin-2-yl)methyl)amino)benzoate Intermediate 64 (100 mg, 0.37 mmol) was added to a mixture of 2-chloro-1,1,1-trimethoxyethane (68 mg, 0.44 mmol) and pTsOH (13 mg, 0.07 mmol) in MeCN (2 mL) under an atmosphere of $N_2$(g) and the reaction mixture was stirred at 25° C. for 3 h. The reaction mixture was concentrated at reduced pressure to give the title compound (0.099 g, 81%) as a brown gum; MS (ESI) m/z $[M+H]^+$ 330.

Intermediate 66 rac-Methyl 2-(((1R,6S)-5-(6-((4-cyano-2-fluorobenzyl)oxy)pyridin-2-yl)-2,5-diazabicyclo[4.2.0]octan-2-yl)methyl)-1-((4-methylpyridin-2-yl)methyl)-1H-benzo[d]imidazole-6-carboxylate Methyl 2-(chloromethyl)-1-((4-methylpyridin-2-yl)methyl)-1H-benzo[d]imidazole-6-carboxylate Intermediate 65 (100 mg, 0.30 mmol) was added to a solution of rac-4-(((6-((1R,6S)-2,5-diazabicyclo[4.2.0]octan-2-yl)pyridin-2-yl)oxy)methyl)-3-fluorobenzonitrile hydrochloride Intermediate 9 (136 mg, 0.30 mmol) and $K_2CO_3$ (210 mg, 1.52 mmol) in MeCN (5 mL), under an atmosphere of $N_2$(g), and the reaction mixture was stirred at 80° C. for 1 h. The reaction was quenched with water (100 mL), and the reaction mixture was extracted with EtOAc (3×100 mL). The combined organic layer was dried over $Na_2SO_4$, filtered and concentrated at reduced pressure. The residue was purified by preparative TLC (DCM:MeOH, 17:1), to give the title compound (0.090 g, 47%) as a yellow solid; MS (ESI) m/z $[M+H]^+$ 632.

Intermediate 67

Methyl (S)-2-(chloromethyl)-5-fluoro-1-(oxetan-2-ylmethyl)-1H-benzo[d]imidazole-6-carboxylate The title compound was prepared as described in WO2020103815.

Intermediate 68

5-Bromo-3-chloro-2-nitro-N-(oxetan-2-ylmethyl)aniline

5-Bromo-1-chloro-3-fluoro-2-nitrobenzene (1.0 g, 3.93 mmol) was added to a solution of oxetan-2-ylmethanamine (0.51 g, 5.11 mmol), DIPEA (3.43 mL, 19.65 mmol) in DMF (10 mL) and the reaction mixture was stirred at 25° C. for 2 h. The reaction mixture was diluted with EtOAc (20 mL), and washed with sat brine (3×50 mL). The combined organic layer was dried over $Na_2SO_4$, filtered and concentrated at reduced pressure, and the residue was purified by preparative TLC (petroleum ether:EtOAc, 1:1) to give the title compound (1.04 g, 82%) as a white solid; MS (ESI) m/z $[M+H]^+$ 323.

Intermediate 69

5-Bromo-3-chloro-$N^1$-(oxetan-2-ylmethyl)benzene-1,2-diamine

5-Bromo-3-chloro-2-nitro-N-(oxetan-2-ylmethyl)aniline Intermediate 68 (1.0 g, 3.11 mmol) was added to a suspension of Fe(s) (0.868 g, 15.55 mmol) and $NH_4Cl$ (0.832 g, 15.55 mmol) in MeOH (15 mL), and the reaction mixture was stirred at 60° C. for 2 h. The reaction mixture was filtered through celite, the filtrate was concentrated in vacuo, and the residue was purified by preparative TLC (petroleum ether:EtOAc, 1:1) to give the title compound (0.870 g, 96%) as a white solid; MS (ESI) m/z $[M+H]^+$ 293.

Intermediate 70

Methyl 4-amino-3-chloro-5-((oxetan-2-ylmethyl)amino)benzoate

5-Bromo-3-chloro-$N^1$-(oxetan-2-ylmethyl)benzene-1,2-diamine Intermediate 69 (700 mg, 2.40 mmol) was added to a suspension of DIPEA (4.19 ml, 24.01 mmol), $Pd(dppf)Cl_2$ (176 mg, 0.24 mmol) in MeOH (10 mL) and the reaction mixture was stirred under an atmosphere of CO(g) (60 atm) at 100° C. for 48 h. The reaction mixture was filtered through celite and the filtrate was concentrated in vacuo. The residue was purified by preparative TLC (petroleum ether: EtOAc, 1:1) to give the title compound (0.560 g, 86%) as a brown oil; MS (ESI) m/z $[M+H]^+$ 271.

Intermediate 71

Methyl 4-chloro-2-(chloromethyl)-1-(oxetan-2-ylmethyl)-1H-benzo[d]imidazole-6-carboxylate 2-Chloro-1,1,1-trimethoxyethane (343 mg, 2.22 mmol) was added to a solution of methyl 4-amino-3-chloro-5-((oxetan-2-ylmethyl)amino)benzoate Intermediate 70 (300 mg, 1.11 mmol) and pTsOH (10.54 mg, 0.06 mmol) in MeCN (6 mL) and the reaction mixture was stirred at 25° C. for 2 h. The reaction mixture was concentrated in vacuo and the residue was purified by preparative TLC (petroleum ether:EtOAc, 1:1) to give the title compound (0.240 g, 66%) as a white solid; MS (ESI) m/z $[M+H]^+$ 329.

Intermediate 72

3-Bromo-2-chloro-6-nitro-N-(oxetan-2-ylmethyl)aniline

1-Bromo-2-chloro-3-fluoro-4-nitrobenzene (3.72 g, 14.62 mmol) was added in one portion to a solution of oxetan-2-ylmethanamine (1.53 g, 17.54 mmol) and DIPEA (7.56 g, 58.48 mmol) in DMF (30 mL) and the reaction mixture was stirred at 25° C. for 2 h. The reaction was quenched with sat brine (20 mL), and the mixture was extracted with EtOAc (3×20 mL). The combined organic layer was dried over $Na_2SO_4$, filtered and concentrated at reduced pressure. The crude product was purified by flash column chromatography on silica (0-30% EtOAc in petroleum ether) to give the title compound (3.83 g, 82%) as a yellow solid; MS (ESI) m/z $[M+H]^+$ 323.

Intermediate 73

Methyl 2-chloro-4-nitro-3-((oxetan-2-ylmethyl)amino)benzoate $Pd(OAc)_2$ (0.070 g, 0.31 mmol) was added in one portion to a suspension of 3-bromo-2-chloro-6-nitro-N-(oxetan-2-ylmethyl)aniline Intermediate 72 (1.0 g, 3.11 mmol), $Co_2CO_8$ (0.160 g, 0.93 mmol), DMAP (0.760 g, 6.22 mmol) and XantPhos (0.180 g, 0.31 mmol) in a mixture of toluene (10 mL) and MeOH (5 mL) and under an atmosphere of $N_2$(g). The reaction mixture was stirred at 90° C. for 1 h. The reaction mixture was diluted with EtOAc (20 mL), and washed with sat brine (2×20 mL). The organic layer was dried over $Na_2SO_4$, filtered and concentrated at reduced pressure. The residue was purified by preparative TLC (petroleum ether:EtOAc, 1:1), to give the title compound (0.400 g, 43%) as a yellow oil; MS (ESI) m/z $[M+H]^+$ 301.

Intermediate 74

Methyl 4-amino-2-chloro-3-((oxetan-2-ylmethyl)amino)benzoate

Fe(s) (0.371 g, 6.65 mmol) was added in one portion to a solution of methyl 2-chloro-4-nitro-3-((oxetan-2-ylmethyl)amino)benzoate Intermediate 73 (0.4 g, 1.33 mmol) and $NH_4Cl$ (0.427 g, 7.98 mmol) in MeOH (6 mL) and water (2 mL), and the reaction mixture was stirred at 60° C. for 3 h. The reaction mixture was filtered through celite, and the filter cake was washed with MeOH (20 mL). The filtrate was concentrated at reduced pressure and the residue was diluted with EtOAc (20 mL). The organic layer was washed with sat brine (2×20 mL), dried over $Na_2SO_4$, filtered and concentrated at reduced pressure. The residue was purified by preparative TLC (petroleum ether:EtOAc, 1:1), to give the title compound (0.260 g, 72%) as a yellow solid; MS (ESI) m/z $[M+H]^+$ 271.

Intermediate 75

Methyl 7-chloro-2-(chloromethyl)-1-(oxetan-2-ylmethyl)-1H-benzo[d]imidazole-6-carboxylate pTsOH (0.025 g, 0.15 mmol) was added in one portion to a solution of methyl 4-amino-2-chloro-3-((oxetan-2-ylmethyl)amino)benzoate Intermediate 74 (0.20 g, 0.74 mmol) and 2-chloro-1,1,1-trimethoxyethane (0.171 g, 1.11 mmol) in MeCN (2 mL) and the reaction mixture was stirred at 20° C. for 2 h. The reaction mixture was concentrated at reduced pressure and the residue was diluted with EtOAc (20 mL). The organic layer was washed sequentially with water (2×20 mL), dried over $Na_2SO_4$, filtered and concentrated at reduced pressure to give the crude title compound (0.25 g, 103%); MS (ESI) m/z $[M+H]^+$ 329.

Intermediate 76

Methyl 1-(2-(tert-butoxy)ethyl)-2-(chloromethyl)-1H-benzo[d]imidazole-6-carboxylate The title compound was prepared in three steps from methyl 3-fluoro-4-nitrobenzoate and 2-(tert-butoxy)ethan-1-amine in analogy with the description of Intermediate 7. Yield (310 mg, 85%); MS (ESI) m/z $[M+H]^+$ 325.

Intermediate 77

Methyl 1-(2-butoxyethyl)-2-(chloromethyl)-1H-benzo[d]imidazole-6-carboxylate

The title compound was prepared in three steps from methyl 3-fluoro-4-nitrobenzoate and 2-butoxyethan-1-amine in analogy with the description of Intermediate 7. Yield (200 mg, 55%); MS (ESI) m/z $[M+H]^+$ 325.

Intermediate 78

Methyl 4-amino-2-chloro-5-((oxetan-2-ylmethyl) amino)benzoate

The title compound was prepared in two steps from methyl 2-chloro-5-fluoro-4-nitrobenzoate and oxetan-2-ylmethanamine in analogy with the description of Intermediate 15. Yield (170 mg, 94%); MS (ESI) m/z $[M+H]^+$ 271.0.

Intermediate 79 rac-(4aR,7aS)-1-(6-((4-Chloro-2-fluorobenzyl)oxy) pyridin-2-yl)octahydrofuro[3,4-b]pyrazine Step a) rac-tert-Butyl (4aR,7aS)-4-(6-((4-chloro-2-fluorobenzyl)oxy)pyridin-2-yl)hexahydrofuro[3,4-b] pyrazine-1(2H)carboxylate 2-Bromo-6-((4-chloro-2-fluorobenzyl)oxy)pyridine (WO2020207474) (1.36 g, 4.31 mmol), rac-tert-butyl (4aR,7aS)-hexahydrofuro[3,4-b]pyrazine-1(2H)-carboxylate (984 mg, 4.31 mmol), sodium tert-butoxide (497 mg, 5.17 mmol) and XantPhos (249 mg, 431.1 μmol) were suspended in degassed toluene (150 mL). $Pd_2(dba)_3$ (197 mg, 215.55 μmol) was added under Ar(g), and the reactor was degassed one more time. The mixture was heated under Ar(g) at reflux overnight. After cooling to rt, the mixture was diluted with MTBE, the organic layer was washed with water and sat brine, dried over $MgSO_4$, filtered, and concentrated in vacuo to give the sub-title Step a) compound (2.1 g, 65%); MS (ESI) m/z $[M+H]^+$ 464.0.

Step b) rac-(4aR,7aS)-1-(6-((4-Chloro-2-fluorobenzyl)oxy)pyridin-2-yl)octahydrofuro[3,4-b]pyrazine rac-tert-Butyl (4aR,7aS)-4-(6-((4-chloro-2-fluorobenzyl) oxy)pyridin-2-yl)hexahydrofuro[3,4-b]pyrazine-1(2H)-carboxylate (1.97 g, 4.24 mmol) was dissolved in dioxane (50 mL). HCl (4.3 mL, 16.98 mmol) was added, and the mixture was stirred at ambient temperature overnight. The crystalline precipitate was filtered, washed with cool dioxane (15 mL) and dried in vacuo to give the title compound as an hydrochloride salt (1.21 g, 57%) $^1$H NMR (500 MHz, DMSO-$d_6$) δ 10.38 (s, 1H), 9.29 (s, 1H), 7.53 (q, 1H), 7.48 (dd, 1H), 7.31 (d, 1H), 6.42 (d, 1H), 6.20 (d, 1H), 5.33 (s, 1H), 5.09 (d, 1H), 4.00 (m, 6H), 3.41-3.31 (m, 1H), 3.17-3.11 (m, 2H).

Intermediate 80 rac-tert-Butyl (4aR,7aS)-4-(6-((4-cyano-2-fluorobenzyl)oxy)pyridin-2-yl)hexahydrofuro[3,4-b] pyrazine-1(2H)-carboxylate 4-[(6-Bromopyridin-2-yl)oxy]methyl-3-fluorobenzonitrile (WO2021081207) (1.35 g, 4.4 mmol), rac-tert-butyl (4aR,7aS)-hexahydrofuro[3,4-b]pyrazine-1(2H)-carboxylate (1.0 g, 4.4 mmol), sodium tert-butoxide (507 mg, 5.28 mmol) and XantPhos (255 mg, 440 μmol) were suspended in degassed toluene (50 mL). $Pd_2(dba)_3$ (201 mg, 220 μmol) was added under argon, and the reactor was degassed one more time. The reaction mixture was heated under argon at reflux overnight. After cooling to rt, the mixture was diluted with MTBE, and the organic layer was washed with water and sat brine, dried over $MgSO_4$, filtered, and concentrated in vacuo. The residue was purified by preparative HPLC, PrepMethod E, (gradient: 10-50%) to give the title compound (800 mg, 38%); MS (ESI) m/z $[M+H]^+$ 455.2.

Intermediate 81 rac-3-Fluoro-4-(((6-((4aR,7aS)-hexahydrofuro[3,4-b]pyrazin-1(2H-yl)pyridin-2-yl)oxy)methyl)benzonitrile 4 M HCl (aq, 1.26 mL) was added to a solution of rac-tert-butyl (4aR,7aS)-4-(6-((4-cyano-2-fluorobenzyl) oxy)pyridin-2-yl)hexahydrofuro[3,4-b]pyrazine-1(2H)-carboxylate Intermediate 80 (454 mg, 998 μmol) in 1,4-dioxane (50 mL), and the reaction mixture was stirred at ambient temperature overnight. The crystalline precipitate was filtered off, washed with cool 1,4-dioxane (15 mL) and dried in vacuo to give the title compound as a HCl salt (200 mg, 51%); $^1$H NMR (500 MHz, DMSO-$d_6$) δ 10.39 (s, 1H), 9.29 (s, 1H), 7.77-7.64 (m, 2H), 7.54 (q, 2H), 7.01 (d, 2H), 6.64 (d, 2H), 6.42 (d, 1H), 6.23 (dd, 1H), 5.50-5.31 (m, 2H), 5.10-4.98 (m, 1H), 4.08 (t, 1H), 3.95 (d, 3H), 3.85 (t, 2H), 3.58 (d, 1H), 3.41-3.29 (m, 1H), 3.15 (t, 1H).

Intermediate 82

Methyl 2-(((4aRS,7aSR)-4-(6-((4-chloro-2-fluorobenzyl)oxy)pyridin-2-yl)hexahydrofuro[3,4-b] pyrazin-1(2H)-yl)methyl)-1-(((S)-oxetan-2-yl) methyl)-1H-benzo[d]imidazole-6-carboxylate rac-(4aR,7aS)-1-(6-((4-Chloro-2-fluorobenzyl)oxy)pyridin-2-yl)octahydrofuro[3,4-b]pyrazine Intermediate 79 (302 mg, 755.5 μmol), methyl (S)-2-(chloromethyl)-1-(oxetan-2-ylmethyl)-1H-benzo[d]imidazole-6-carboxylate (1.1 g, 3.73 mmol) and DIPEA (3.0 g, 23.21 mmol) were mixed in MeCN (30 mL). A catalytic amount of NaI was added, and the mixture was heated at 45° C. overnight. The reaction mixture was cooled to rt, poured into water (100 mL), and extracted with EtOAc (2×100 mL). The combined organic layer was washed with water and sat brine, dried over $MgSO_4$, filtered, and concentrated in vacuo to give the title compound (440 mg, 61%); MS (ESI) m/z $[M+H]^+$ 622.4.

Intermediate 83

Methyl 2-(((4aRS,7aSR)-4-(6-((4-chloro-2-fluorobenzyl)oxy)pyridin-2-yl)hexahydrofuro[3,4-b] pyrazin-1(2H)-yl)methyl)-4-methoxy-1-(((S)-oxetan-2-yl)methyl)-1H-benzo[d]imidazole-6-carboxylate rac-(4aR,7aS)-1-(6-((4-Chloro-2-fluorobenzyl)oxy)pyridin-2-yl)octahydrofuro[3,4-b]pyrazine Intermediate 79 (340 mg, 935 μmol), methyl (S)-2-(chloromethyl)-4-methoxy-1-(oxetan-2-ylmethyl)-1H-benzo[d]imidazole-6-carboxylate Intermediate 25 (265 mg, 814 μmol), DIPEA (401 mg, 3.1 mmol, 540 μl, 4.0 equiv) and NaI (12 mg, 78 μmol) were suspended in MeCN (5 mL), and the reaction mixture was stirred at 40° C. for 16 h. The reaction mixture was diluted with water, and extracted with EtOAc. The combined organic layer was dried and evaporated, and the residue was purified by preparative HPLC, PrepMethod E, (gradient: 40-65%) to give the title compound (120 mg, 23%); MS (ESI) m/z $[M+H]^+$ 652.0

Intermediate 84

Methyl 2-(((4aR*,7aS*)-4-(6-((4-chloro-2-fluorobenzyl)oxy)pyridin-2-yl)hexahydrofuro[3,4-b]pyrazin-1(2H)-yl)methyl)-4-methoxy-1-(((S)-oxetan-2-yl)methyl)-1H-benzo[d]imidazole-6-carboxylate, Isomer 1

Intermediate 85

Methyl 2-(((4aR*,7aS*)-4-(6-((4-chloro-2-fluorobenzyl)oxy)pyridin-2-yl)hexahydrofuro[3,4-b]pyrazin-1(2H)-yl)methyl)-4-methoxy-1-(((S)-oxetan-2-yl)methyl)-1H-benzo[d]imidazole-6-carboxylate, Isomer 2

The diastereomers of methyl 2-(((4aRS,7aSR)-4-(6-((4-chloro-2-fluorobenzyl)oxy)pyridin-2-yl)hexahydrofuro[3,4-b]pyrazin-1(2H)-yl)methyl)-4-methoxy-1-(((S)-oxetan-2-yl)methyl)-1H-benzo[d]imidazole-6-carboxylate Intermediate 83 were separated by chiral chromatography on a Chiralpak IC ((250×4.6 mm, 5 μm) eluted with IPA-MeOH (50:50) at a flow rate of 0.6 mL/min;

is the first eluted compound was collected and evaporated to give the title compound Isomer 1, Intermediate 4 (58 mg); MS (ESI) m/z $[M+H]^+$ 652.1; and the second eluted compound was collected and evaporated to give the title compound Isomer 2, Intermediate 85 (60 mg); MS (ESI) m/z $[M+H]^+$ 652.1.

Intermediate 86

Methyl 2-(((4aRS,7aSR)-4-(6-((4-cyano-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylate rac-3-Fluoro-4-(((6-((4aR,7aS)-hexahydrofuro[3,4-b]pyrazin-1(2H)-yl)pyridin-2-yl)oxy)methyl)benzonitrile Intermediate 81 (255 mg, 653 μmol), methyl (S)-2-(chloromethyl)-1-(oxetan-2-ylmethyl)-1H-benzo[d]imidazole-6-carboxylate (231 mg, 783 μmol) and DIPEA (253 mg, 1.96 mmol) were mixed in MeCN (30 mL). A catalytic amount of NaI was added and the reaction mixture was heated at 45° C. overnight. Water (10 mL) was added to the reaction mixture and the mixture was extracted with EtOAc (2×100 mL). The combined organic layer was washed with water and sat brine, dried over $MgSO_4$, filtered, and concentrated in vacuo and the residue was purified by preparative HPLC, PrepMethod N (gradient: 55-70%) to give the title compound (62 mg, 23%);

MS (ESI) m/z $[M+H]^+$ 613.2; $^1$H NMR (400 MHz, $CDCl_3$) δ 8.12 (dd, 1H), 7.99 (m, 1H), 7.76 (dd, 1H), 7.58 (td, 1H), 7.40 (m, 3H), 6.24-6.05 (m, 2H), 5.48-5.08 (m, 4H), 4.94 (m, 1H), 4.76-4.59 (m, 2H), 4.57-4.47 (m, 1H), 4.36-4.27 (m, 1H), 4.12-3.99 (m, 1H), 3.95 (s, 3H), 3.83 (dt, 1H), 3.75-3.57 (m, 2H), 3.52 (dd, 1H), 2.88 (m, 3H), 2.71-2.58 (m, 1H), 2.41 (td, 1H), 2.00 (s, 2H).

Intermediate 87

Methyl 3-fluoro-4-nitro-5-(((tetrahydrofuran-3-yl)methyl)amino)benzoate

Methyl 3,5-difluoro-4-nitrobenzoate (4.0 g, 18.42 mmol), 1-(oxolan-3-yl) methanamine (1.86 g, 18.42 mmol) and DIPEA (4.76 g, 36.85 mmol) were mixed in THF (20 mL) and the reaction mixture was stirred at 45° C. for 16 h. The reaction mixture was cooled to rt and then diluted with water and extracted with MTBE. The combined organic layer was washed with brine, dried over anhydrous $Na_2SO_4$, and filtered. The filtrate was concentrated to give the title compound (3.6 g, 55%) as a yellow oil; MS (ESI) m/z $[M+H]^+$ 299.1.

Intermediate 88

Methyl 4-amino-3-fluoro-5-(((tetrahydrofuran-3-yl)methyl)amino)benzoate

Methyl 3-fluoro-4-nitro-5-((oxolan-3-yl)methyl)amino-benzoate Intermediate 87 (3.6 g, 12.07 mmol) was dissolved in THE (20 mL) and treated with 10% Pd/C (360 mg), and the reaction mixture was hydrogenated under an atmosphere of $H_2$(g) at ambient pressure and temperature until the reaction was complete. The reaction mixture was filtered and the filtrate was collected and concentrated in vacuo, and the residue was purified by chromatography on silica (EtOAc:hexane, 1:1) to give the title compound (2.0 g, 59%); MS (ESI) m/z $[M+H]^+$ 269.2.

Intermediate 89

Methyl 2-(chloromethyl)-4-fluoro-1-((tetrahydrofuran-3-yl)methyl)-1H-benzo[d]imidazole-6-carboxylate 2-Chloro-1,1,1-trimethoxyethane (2.49 g, 16.1 mmol) and pTsOH hydrate (255 mg, 1.34 mmol) were added to a solution of methyl 4-amino-3-fluoro-5-((oxolan-3-yl)methyl)aminobenzoate Intermediate 88 (3.6 g, 13.42 mmol) in THE (50 mL) and the reaction mixture was stirred at 50° C. overnight. The reaction mixture was poured into water and extracted with EtOAc. The combined organic layer was washed with brine and concentrated under vacuum to give the title compound (1.1 g, 23%); MS (ESI) m/z $[M+H]^+$ 327.2.

Intermediate 90 rac-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-4-fluoro-1-((tetrahydrofuran-3-yl)methyl)-1H-benzo[d]imidazole-6-carboxylate Methyl 2-(chloromethyl)-4-fluoro-1-((tetrahydrofuran-3-yl)methyl)-1H-benzo[d]imidazole-6-carboxylate Intermediate 89 (1.1 g, 3.37 mmol), rac-(4aR,7aS)-1-(6-((4-Chloro-2-fluorobenzyl)oxy)pyridin-2-yl)octahydrofuro[3,4-b]pyrazine dihydrochloride Intermediate 79 (1.47 g, 3.37 mmol) and DIPEA (2.18 g, 16.83 mmol) were mixed in MeCN (5 mL) and the reaction mixture was stirred at rt for 16 h. The reaction mixture was diluted with water and extracted with EtOAc. The organic layer was dried over $Na_2SO_4$, filtered and evaporated, and the residue was purified by preparative HPLC, PrepMethod E, (gradient: 10-50%) to give the title compound (125 mg, 2.2%); MS (ESI) m/z $[M+H]^+$ 654.0.

Intermediate 91 rel-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-4-fluoro-1-(((S)-tetrahydrofuran-3-yl)methyl)-1H-benzo[d]imidazole-6-carboxylate Isomer 2

Intermediate 92 rel-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-4-fluoro-1-(((S)-tetrahydrofuran-3-yl)methyl)-1H-benzo[d]imidazole-6-carboxylate Isomer 3

The stereoisomers of rac-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-4-fluoro-1-((tetrahydrofuran-3-yl)methyl)-1H-benzo[d]imidazole-6-carboxylate Intermediate 90 were separated by chiral chromatography on a Chiralcel OD-H (250×20 mm, 5 μm), eluted with hexane:IPA:MeOH, (50:25:25) at a flow rate of 12 mL/min;

the first eluted compound mixture was collected and evaporated to give a mixture of isomers and the second eluted compound mixture was collected and evaporated to give a mixture of isomers.

The stereoisomers of the first eluted compound mixture were separated by chiral chromatography on a Chiralpak AD-H (250×30 mm, 5 μm) eluted with hexane:IPA:MeOH (50:25:25) at a flow rate of 15 mL/min;

the second eluted compound was collected and evaporated to give the title compound Isomer 2 (47 mg); MS (ESI) m/z 654.2.

The stereoisomers of the second eluted compound mixture were separated by chiral chromatography on a Chiralpak AD-H (250×30 mm, 5 μm) eluted with hexane:IPA:MeOH (50:25:25) at a flow rate of 15 mL/min;

The first eluted compound was collected and evaporated to give the title compound Isomer 3 (10 mg); MS (ESI) m/z 654.2.

Intermediate 93

Methyl 2-(((4aRS,7aSR)-4-(6-((4-chloro-2-fluorobenzyl)oxy)pyridin-2-yl)hexahydrofuro[3,4-b]pyrazin-1(2H)-yl)methyl)-4-fluoro-1-(((S)-oxetan-2-yl)methyl)-1H-benzo[d]imidazole-6-carboxylate rac-(4aR,7aS)-1-(6-((4-Chloro-2-fluorobenzyl)oxy)pyridin-2-yl)octahydrofuro[3,4-b]pyrazine dihydrochloride Intermediate 79 (250 mg, 573 μmol), methyl (S)-2-(chloromethyl)-4-fluoro-1-(oxetan-2-ylmethyl)-1H-benzo[d]imidazole-6-carboxylate Intermediate 16 (179 mg, 573 μmol), DIPEA (371 mg, 2.87 mmol) and NaI (8.6 mg, 57 μmol) were mixed in MeCN (3 mL), and the reaction mixture was stirred at 40° C. for 16 h. The reaction mixture was diluted with water (8 mL) and extracted with EtOAc (3×5 mL). The combined organic layer was dried over $Na_2SO_4$, filtered and evaporated, and the residue was purified by preparative HPLC, PrepMethod E (gradient 15-35%) to give the title compound (115 mg, 30%); MS (ESI) m/z $[M+H]^+$ 640.2.

Intermediate 94

Methyl 2-(((4aR*,7aS*)-4-(6-((4-chloro-2-fluorobenzyl)oxy)pyridin-2-yl)hexahydrofuro[3,4-b]pyrazin-1(2H)-yl)methyl)-4-fluoro-1-(((S)-oxetan-2-yl)methyl)-1H-benzo[d]imidazole-6-carboxylate, Isomer 1

Intermediate 95

Methyl 2-(((4aR*,7aS*)-4-(6-((4-chloro-2-fluorobenzyl)oxy)pyridin-2-yl)hexahydrofuro[3,4-b]pyrazin-1(2H)-yl)methyl)-4-fluoro-1-(((S)-oxetan-2-yl)methyl)-1H-benzo[d]imidazole-6-carboxylate, Isomer 2

The stereoisomers of methyl 2-(((4aRS,7aSR)-4-(6-((4-chloro-2-fluorobenzyl)oxy)pyridin-2-yl)hexahydrofuro[3,4-b]pyrazin-1(2H)-yl)methyl)-4-fluoro-1-(((S)-oxetan-2-yl)methyl)-1H-benzo[d]imidazole-6-carboxylate Intermediate 93 were separated by chiral chromatography on a Chiralpak IA column (250×20 mm, 5 μm), eluted with hexane:IPA:MeOH (70:15:15), at a flow rate of 12 mL/min;

the first eluted compound was collected and evaporated to give the title compound Isomer 1 Intermediate 94 (46 mg); MS (ESI) m/z $[M+H]^+$ 640.0; and the second eluted compound was collected and evaporated to give the title compound Isomer 2 Intermediate 95 (41 mg); MS (ESI) m/z $[M+H]^+$ 640.0.

Intermediate 96

Methyl 4-nitro-3-((oxazol-4-ylmethyl)amino)benzoate (1,3-Oxazol-4-yl)methanamine hydrochloride (4.97 g, 36.91 mmol), methyl 3-fluoro-4-nitrobenzoate (7.0 g, 35.15 mmol) and DIPEA (9.99 g, 77.33 mmol) were mixed in THF (20 mL) and the reaction mixture was stirred at 45° C. for 2 h. The reaction mixture was diluted with water and extracted with MTBE. The combined organic layer was washed with brine, dried over anhydrous $Na_2SO_4$, and filtered. The filtrate was concentrated to give the title compound (8.0 g, 78%); MS (ESI) m/z $[M+H]^+$ 278.2.

Intermediate 97

Methyl 4-amino-3-((oxazol-4-ylmethyl)amino)benzoate

Methyl 4-nitro-3-((oxazol-4-ylmethyl)amino)benzoate Intermediate 96 (8.0 g, 27.41 mmol) was dissolved in THE (60 mL) and mixed with 10% Pd/C (0.8 mg) and the reaction mixture was hydrogenated under an atmosphere of $H_2(g)$ at ambient pressure and temperature until the reaction was complete. The reaction mixture was filtered and the filtrate was concentrated to give the title compound (6.9 g, 92%); MS (ESI) m/z $[M+H]^+$ 248.0.

Intermediate 98

Methyl 2-(chloromethyl)-1-(oxazol-4-ylmethyl)-1H-benzo[d]imidazole-6-carboxylate Methyl 4-amino-3-((oxazol-4-ylmethyl)amino)benzoate Intermediate 97 (2.0 g, 8.09 mmol) was dissolved in THE (50 mL). 2-Chloro-1,1,1-trimethoxyethane (1.5 g, 9.71 mmol) and pTSOH hydrate (77 mg, 404 μmol) were added and the reaction mixture was stirred at 50° C. overnight. The reaction mixture was poured into water and extracted with EtOAc. The combined organic layer was washed with brine, dried over $Na_2SO_4$, filtered and concentrated in vacuo to give the title compound (1.8 g, 69%); MS (ESI) m/z $[M+H]^+$ 306.0.

Intermediate 99 rac-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(oxazol-4-ylmethyl)-1H-benzo[d]imidazole-6-carboxylate Methyl 2-(chloromethyl)-1-(oxazol-4-ylmethyl)-1H-benzo[d]imidazole-6-carboxylate Intermediate 98 (400 mg, 1.31 mmol), rac-(4aR,7aS)-1-(6-((4-chloro-2-fluorobenzyl)oxy)pyridin-2-yl)octahydrofuro[3,4-b]pyrazine dihydrochloride Intermediate 79 (657 mg, 1.51 mmol), DIPEA (1.14 ml, 6.54 mmol) and NaI (19.6 mg, 131 μmol) were mixed in MeCN (5 mL), and the reaction mixture was stirred at 40° C. 16 h. The reaction mixture was diluted with water and extracted with EtOAc. The organic layer was dried over $Na_2SO_4$, filtered and evaporated and the residue was purified by preparative HPLC, PrepMethod E (gradient 25-30%) to give the title compound (370 mg, 42%): MS (ESI) m/z $[M+H]^+$ 664.0.

Intermediate 100 rel-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(oxazol-4-ylmethyl)-1H-benzo[d]imidazole-6-carboxylate Isomer 1

The stereoisomers of rac-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(oxazol-4-ylmethyl)-1H-benzo[d]imidazole-6-carboxylate Intermediate 99 were separated by chiral chromatography on a Chiralpak IB column (250×20 mm, 5 μm), eluted with hexane:IPA:MeOH (70:15:15) at a flow rate of 12 mL/min;

the first eluted compound was collected and evaporated to give the title compound Isomer 1 Intermediate 100 (149 mg); MS (ESI) m/z $[M+H]^+$ 633.2.

Intermediate 101

Methyl 4-nitro-3-((pyridin-3-ylmethyl)amino)benzoate

Methyl 3-fluoro-4-nitrobenzoate (3.0 g, 15.07 mmol), (pyridin-3-yl)methanamine (1.96 g, 18.08 mmol) and DIPEA (3.89 g, 30.13 mmol) were mixed in THE (10 mL), and the reaction mixture was stirred at 45° C. for 2 h. The reaction mixture was diluted with water and extracted with MTBE. The combined organic layer was washed with brine, dried over anhydrous $Na_2SO_4$, and filtered. The filtrate was concentrated in vacuo to give the title compound (4.2 g, 92%); MS (ESI) m/z $[M+H]^+$ 288.2.

Intermediate 102

Methyl 4-amino-3-((pyridin-3-ylmethyl)amino)benzoate

Methyl 4-nitro-3-((pyridin-3-ylmethyl)amino)benzoate Intermediate 101 (4.2 g, 13.89 mmol) was dissolved in THE (20 mL) and treated with 10% Pd/C (420 mg) and the reaction mixture was hydrogenated under an atmosphere of $H_2$(g) at ambient pressure and temperature until the reaction was complete. The reaction mixture was filtered and the filtrate was concentrated in vacuo and the residue was purified by chromatography on silica (EtOAc:hexane, 1:1) to give the title compound (3.2 g, 81%); MS (ESI) m/z $[M+H]^+$ 258.2.

Intermediate 103

Methyl 2-(chloromethyl)-1-(pyridin-3-ylmethyl)-1H-benzo[d]imidazole-6-carboxylate 2-Chloro-1,1,1-trimethoxyethane (361 mg, 2.33 mmol) and pTsOH hydrate (37 mg, 194 μmol) was added to a solution of methyl 4-amino-3-((pyridin-3-ylmethyl)amino)benzoate Intermediate 102 (500 mg, 1.94 mmol) in THF (50 mL) and the mixture was stirred at 50° C. overnight. The reaction mixture was poured into water and extracted with EtOAc. The combined organic layer was washed with brine and concentrated in vacuo to give the hydrochloride salt of the title compound (351 mg, 39%); MS (ESI) m/z $[M+H]^+$ 316.2.

Intermediate 104 rac-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(pyridin-3-ylmethyl)-1H-benzo[d]imidazole-6-carboxylate Methyl 2-(chloromethyl)-1-(pyridin-3-ylmethyl)-1H-benzo[d]imidazole-6-carboxylate dihydrochloride Intermediate 103 (352 mg, 1.11 mmol), rac-(4aR,7aS)-1-(6-((4-chloro-2-fluorobenzyl)oxy)pyridin-2-yl)octahydrofuro[3,4-b]pyrazine dihydrochloride Intermediate 79 (341 mg, 780 μmol) and DIPEA (680 μL, 3.9 mmol) were mixed in MeCN (3 mL) and the reaction mixture was stirred at 40° C. for 16 h. The reaction mixture was diluted with water and extracted with EtOAc. The organic layer was dried over $Na_2SO_4$, filtered and evaporated and the residue was purified by preparative HPLC, PrepMethod E, (gradient: 10-50%) to give the title compound (94 mg, 18%); MS (ESI) m/z $[M+H]^+$ 643.2.

Intermediate 105 rel-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(pyridin-3-ylmethyl)-1H-benzo[d]imidazole-6-carboxylate, Isomer 1

The stereoisomers of rac-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(pyridin-3-ylmethyl)-1H-benzo[d]imidazole-6-carboxylate Intermediate 104 were separated by chiral chromatography on a Chiralpak IB column (250×20 mm, 5 μm), eluted with hexane:IPA:MeOH (50:25:25) at a flow rate of 12 mL/min;

the first eluted compound was collected and evaporated to give the title compound Isomer 1 Intermediate 105 (34 mg); MS (ESI) m/z $[M+H]^+$ 643.2.

Intermediate 106

(S)-5-Bromo-3-chloro-2-nitro-N-(oxetan-2-ylmethyl)aniline

DIPEA (15.44 mL, 88.43 mmol) and 5-bromo-1-chloro-3-fluoro-2-nitrobenzene (7.5 g, 29.48 mmol) were added dropwise to a solution of (S)-oxetan-2-ylmethanamine (2.57 g, 29.48 mmol) in THE (200 mL), and the reaction mixture was stirred at 60° C. for 3 h. The reaction mixture was diluted with EtOAc (300 mL) and washed with sat brine (4×300 mL). The organic layer was dried over $Na_2SO_4$, filtered and evaporated at reduced pressure. The crude product was purified by flash chromatography on silica (0-50% EtOAc in petroleum ether) to give the title compound (9.00 g, 95%) as a yellow oil; MS (ESI) m/z $[M+H]^+$ 321/323.

Intermediate 107

(S)-5-Bromo-3-chloro-$N^1$-(oxetan-2-ylmethyl)benzene-1,2-diamine

Fe(s) (24.66 g, 441.60 mmol) was added to a mixture of (S)-5-bromo-3-chloro-2-nitro-N-(oxetan-2-ylmethyl)aniline Intermediate 106 (14.2 g, 44.16 mmol) and $NH_4Cl$ (23.62 g, 441.60 mmol) in MeOH (400 mL) and water (100 mL) at 20° C., and the reaction mixture was stirred at 60° C. for 6 h. The reaction mixture was filtered and the precipitate was washed with MeOH (4×100 mL). The combined filtrate was concentrated at reduced pressure and the crude product was diluted with EtOAc (500 mL). The organic layer was washed sequentially with water (500 mL) and sat brine (500 mL), dried over $Na_2SO_4$, filtered and concentrated at reduced pressure. The crude product was purified by flash chromatography on silica (30-50% EtOAc in petroleum ether) to give the title compound (12.0 g, 93%) as a white solid; MS (ESI) m/z $[M+H]^+$ 292/291.

Intermediate 108

Methyl (S)-4-amino-3-chloro-5-((oxetan-2-ylmethyl)amino)benzoate

A mixture of (S)-5-bromo-3-chloro-$N^1$-(oxetan-2-ylmethyl)benzene-1,2-diamine Intermediate 107 (1.5 g, 5.14 mmol), Pd(dppf)$Cl_2$·DCM (0.38 g, 0.51 mmol) and DIPEA (8.99 mL, 51.45 mmol) in MeOH (300 mL) was stirred under an atmosphere of CO(g) at 60 atm and 120° C. for 30 h. The solvent was removed at reduced pressure and the crude product was purified by flash chromatography on silica (20-25% EtOAc in petroleum ether) to give the title compound (1.0 g, 72%) as a white solid; MS (ESI) m/z $[M+H]^+$ 271.

Intermediate 109

Methyl (S)-4-chloro-2-(chloromethyl)-1-(oxetan-2-ylmethyl)-1H-benzo[d]imidazole-6-carboxylate pTsOH (0.357 g, 1.88 mmol) was added to a solution of methyl (S)-4-amino-3-chloro-5-((oxetan-2-ylmethyl)amino) benzoate Intermediate 108 (5.08 g, 18.77 mmol) and 2-chloro-1,1,1-trimethoxyethane (3.77 g, 24.40 mmol) in MeCN (20 mL) and the reaction mixture was stirred at 50° C. for 30 min. 2-Chloro-1,1,1-trimethoxyethane (1.16 g, 7.51 mmol) was added and the reaction mixture was stirred at 50° C. for 20 min. The reaction mixture was diluted with EtOAc (10 mL) and washed with $NaHCO_3$ (aq, 2×3 mL). The organic layer was dried over $MgSO_4$, filtered and concentrated at reduced pressure. The crude compound was purified by flash chromatography on silica (50-100% EtOAc in heptane) to give the title compound (5.30 g, 86%); MS (ESI) m/z $[M+H]^+$ 329.1.

Intermediate 110

Methyl 4-chloro-2-(((4aRS,7aSR)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylate rac-(4aR,7aS)-1-(6-((4-Chloro-2-fluorobenzyl)oxy)pyridin-2-yl)octahydrofuro[3,4-b]pyrazine dihydrochloride Intermediate 79 (300 mg, 687 μmol), methyl (S)-4-chloro-2-(chloromethyl)-1-(oxetan-2-ylmethyl)-1H-benzo[d]imidazole-6-carboxylate Intermediate 109 (226 mg, 687 μmol), DIPEA (600 μL, 3.43 mmol) and NaI (21 mg, 137 μmol) were mixed in dry MeCN (5 mL) and the reaction mixture was stirred at 40° C. for 1 h. The reaction mixture was diluted with water and extracted with EtOAc (3×5 mL). The combined organic layer was dried over $Na_2SO_4$, filtered and concentrated at reduced pressure, and the residue was purified by preparative HPLC, PrepMethod E (gradient: 15-35%) to give the title compound (87 mg, 18%); MS (ESI) m/z $[M+H]^+$ 658.2.

Intermediate 111

Methyl 4-chloro-2-(((4aR*,7aS*)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylate Isomer 1

Intermediate 112

Methyl 4-chloro-2-(((4aR*,7aS*)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylate Isomer 2

The stereoisomers of methyl 4-chloro-2-(((4aRS,7aSR)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylate Intermediate 110 were separated by chiral chromatography on a YMC Chiral ART column (250×20 mm, 5 μm), eluted with hexane:IPA:MeOH (70:15:15), at a flow rate of 12 mL/min;

the first eluted compound was collected and evaporated to give the title compound Isomer 1 Intermediate 111 (40 mg); MS (ESI) m/z $[M+H]^+$ 656.2; and the second eluted compound was collected and evaporated to give the title compound Isomer 2 Intermediate 112 (37 mg); MS (ESI) m/z $[M+H]^+$ 658.0.

Intermediate 113

Methyl 3-fluoro-5-((2-(2-methyl-1H-imidazol-1-yl)ethyl)amino)-4-nitrobenzoate

A mixture of methyl 3,5-difluoro-4-nitrobenzoate (3.0 g, 13.82 mmol), 2-(2-methyl-1H-imidazol-1-yl)ethan-1-amine (1.73 g, 13.82 mmol) and DIPEA (8.93 g, 69.08 mmol) in THE (15 mL) was stirred at 45° C. for 16 h, and then cooled to rt. The mixture was diluted with water and extracted with MTBE. The combined organic layer was washed with brine, dried over anhydrous $Na_2SO_4$, and filtered. The filtrate was concentrated at reduced pressure to give the title compound (3.5 g, 57%); MS (ESI) m/z $[M+H]^+$ 323.0.

Intermediate 114

Methyl 4-amino-3-fluoro-5-((2-(2-methyl-1H-imidazol-1-yl)ethyl)amino)benzoate

Methyl 3-fluoro-5-(2-(2-methyl-1H-imidazol-1-yl)ethyl) amino-4-nitrobenzoate Intermediate 113 (3.5 g, 10.9 mmol) was dissolved in MeOH (15 mL) and treated with Pd/C (10%, 350 mg). The reaction mixture was hydrogenated under an atmosphere of $H_2$(g) at ambient pressure and temperature until the reaction was complete. The reaction mixture was filtered, and the filtrate was collected and concentrated in vacuo and the residue was purified by flash chromatography on silica (0-95% MeOH in MeCN) to give the title compound (1.4 g, 44%); $^1H$ NMR (400 MHz, DMSO-$d_6$) δ 7.19 (t, 1H), 7.08-6.97 (m, 1H), 6.89 (d, 1H), 6.81 (d, 1H), 5.39 (s, 2H), 5.29 (d, 1H), 4.14-4.04 (m, 2H), 3.75 (d, 3H), 3.42 (q, 2H), 2.27 (d, 3H).

Intermediate 115

Methyl 4-fluoro-2-(hydroxymethyl)-1-(2-(2-methyl-1H-imidazol-1-yl)ethyl)-1H-benzo[d]imidazole-6-carboxylate 2,2,2-Triethoxyethan-1-ol (2.56 g, 14.37 mmol) and pTsOH hydrate (91 mg, 479 μmol) were added to a solution of methyl 4-amino-3-fluoro-5-(2-(2-methyl-1H-imidazol-1-yl)ethyl)aminobenzoate Intermediate 114 (1.4 g, 4.79 mmol) in THE (80 mL), and the reaction mixture was stirred at 50° C. overnight. The reaction mixture was poured into an excessive amount of water and extracted with EtOAc (×3). The combined organic layer was washed with brine and concentrated at reduced pressure to give the title compound (1.5 g, 94%); MS (ESI) m/z $[M+H]^+$ 333.2.

Intermediate 116

Methyl 2-(chloromethyl)-4-fluoro-1-(2-(2-methyl-1H-imidazol-1-yl)ethyl)-1H-benzo[d]imidazole-6-carboxylate Thionyl chloride (2.68 g, 22.56 mmol) was added dropwise to a solution of methyl 4-fluoro-2-(hydroxymethyl)-1-(2-(2-methyl-1H-imidazol-1-yl)ethyl)-1H-benzo[d]imidazole-6-carboxylate Intermediate 115 (1.5 g, 4.51 mmol) in DCM (15 mL) and the reaction mixture was stirred at 50° C. for 2 h. The reaction mixture was concentrated at reduced pressure, and the residue was suspended in dry $Et_2O$ (250 mL) and filtered, to give the dihydrochloride of the title compound (1.0 g, 63%); MS (ESI) m/z $[M+H]^+$ 351.0.

Intermediate 117 rac-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-4-fluoro-1-(2-(2-methyl-1H-imidazol-1-yl)ethyl)-1H-benzo[d]imidazole-6-carboxylate rac-(4aR,7aS)-1-(6-((4-Chloro-2-fluorobenzyl)oxy)pyridin-2-yl)octahydrofuro[3,4-b]pyrazine dihydrochloride Intermediate 79 (509 mg, 1.2 mmol), methyl 2-(chloromethyl)-4-fluoro-1-(2-(2-methyl-1H-imidazol-1-yl)ethyl)-1H-benzo[d]imidazole-6-carboxylate dihydrochloride Intermediate 116 (700 mg, 1.6 mmol) and DIPEA (1.26 mL, 7.21 mmol) were mixed in MeCN (5 mL) and the reaction mixture was stirred at 40° C. for 16 h. The reaction mixture was diluted with $H_2O$ (10 mL) and extracted with EtOAc (3×5 mL). The combined organic layer was dried over $Na_2SO_4$, filtered and evaporated at reduced pressure and the residue was purified by preparative HPLC, PrepMethod E (gradient: 60-95%) to give the title compound (125 mg, 16%); MS (ESI) m/z $[M+H]^+$ 678.2.

Intermediate 118 rel-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-4-fluoro-1-(2-(2-methyl-1H-imidazol-1-yl)ethyl)-1H-benzo[d]imidazole-6-carboxylate Isomer 1

The stereoisomers of rac-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-4-fluoro-1-(2-(2-methyl-1H-imidazol-1-yl)ethyl)-1H-benzo[d]imidazole-6-carboxylate Intermediate 117 were separated by chiral chromatography on a YMC Chiral ART column (250×20 mm, 5 μm), eluted with hexane:IPA:MeOH (50:25:25), at a flow rate of 12 mL/min;

The first eluted compound was collected and evaporated to give the title compound, Isomer 1 Intermediate 118 (47 mg, 38%); MS (ESI) m/z $[M+H]^+$ 678.0.

Intermediate 119

Methyl 3-chloro-5-((2-(2-methyl-1H-imidazol-1-yl)ethyl)amino)-4-nitrobenzoate

A solution of 2-(2-methyl-1H-imidazol-1-yl)ethan-1-amine dihydrochloride (2.63 g, 13.28 mmol) in dry DMF (50 mL) was slowly added to a mixture of methyl 3-chloro-5-fluoro-4-nitrobenzoate (3.1 g, 13.28 mmol) and DIPEA (6.01 g, 46.49 mmol) in dry DMF (15 mL), and the reaction mixture was stirred at 60° C. for 16 h. The reaction mixture was poured into water (150 mL) and extracted with DCM (3×60 mL). The combined organic layer was dried over $Na_2SO_4$, filtered, and concentrated at reduced pressure to give the title compound (3.46 g, 77% yield) as an orange oil; MS (ESI) m/z $[M+H]^+$ 339.2.

Intermediate 120

Methyl 4-amino-3-chloro-5-((2-(2-methyl-1H-imidazol-1-yl)ethyl)amino)benzoate

Pt/C (10%, 0.6 g) was added to a solution of methyl 3-chloro-5-(2-(2-methyl-1H-imidazol-1-yl)ethyl)amino-4-nitrobenzoate Intermediate 119 (3.46 g, 10.2 mmol) in MeOH (100 mL), and the reaction mixture was stirred under an atmosphere of $H_2$(g) at 1 atm and rt for 5 days. The reaction mixture was filtered through a pad of celite, and the filtrate was concentrated in vacuo. The residue was purified by chromatography on silica (10% MeOH in $CHCl_3$) to give the title compound (3 g, 96%) as yellow solid. $^1H$ NMR (400 MHz, $CDCl_3$) δ 7.58 (d, 1H), 7.24 (s, 2H), 6.87 (s, 1H), 6.82-6.73 (m, 1H), 4.33 (s, 2H), 4.08 (t, 2H), 3.85 (s, 3H), 3.69 (s, 1H), 3.53 (s, 2H), 2.29 (s, 2H).

Intermediate 121

Methyl 4-chloro-2-(hydroxymethyl)-1-(2-(2-methyl-1H-imidazol-1-yl)ethyl)-1H-benzo[d]imidazole-6-carboxylate 2,2,2-Triethoxyethan-1-ol (1.85 g, 10.36 mmol) and pTsOH (59 mg, 345 μmol) were added to a solution of methyl 4-amino-3-chloro-5-(2-(2-methyl-1H-imidazol-1-yl)ethyl)aminobenzoate Intermediate 120 (1.07 g, 3.45 mmol) in MeCN (7 mL) and the reaction mixture was stirred at 60° C. for 16 h. The reaction mixture was allowed to cool to rt and then concentrated in vacuo. The residue was diluted with water (50 mL), and the pH was adjusted to 7 with sat $Na_2CO_3$ (aq). The mixture was extracted with EtOAc (3×50 mL) and the combined organic layer was washed with brine (50 mL) and water (50 mL), dried over $Na_2SO_4$, filtered, and concentrated in vacuo to give the crude title compound (1.14 g); MS (ESI) m/z $[M+H]^+$ 349.2.

Intermediate 122

Methyl 4-chloro-2-(chloromethyl)-1-(2-(2-methyl-1H-imidazol-1-yl)ethyl)-1H-benzo[d]imidazole-6-carboxylate A catalytic amount of DMF followed by thionyl chloride (3.89 g, 32.68 mmol) were added dropwise to a vigorously stirred solution of methyl 4-chloro-2-(hydroxymethyl)-1-(2-(2-methyl-1H-imidazol-1-yl)ethyl)-1H-benzo[d]imidazole-6-carboxylate Intermediate 121 (1.14 g, 3.27 mmol) in DCM (15 mL) and the reaction mixture was stirred at 40° C. for 16 h. The reaction mixture was concentrated in vacuo to give the title compound (0.95 g, 79%) as yellow solid; MS (ESI) m/z $[M+H]^+$ 367.0.

Intermediate 123 rac-Methyl 4-chloro-2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate rac-(4aR,7aS)-1-(6-((4-Chloro-2-fluorobenzyl)oxy)pyridin-2-yl)octahydrofuro[3,4-b]pyrazine dihydrochloride Intermediate 79 (532 mg, 1.22 mmol), methyl 4-chloro-2-(chloromethyl)-1-(2-(2-methyl-1H-imidazol-1-yl)ethyl)-1H-benzo[d]imidazole-6-carboxylate Intermediate 122 (895 mg, 2.44 mmol), DIPEA (1.19 mL, 6.83 mmol) and NaI (15 mg, 98 μmol) were mixed in MeCN (5 mL), and the reaction mixture is stirred at 40° C. 16 h. The reaction mixture was diluted with $H_2O$ (10 mL) and extracted with EtOAc (3×15 mL). The combined organic layer was dried over $Na_2SO_4$, filtered and evaporated in vacuo and the residue was purified by preparative HPLC, PrepMethod E (gradient: 0-55%) to give the title compound (20 mg, 1.2%); MS (ESI) m/z $[M+H]^+$ 367.0.

Intermediate 124 rel-Methyl 4-chloro-2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate Isomer 1

The stereoisomers of rac-methyl 4-chloro-2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate Intermediate 123 were separated by chiral chromatography on a ChiralArt YMC column (250×20 mm, 5 μm), eluted with IPA:MeOH (50:50), at a flow rate of 11 mL/min the first eluted compound was collected and evaporated to give the title compound, Isomer 1 Intermediate 124 (7.2 mg); MS (ESI) m/z $[M+H]^+$ 697.2.

Intermediate 125

Methyl 3-((2-(2-methyl-1H-imidazol-1-yl)ethyl)amino)-4-nitrobenzoate

A mixture of 2-(2-methyl-1H-imidazol-1-yl)ethan-1-amine (4.62 g, 36.91 mmol), methyl 3-fluoro-4-nitrobenzoate (7.0 g, 35.15 mmol) and $Cs_2CO_3$ (12.6 g, 38.67 mmol) in THE (20 mL) was stirred at 45° C. for 2 h and then cooled to rt. The reaction mixture was diluted with water (30 mL) and extracted with MTBE (3×5 mL). The combined organic layer was washed with brine, dried over $Na_2SO_4$, filtered and concentrated at reduced pressure to give the crude title compound (9.3 g, 83%); MS (ESI) m/z $[M+H]^+$ 305.0.

Intermediate 126

Methyl 4-amino-3-((2-(2-methyl-1H-imidazol-1-yl)ethyl)amino)benzoate

Methyl 3-((2-(2-methyl-1H-imidazol-1-yl)ethyl)amino)-4-nitrobenzoate Intermediate 125 (9.3 g, 29.0 mmol) was dissolved in THE (30 mL) and treated with 10% Pd/C (0.9 g) and the reaction mixture was hydrogenated under an atmosphere of $H_2$(g) at ambient pressure and temperature until complete reaction. The reaction mixture was filtered, the solids were washed with hot DMF (10 mL) and the filtrate was concentrated to dryness at reduced pressure. The crude residue was purified by chromatography (hexane: EtOAc, 1:1) to give the title compound (5.5 g, 59%); MS (ESI) m/z $[M+H]^+$ 275.2.

Intermediate 127 rac-Ethyl 2-((4aR,7aS)-4-(6-((4-chloro-2-fluorobenzyl)oxy)pyridin-2-yl)hexahydrofuro[3,4-b]pyrazin-1(2H)-yl)acetate rac-(4aR,7aS)-1-(6-((4-Chloro-2-fluorobenzyl)oxy)pyridin-2-yl)octahydrofuro[3,4-b]pyrazine dihydrochloride Intermediate 79 (1.0 g, 2.29 mmol), ethyl 2-bromoacetate (314 mg, 1.88 mmol), DIPEA (1.21 g, 9.39 mmol) and NaI (28 mg, 188 μmol) were mixed in MeCN (5 mL) and the reaction mixture was stirred at rt for 16 h. The reaction mixture was diluted with water and extracted with EtOAc. The organic layer was dried over $Na_2SO_4$, filtered and evaporated at reduced pressure to give the title compound (850 mg, 75%); MS (ESI) m/z $[M+H]^+$ 450.0.

Intermediate 128 rac-2-((4aR,7aS)-4-(6-((4-Chloro-2-fluorobenzyl)oxy)pyridin-2-yl)hexahydrofuro[3,4-b]pyrazin-1(2H)-yl)acetic acid NaOH (378 mg, 9.45 mmol) was added to a solution of rac-ethyl 2-((4aR,7aS)-4-(6-((4-chloro-2-fluorobenzyl)oxy)pyridin-2-yl)hexahydrofuro[3,4-b]pyrazin-1(2H)-yl)acetate Intermediate 127 (850 mg, 1.89 mmol) in MeOH:$H_2O$ (10:1, 5 mL) and the reaction mixture was stirred at rt for 16 h. The reaction mixture was concentrated at reduced pressure, and the residue was dissolved in DMSO (5 mL) and purified by preparative HPLC, PrepMethod E (gradient 0-55%) to give the title compound (360 mg, 51%); MS (ESI) m/z $[M+H]^+$ 422.1.

Intermediate 129 rac-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate Step a) rac-Methyl 4-(2-((4aR,7aS)-4-(6-((4-chloro-2-fluorobenzyl)oxy)pyridin-2-yl)hexahydrofuro[3,4-b]pyrazin-1(2H)-yl)acetamido)-3-((2-(2-methyl-1H-imidazol-1-yl)ethyl)amino)benzoate Methyl 4-amino-3-((2-(2-methyl-1H-imidazol-1-yl)ethyl)amino)benzoate Intermediate 126 (162 mg, 592 μmol) was added to a suspension of rac-2-((4aR,7aS)-4-(6-((4-chloro-2-fluorobenzyl)oxy)pyridin-2-yl)hexahydrofuro[3,4-b]pyrazin-1(2H)-yl)acetic acid Intermediate 128 (227 mg, 538 μmol), DIPEA (190 μL 1.08 mmol) and HATU (368 mg, 969 μmol) in DMF (3 mL) and the reaction mixture was stirred at rt overnight. The crude mixture was concentrated at reduced pressure and used in the next step without further purification Step b) rac-methyl-2-(((4aR,7aS)-4-(6-((4-chloro-2-fluorobenzyl)oxy)pyridin-2-yl)hexahydrofuro[3=b]pyrazin-1(2H)-ylmethyl)-1-(2-(2-methyl-1H-imidazol-1-yl)ethyl)-1H-benzo[d]imidazole-6-carboxylate Crude rac-methyl 4-(2-((4aR,7aS)-4-(6-((4-chloro-2-fluorobenzyl)oxy)pyridin-2-yl)hexahydrofuro[3,4-b]

pyrazin-1(2H)-yl)acetamido)-3-((2-(2-methyl-1H-imidazol-1-yl)ethyl)amino)benzoate Intermediate 129 Step a) (300 mg) was dissolved in AcOH (5 mL) and heated at 60° C. overnight. The reaction mixture was quenched with sat $NaHCO_3$ (aq) and extracted with EtOAc. The organic layer was washed with water, dried over $Na_2SO_4$, filtered and concentrated in vacuo and the residue was purified by preparative HPLC, PrepMethod N (gradient 10-40%) to give the title compound (18 mg, 11%); MS (ESI) m/z $[M+H]^+$ 660.3.

Intermediate 130 rel-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate, Isomer 1

Intermediate 131 rel-Methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate, Isomer 2

The stereoisomers of rac-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate Intermediate 129 were separated by chiral chromatography on a Chiralcel OJ-H1 Column (250×20 mm, 5 μm), eluted with IPA:MeOH (50:50), at a flow rate of 12 mL/min;

- the first eluted compound was collected and evaporated to give the title compound, Isomer 1 Intermediate 130 (5 mg, 28%); MS (ESI) m/z $[M+H]^+$ 660.2; and
- the second eluted compound was collected and evaporated to give the title compound, Isomer 2 Intermediate 131 (8 mg, 44%); MS (ESI) m/z $[M+H]^+$ 660.2.

EXAMPLES

Example 1 rac-2-(((1R,6S)-5-(6-((4-Cyano-2-fluorobenzyl)oxy)pyridin-2-yl)-2,5-diazabicyclo[4.2.0]octan-2-yl)methyl)-1-((1-methyl-1H-pyrazol-3-yl)methyl)-1H-benzo[d]imidazole-6-carboxylic acid

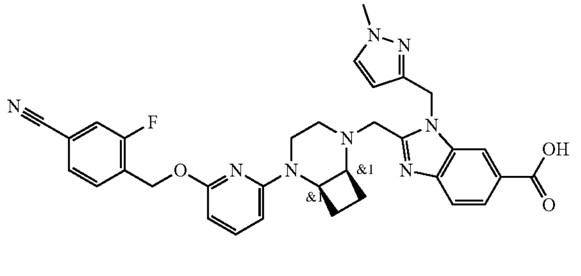 [SMILES: Cn1ccc(Cn2c(CN3CCN(c4cccc(OCc5ccc(C#N)cc5F)n4)[C@@H]4CC[C@@H]43)nc3ccc(C(=O)O)cc32)n1]

rac-Methyl 2-(((1R,6S)-5-(6-((4-cyano-2-fluorobenzyl)oxy)pyridin-2-yl)-2,5-diazabicyclo[4.2.0]octan-2-yl)methyl)-1-((1-methyl-1H-pyrazol-3-yl)methyl)-1H-benzo[d]imidazole-6-carboxylate Intermediate 10 (100 mg, 0.16 mmol) was added to a solution of 1,3,4,6,7,8-hexahydro-2H-pyrimido[1,2-a]pyrimidine (45 mg, 0.32 mmol) in water (0.6 mL) and MeCN (3 mL) and the reaction mixture was stirred at 20° C. for 3 h. The reaction mixture was quenched with sat brine (100 mL) and extracted with EtOAc (3×150 mL). The combined organic layer was dried over $Na_2SO_4$, filtered and concentrated in vacuo. The crude product was purified by preparative HPLC, PrepMethod C, (gradient: 38-53%), to give the TFA salt of the title compound (0.090 g, 74%) as a white solid; HRMS (ESI) m/z $[M+H]^+$ calcd for $C_{33}H_{32}FN_8O_3$: 607.2576, found: 607.2584; $^1H$ NMR (300 MHz, $CD_3OD$) δ 8.45 (dd, 1H), 8.18 (dd, 1H), 7.84 (dd, 1H), 7.68-7.38 (m, 5H), 6.35 (d, 1H), 6.17 (dd, 2H), 5.79 (d, 2H), 5.46 (t, 2H), 4.52 (d, 1H), 4.40 (q, 1H), 4.23 (d, 1H), 3.80 (s, 3H), 3.72-3.41 (m, 3H), 3.16-3.06 (m, 1H), 2.74 (t, 1H), 2.18 (td, 2H), 1.97 (q, 2H).

Example 2a 2-(((1R*,6S*)-5-(6-((4-Cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylic acid, Isomer 1

Isomer 1

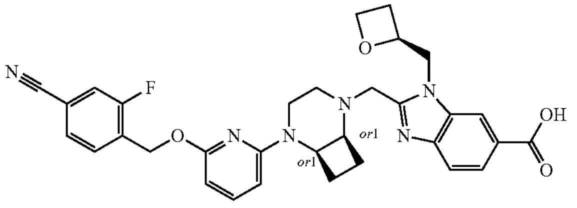

Methyl 2-(((1R*,6S*)-5-(6-((4-cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylate Isomer 1 Intermediate 12 (140 mg, 0.23 mmol) was added to a solution of 1,3,4,6,7,8-hexahydro-2H-pyrimido(1,2-a)-pyrimidine (39 mg, 0.28 mmol) in water (0.3 mL) and MeCN (1.2 mL) and the reaction mixture was stirred at 25° C. for 16 min. The solvent was evaporated under reduced pressure and the crude residue was purified by preparative HPLC, PrepMethod C, (gradient: 40-50%), followed by preparative SFC, PrepMethod D, to give the title compound Isomer 1 (11 mg) as a white solid; HRMS (ESI) m/z $[M+H]^+$ calcd for $C_{32}H_{32}FN_6O_4$: 583.2464, found: 583.2432; $^1H$ NMR (600 MHz, DMSO-$d_6$) δ 8.22 (s, 1H), 7.88 (dd, 1H), 7.82 (dd, 1H), 7.69 (dd, 1H), 7.63 (t, 1H), 7.61 (d, 1H), 7.46 (t, 1H), 6.14 (dd, 2H), 5.33-5.48 (m, 2H), 5.18 (qd, 1H), 4.82 (dd, 1H), 4.70 (dd, 1H), 4.46 (td, 1H), 4.35 (q, 1H), 4.23 (dt, 1H), 4.19 (d, 1H), 3.61-3.64 (m, 3H), 3.21-3.24 (m, 1H), 3.12 (td, 1H), 2.77 (dt, 1H), 2.33-2.39 (m, 1H), 2.25-2.29 (m, 1H), 2.03-2.08 (m, 1H), 1.96-2.02 (m, 1H), 1.68-1.76 (m, 1H), 1.58 (t, 1H).

Example 2b 2-(((1R*,6S*)-5-(6-((4-Cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylic acid, Isomer 2

Isomer 2

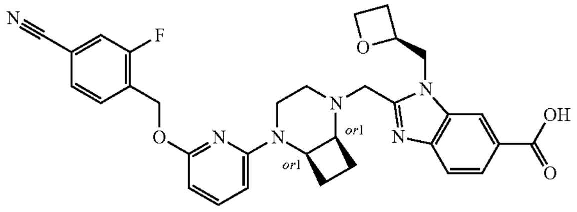

Methyl 2-(((1R*, 6S*)-5-(6-((4-cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylate Isomer 2 Intermediate 13 (180 mg, 0.30 mmol) was added to a solution of 1,3,4,6,7,8-hexahydro-2H-pyrimido(1,2-a)-pyrimidine (50 mg, 0.36 mmol), in water (0.4 mL) and MeCN (1.6 mL) and the reaction mixture was stirred at 20° C. for 16 h. The reaction mixture was concentrated under reduced pressure and the residue was purified by preparative HPLC, PrepMethod C, (gradient: 40-55%), to give the TFA salt of the title compound Isomer 2 (120 mg, 46%) as a white solid; HRMS (ESI) m/z $[M+H]^+$ calcd for $C_{32}H_{32}FN_6O_4$: 583.2464, found: 583.2476; $^1H$ NMR (300 MHz, $CD_3OD$) δ 8.58-8.52 (m, 1H), 8.22 (dd, 1H), 7.89 (d, 1H), 7.69-7.46 (m, 4H), 6.22 (dd, 2H), 5.49 (s, 2H), 5.29 (q, 1H), 5.02 (dd, 1H), 4.84-4.66 (m, 2H), 4.63-4.40 (m, 3H), 4.34 (d, 1H), 3.76 (s, 1H), 3.66 (d, 2H), 3.23 (d, 1H), 2.95-2.80 (m, 2H), 2.59 (dq, 1H), 2.25 (dq, 2H), 2.03 (q, 2H).

Example 3a 2-(((1R*,6R*)-5-(6-((4-Cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylic acid, Isomer 1

ISOMER 1

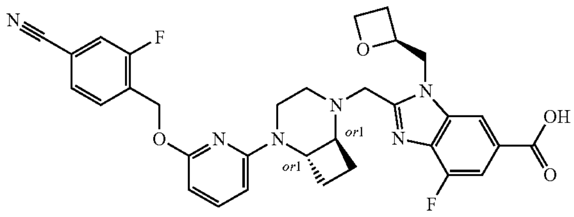

A solution of LiOH·$H_2O$ (12 mg, 0.29 mmol) in water (1 mL) was added to a solution of methyl 2-(((1R*,6R*)-5-(6-((4-cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylate, Isomer 1 Intermediate 21 (72 mg, 0.12 mmol) in THF (2 mL) and the reaction mixture was stirred at 0° C. to rt for 16 h. The reaction mixture was purified by preparative HPLC, PrepMethod E, (gradient: 20-45%) to give the lithium salt of the title compound (31 mg, 50%); HRMS (ESI) m/z $[M+H]^+$ calcd for $C_{32}H_{31}F_2N_6O_4$: 601.2370, found: 601.2374; $^1H$ NMR (600 MHz, DMSO-$d_6$) δ 7.92-7.80 (m, 2H), 7.72-7.59 (m, 2H), 7.48-7.38 (m, 2H), 6.24-6.09 (m, 2H), 5.41-5.29 (m, 2H), 5.10-5.14 (m, 1H), 4.75 (dd, 1H), 4.59 (dd, 1H), 4.46 (q, 1H), 4.32 (dt, 1H), 4.06-3.90 (m, 1H), 3.83-3.68 (m, 2H), 3.09-3.00 (m, 1H), 2.77 (p, 2H), 2.68 (p, 1H), 2.44-2.38 (m, 1H), 2.25 (p, 2H), 1.94 (dt, 1H), 1.60 (q, 1H), 1.21 (p, 1H).

Example 3b 2-(((1R*,6R*)-5-(6-((4-Cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylic acid, Isomer 2

ISOMER 2

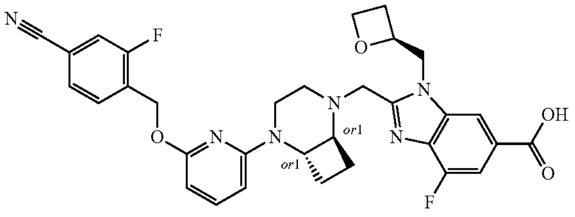

A solution of LiOH·$H_2O$ (11 mg, 0.26 mmol) in water (1 mL) was added to a solution of methyl 2-(((1R*,6R*)-5-(6-((4-cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylate, Isomer 2 Intermediate 22 (63 mg, 0.10 mmol) in THF (2 mL) and the reaction mixture was stirred at 0° C. to rt for 16 h. The reaction mixture was purified by preparative HPLC, PrepMethod E, (gradient: 20-45%) to give the lithium salt of the title compound (40 mg, 70%); HRMS (ESI) m/z $[M+H]^+$ calcd for $C_{32}H_{31}F_2N_6O_4$: 601.2370, found: 601.2366; $^1H$ NMR (600 MHz, DMSO-$d_6$) δ 7.92-7.80 (m, 2H), 7.72-7.56 (m, 2H), 7.50-7.36 (m, 2H), 6.17 (dd, 2H), 5.41-5.29 (m, 2H), 5.07 (dt, 1H), 4.80-4.58 (m, 2H), 4.53-4.29 (m, 2H), 3.95 (dd, 2H), 3.59 (d, 1H), 2.94 (d, 1H), 2.84-2.65 (m, 3H), 2.44-2.40 (m, 1H, partially overlapping with solvent), 2.35-2.23 (m, 3H), 1.97 (q, 1H), 1.78 (q, 1H), 1.43 (p, 1H).

Example 4a 2-(((1R*,6R*)-5-(6-((4-Cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylic acid, Isomer 1

ISOMER 1

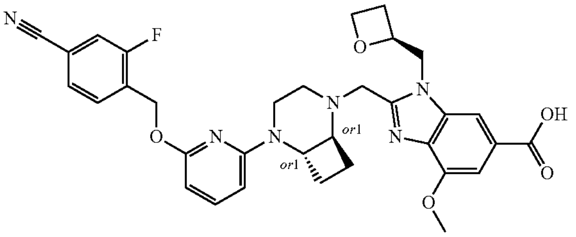

A solution of LiOH·$H_2O$ (13 mg, 0.30 mmol) in water (1 mL) was added to a solution of methyl 2-(((1R*,6R*)-5-(6-((4-cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylate, Isomer 1 Intermediate 27 (74 mg, 0.12 mmol) in THE (2 mL) the reaction mixture was stirred at 0° C. to rt for 16 h. The reaction mixture was purified by preparative HPLC, Prep-Method E, (gradient 0-15%) to give the lithium salt of the title compound (42 mg, 63%); HRMS (ESI) m/z $[M+H]^+$ calcd for $C_{33}H_{34}FN_6O_5$: 613.2568, found: 613.2574; $^1H$ NMR (600 MHz, DMSO-$d_6$) δ 7.85 (dd, 1H), 7.68 (dd, 1H), 7.66-7.55 (m, 2H), 7.44 (t, 1H), 7.28 (d, 1H), 6.16 (dd, 2H), 5.43-5.30 (m, 2H), 5.10 (dt, 1H), 4.67 (dd, 4H), 3.98 (d, 1H), 3.87 (s, 3H), 3.80-3.64 (m, 2H), 3.01 (d, 1H), 2.82-2.71 (m, 3H), 2.71-2.61 (m, 1H), 2.35-2.16 (m, 3H), 1.96-1.91 (m, 1H), 1.61 (q, 1H), 1.26-1.20 (m, 1H).

Example 4b 2-(((1R*,6R*)-5-(6-((4-Cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylic acid, Isomer 2

ISOMER 2

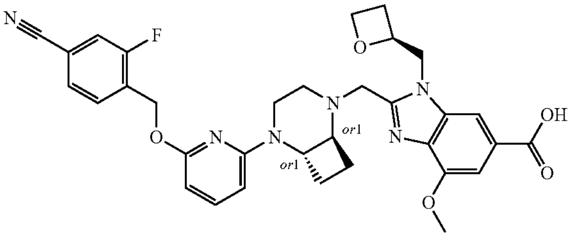

A solution of LiOH·$H_2O$ (11 mg, 0.30 mmol) in water (1 mL) was added to a solution of methyl 2-(((1R*,6R*)-5-(6-((4-cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylate, Isomer 2 Intermediate 28 (64 mg, 0.10 mmol) in THE (2 mL) the reaction mixture was stirred at 0° C. to rt for 16 h. The reaction mixture was purified by preparative HPLC, Prep-Method E, (gradient 0-15%) to give the lithium salt of the title compound (30 mg, 57%); HRMS (ESI) m/z $[M+H]^+$ calcd for $C_{33}H_{34}FN_6O_5$: 613.2568, found: 613.2568; $^1H$ NMR (600 MHz, DMSO-$d_6$) δ 7.86 (dd, 1H), 7.68 (dd, 1H), 7.64-7.57 (m, 2H), 7.44 (t, 1H), 7.29 (s, 1H), 6.17 (dd, 2H), 5.42-5.26 (m, 2H), 5.05 (dd, 1H), 4.72-4.52 (m, 2H), 4.51-4.30 (m, 2H), 4.01-3.80 (m, 6H), 3.53 (d, 1H), 2.97-2.63 (m, 4H), 2.35-2.20 (m, 3H), 2.00-1.94 (m, 1H), 1.77 (q, 1H), 1.46-1.40 (m, 1H).

Examples 5 to 11

The following Examples 5 to 11 were prepared as described in General Synthesis Scheme 3 and General Preparation Method E or F from appropriate Intermediates (SM 3) as described below.

General Synthesis Scheme 3

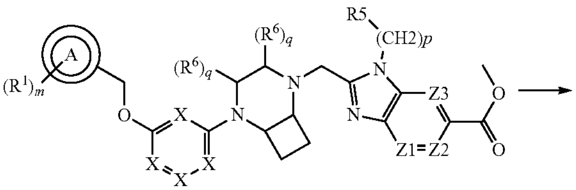

SM 3

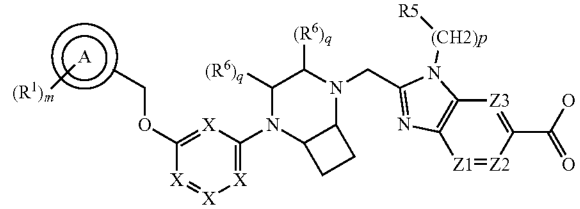

Preparation Method E: LiOH·$H_2O$ (2.5 eq) was added to a solution of SM 3 (1 eq) in a mixture of THF:$H_2O$ (2:1) and the reaction mixture was stirred at rt for 16 h. The reaction mixture was optionally worked up by acidifying the reaction mixture to pH 5-6 using $NaHSO_4$ (aq) solution, followed by extraction with EtOAc, and then drying, filtering and concentrating the organic layer at reduced pressure, or the reaction mixture was concentrated at reduced pressure. The crude product was then purified by preparative HPLC as described below.

Preparation Method F: 1,3,4,6,7,8-Hexahydro-2H-pyrimido[1,2-a]pyrimidine (1.2 eq) was added to a solution of SM 3 (1 eq) in a mixture of MeCN/$H_2O$ (3:1) and the reaction mixture was stirred at rt for 2-16 h. The pH of the reaction mixture was adjusted to 7 with 2 M HCl (aq) solution or 0.5 M citric acid (aq) solution. The reaction mixture was optionally extracted with EtOAc, dried, filtered and concentrated at reduced pressure and the crude product was purified by preparative HPLC as described below or the reaction mixture was concentrated and the crude product was purified by preparative HPLC as described below.

Example 5a 2-(((1R*,6R*)-5-(6-((4-Chloro-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylic acid, Isomer 1

Isomer 1

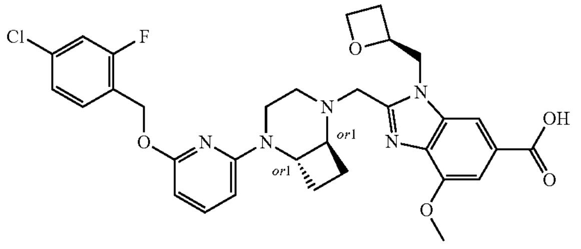

The title compound was prepared from SM 3 Intermediate 48 Isomer 1 (111 mg, 0.17 mmol) as described in Preparation Method E. The reaction mixture was concentrated and purified by preparative HPLC, PrepMethod E (30-50%) to give the lithium salt of the title compound (80 mg, 76%); HRMS (ESI) m/z $[M+H]^+$ calcd for $C_{32}H_{34}ClFN_5O_5$: 622.2228, found: 622.2250; $^1H$ NMR (600 MHz, DMSO-$d_6$) δ 1.25 (dt, 1H), 1.63 (dd, 1H), 1.97 (qd, 1H), 2.19-2.44 (m, partly overlapping with solvent), 2.61-2.71 (m, 1H), 2.78 (ddt, 2H), 3.03 (dt, 1H), 3.65-3.78 (m, 2H), 3.87 (s, 3H), 4.03 (d, 1H), 4.30 (dt, 1H), 4.45 (td, 1H), 4.53 (dd, 1H), 4.67 (dd, 1H), 5.11 (qd, 1H), 5.25 (d, 2H), 6.13 (dd, 2H), 7.22-7.33 (m, 2H), 7.38-7.52 (m, 3H), 7.61 (s, 1H).

Example 5b 2-(((1R*,6R*)-5-(6-((4-Chloro-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylic acid, Isomer 2

Isomer 2

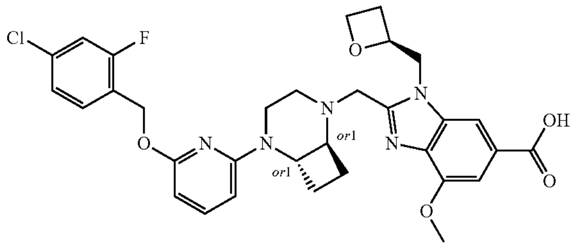

The title compound was prepared from SM 3 Intermediate 49 (101 mg, 0.16 mmol) as described in Preparation Method E. The reaction mixture was concentrated and purified by preparative HPLC, PrepMethod E (30-50%) to give the lithium salt of the title compound (74 mg, 73%); HRMS (ESI) m/z $[M+H]^+$ calcd for $C_{32}H_{34}ClFN_5O_5$: 622.2228, found: 622.2240; 1H NMR (600 MHz, DMSO-$d_6$) δ 1.46 (td, 1H), 1.79 (dd, 1H), 2.00 (qd, 1H), 2.21-2.40 (m, 4H), 2.63-2.88 (m, 3H), 2.93 (dt, 1H), 3.53 (d, 1H), 3.87 (s, 3H), 3.91 (d, 1H), 3.98-4.05 (m, 1H), 4.35 (dt, 1H), 4.42-4.52 (m, 1H), 4.56 (dd, 1H), 4.67 (dd, 1H), 5.06 (qd, 1H), 5.20-5.31 (m, 2H), 6.14 (dd, 2H), 7.21-7.33 (m, 2H), 7.39-7.52 (m, 3H), 7.59 (s, 1H).

Example 6a rel-4-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 1

Isomer 1

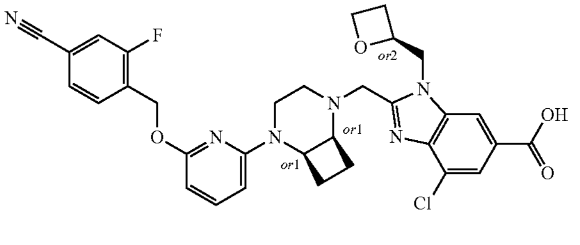

The title compound was prepared from SM 3 Intermediate 38 Isomer 1 (50 mg, 0.08 mmol) as described in Preparation Method F. The crude product was purified by preparative HPLC, PrepMethod I (24-54%) to give the title compound (24 mg, 36%); HRMS (ESI) m/z $[M+H]^+$ calcd for $C_{32}H_{31}ClFN_6O_4$: 617.2074, found: 617.2084; $^1H$ NMR (400 MHz, $CD_3OD$) δ 2.11-2.18 (m, 4H), 2.46-2.51 (m, 1H), 2.79-2.83 (m, 1H), 3.15-3.25 (m, 1H), 3.45-3.65 (m, 2H), 3.75-3.90 (m, 1H), 4.00-4.15 (m, 1H), 4.40-4.48 (m, 3H), 4.62-4.75 (m, 2H), 4.82 (d, 2H), 5.20-5.30 (m, 1H), 5.49 (s, 2H), 6.19 (d, 1H), 6.28 (d, 1H), 7.48-7.69 (m, 4H), 8.04 (d, 1H), 8.34 (d, 1H).

Example 6b rel-4-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 2

Isomer 2

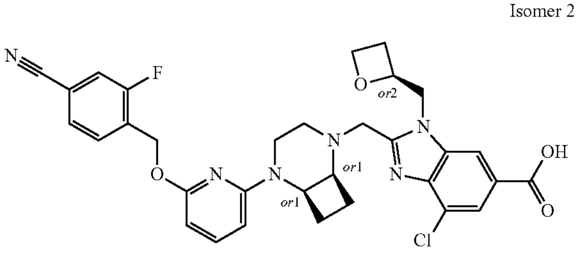

The title compound was prepared from SM 3 Intermediate 39 Isomer 2 (50 mg, 0.08 mmol) as described in Preparation Method F. The crude product was purified by preparative HPLC, PrepMethod I (22-52%) to give the title compound (24 mg, 40%); HRMS (ESI) m/z $[M+H]^+$ calcd for $C_{32}H_{31}ClFN_6O_4$: 617.2074, found: 617.2068; $^1H$ NMR (300 MHz, $CD_3OD$) δ 2.05-2.25 (m, 4H), 2.40-2.55 (m, 1H), 2.75-2.85 (m, 1H), 3.05-3.20 (m, 1H), 3.40-3.50 (m, 1H), 3.55-3.65 (m, 1H), 3.70-3.85 (m, 1H), 3.90-4.05 (m, 1H), 4.35-4.50 (m, 3H), 4.60-4.75 (m, 2H), 4.83 (t, 2H), 5.20-

5.30 (m, 1H), 5.49 (s, 2H), 6.19 (d, 1H), 6.26 (d, 1H), 7.46-7.70 (m, 4H), 8.03 (d, 1H), 8.34 (d, 1H).

Example 6c rel-4-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 3

Isomer 3

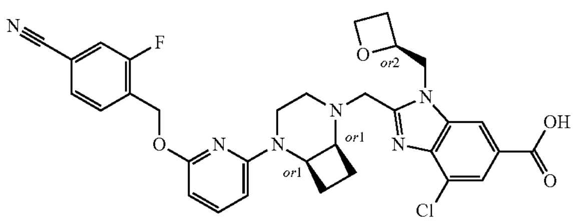

The title compound was prepared from SM 3 Intermediate 40 Isomer 3 (66 mg, 0.10 mmol) as described in Preparation Method F. The crude product was purified by preparative HPLC, PrepMethod I (22-52%) to give the title compound (38 mg, 44%); HRMS (ESI) m/z $[M+H]^+$ calcd for $C_{32}H_{31}ClFN_6O_4$: 617.2074, found: 617.2074; $^1H$ NMR (300 MHz, $CD_3OD$) δ 2.05-2.20 (m, 4H), 2.45-2.60 (m, 1H), 2.75-2.90 (m, 1H), 3.10-3.20 (m, 1H), 3.30-3.78 (m, 3H), 3.95-4.05 (m, 1H), 4.40-4.55 (m, 3H), 4.62-4.78 (m, 2H), 4.85-4.95 (m, 2H), 5.25 (d, 1H), 5.47 (s, 2H), 6.18 (d, 1H), 6.26 (d, 1H), 7.50-7.70 (m, 4H), 8.02 (d, 1H), 8.32 (d, 1H).

Example 6d rel-4-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 4

Isomer 4

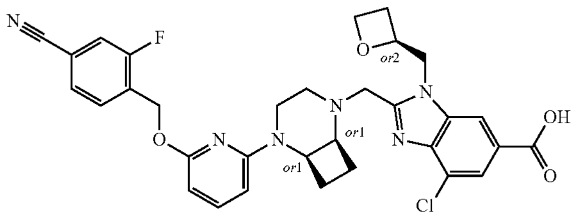

The title compound was prepared from SM 3 Intermediate 41 Isomer 4 (70 mg, 0.11 mmol) as described in Preparation Method F. The crude product was purified by preparative HPLC, PrepMethod I (24-54%) to give the title compound (38 mg, 46%); HRMS (ESI) m/z $[M+H]^+$ calcd for $C_{32}H_{31}ClFN_6O_4$: 617.2074, found: 617.2078; $^1H$ NMR (300 MHz, $CD_3OD$) δ 2.05-2.25 (m, 4H), 2.55 (t, 1H), 2.75-2.85 (m, 1H), 3.10-3.20 (m, 1H), 3.35-3.45 (m, 1H), 3.60-3.80 (m, 2H), 3.90-4.00 (m, 1H), 4.37 (d, 1H), 4.46-4.57 (m, 2H), 4.69 (dd, 3H), 4.95-5.00 (m, 1H), 5.26 (td, 1H), 5.49 (s, 2H), 6.20 (d, 1H), 6.27 (d, 1H), 7.50-7.68 (m, 4H), 8.03 (d, 1H), 8.34 (d, 1H).

Example 7a rel-5-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 1

Isomer 1

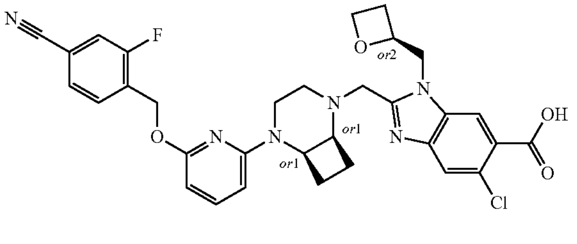

The title compound was prepared from SM 3 Intermediate 42 Isomer 1 (50 mg, 0.08 mmol) as described in Preparation Method F. The crude product was purified by preparative HPLC, PrepMethod I (21-51%) to give the title compound (39 mg, 80%); HRMS (ESI) m/z $[M+H]^+$ calcd for $C_{32}H_{31}ClFN_6O_4$: 617.2074, found: 617.2094; $^1H$ NMR (300 MHz, $CD_3OD$) δ 1.66 (t, 1H), 1.79 (dd, 1H), 1.98-2.22 (m, 2H), 2.29-2.54 (m, 2H), 2.69-2.87 (m, 2H), 3.18-3.31 (m, partly overlapping with solvent), 3.65 (d, 1H), 3.77 (d, 1H), 4.23-4.46 (m, 3H), 4.57-4.67 (m, 1H), 4.75 (dd, 1H), 4.92-5.00 (m, 1H), 5.29 (d, 1H), 5.47 (s, 2H), 6.14 (dd, 2H), 7.44 (t, 1H), 7.50-7.69 (m, 3H), 7.73 (s, 1H), 8.12 (s, 1H).

Example 7b rel-5-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 2

Isomer 2

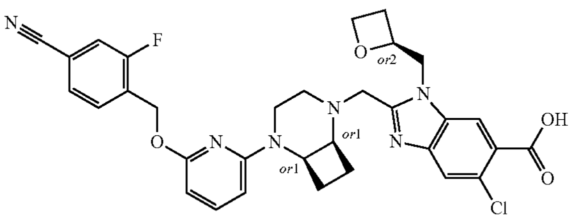

The title compound was prepared from SM 3 Intermediate 43 Isomer 2 (80 mg, 0.13 mmol) as described in Preparation Method F. The crude product was purified by preparative HPLC, PrepMethod I (21-51%) to give the title compound (70 mg, 89%); HRMS (ESI) m/z $[M+H]^+$ calcd for $C_{32}H_{31}ClFN_6O_4$: 617.2074, found: 617.2062, $^1H$ NMR (300 MHz, $CD_3OD$) δ 1.88 (t, 2H), 2.12 (dd, 1H), 2.19-2.38 (m, 2H), 2.51-2.64 (m, 1H), 2.69-2.87 (m, 2H), 3.18-3.28 (m, partly overlapping with solvent), 3.65 (dd, 2H), 4.31 (d, 1H), 4.39-4.74 (m, 4H), 5.06 (dd, 1H), 5.27 (td, 1H), 5.47 (s, 2H), 6.15 (dd, 2H), 7.45 (t, 1H), 7.50-7.68 (m, 3H), 7.70 (s, 1H), 8.08 (s, 1H).

Example 7c rel-5-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 4

Isomer 4

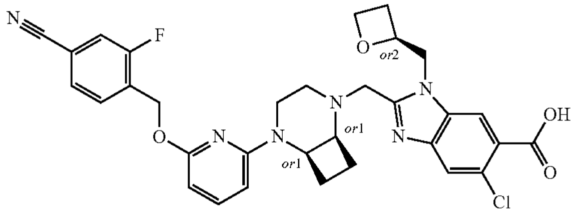

The title compound was prepared from SM 3 Intermediate 44 Isomer 3 (55 mg, 0.09 mmol) as described in Preparation Method F. The crude product was purified by preparative HPLC, PrepMethod I (21-51%) to give the title compound (47 mg, 87%); HRMS (ESI) m/z $[M+H]^+$ calcd for $C_{32}H_{31}ClFN_6O_4$: 617.2074, found: 617.2074; $^1H$ NMR (400 MHz, $CD_3OD$) δ 1.81-1.96 (m, 2H), 2.10-2.20 (m, 1H), 2.22 (d, 1H), 2.28-2.37 (m, 1H), 2.57 (d, 1H), 2.70-2.86 (m, 2H), 3.23-3.35 (m, 2H), 3.60-3.70 (m, 2H), 4.31 (d, 1H), 4.46 (d, 1H), 4.51-4.57 (m, 1H), 4.59-4.76 (m, 2H), 5.03-5.10 (m, 1H), 5.27 (d, 1H), 5.48 (s, 2H), 6.16 (d, 2H), 7.45 (t, 1H), 7.54-7.66 (m, 3H), 7.70 (d, 1H), 8.04 (s, 1H).

Example 8a rel-7-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 1

Isomer 1

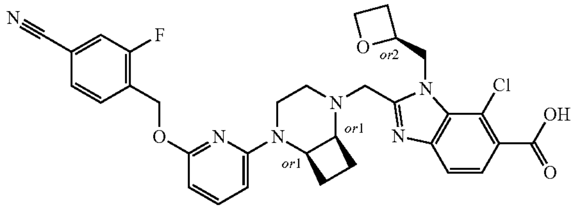

The title compound was prepared from SM 3 Intermediate 45 Isomer 1 (70 mg, 0.11 mmol) as described in Preparation Method F. The crude product was purified by preparative HPLC, PrepMethod H (51-61%) to give the title compound (30 mg, 44%); HRMS (ESI) m/z $[M+H]^+$ calcd for $C_{32}H_{31}ClFN_6O_4$: 617.2074, found: 617.2116; $^1H$ NMR (300 MHz, $CD_3OD$) δ 1.59-1.86 (m, 2H), 1.95-2.05 (m, 1H), 2.05-2.20 (m, 1H), 2.29-2.45 (m, 1H), 2.45-2.55 (m, 1H), 2.70-2.85 (m, 2H), 3.20-3.31 (m, partly overlapping with solvent), 3.60-3.70 (m, 1H), 3.81 (d, 1H), 4.20-4.30 (m, 1H), 4.30-4.46 (m, 2H), 4.54-4.67 (m, 1H), 5.25-5.40 (m, 3H), 5.40-5.45 (m, 2H), 6.10-6.20 (m, 2H), 7.42 (t, 1H), 7.47-7.68 (m, 4H), 7.72 (d, 1H).

Example 8b rel-7-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 2

Isomer 2

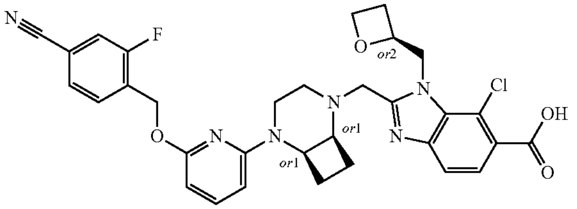

The title compound was prepared from SM 3 Intermediate 46 Isomer 2 (70 mg, 0.11 mmol) as described in Preparation Method F. The crude product was purified by preparative HPLC, PrepMethod H (51-61%) to give the title compound (40 mg, 58%); HRMS (ESI) m/z $[M+H]^+$ calcd for $C_{32}H_{31}ClFN_6O_4$: 617.2074, found: 617.2068; $^1H$ NMR (300 MHz, $CD_3OD$) δ 1.90-2.00 (m, 2H), 2.11-2.19 (m, 1H), 2.25-2.35 (m, 2H), 2.48-2.66 (m, 1H), 2.70-2.90 (m, 2H), 3.20-3.30 (m, 2H), 3.65 (d, 2H), 4.38-4.55 (m, 3H), 4.62-4.76 (m, 1H), 5.11 (dd, 1H), 5.25-3.35 (m, 1H), 5.39-5.56 (m, 3H), 6.13 (d, 2H), 7.42 (t, 1H), 7.48-7.66 (m, 4H), 7.72 (d, 1H)

Example 8c rel-7-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, Isomer 4

Isomer 4

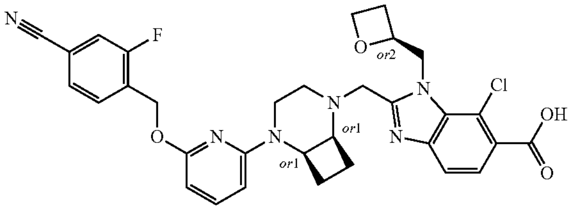

The title compound was prepared from SM 3 Intermediate 47 Isomer 4 (90 mg, 0.14 mmol) as described in Preparation Method F. The crude product was purified by preparative HPLC, PrepMethod H (51-61%) to give the title compound (50 mg, 57%); HRMS (ESI) m/z $[M+H]^+$ calcd for $C_{32}H_{31}ClFN_6O_4$: 617.2074, found: 617.2088; $^1H$ NMR (300 MHz, $CD_3OD$) δ 1.85-1.95 (m, 2H), 2.05-2.20 (m, 1H), 2.20-2.35 (m, 2H), 2.50-2.65 (m, 1H), 2.70-2.90 (m, 2H), 3.20-3.30 (m, 2H), 3.65 (d, 2H), 4.38-4.56 (m, 3H), 4.63-4.76 (m, 1H), 5.12 (dd, 1H), 5.25-5.35 (m, 1H), 5.38-5.55 (m, 3H), 6.13 (d, 2H), 7.43 (t, 1H), 7.48-7.67 (m, 4H), 7.72 (d, 1H).

Example 9a 2-(((1R*,6R*)-5-(6-((4-Chloro-2-fluorobenzyl)oxy) pyridin-2-yl)-2,5-diazabicyclo[4.2.0]octan-2-yl) methyl)-4-methoxy-1-(((S)-oxetan-2-yl)methyl)-1H-benzo[d]imidazole-6-carboxylic acid, Isomer 1

Isomer 1

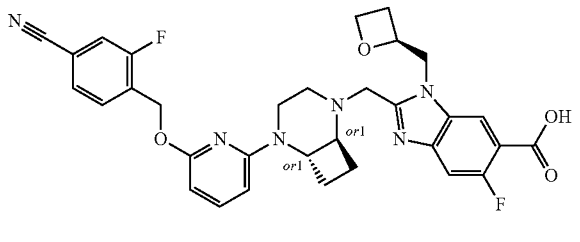

The title compound was prepared from SM 3 Intermediate 36 Isomer 1 (75 mg, 0.12 mmol) as described in Preparation Method E. The reaction mixture was worked-up as described in Preparation Method E and the crude product was purified by preparative HPLC, PrepMethod E (gradient: 50-65%) to give the title compound (43 mg, 66%); MS (ESI) m/z $[M+H]^+$ 622.0; $^1H$ NMR (600 MHz, DMSO-$d_6$) δ 1.16 (dt, 1H), 1.56 (q, 1H), 1.85-1.98 (m, 1H), 2.25 (p, 2H), 2.32-2.41 (m, 2H), 2.62-2.72 (m, 1H), 2.72-2.82 (m, 2H), 3.00-3.12 (m, 1H), 3.71 (d, 1H), 3.83 (d, 1H), 3.98 (d, 1H), 4.32 (dt, 1H), 4.37-4.51 (m, 1H), 4.61 (dd, 1H), 4.80 (dd, 1H), 5.13 (dt, 1H), 5.25-5.47 (m, 2H), 6.17 (dd, 2H), 7.32-7.50 (m, 2H), 7.61 (t, 1H), 7.68 (dd, 1H), 7.85 (dd, 1H), 8.16 (d, 1H), 12.99 (s, 1H)

Example 9b 2-(((1R*,6R*)-5-(6-((4-Chloro-2-fluorobenzyl)oxy) pyridin-2-yl)-2,5-diazabicyclo[4.2.0]octan-2-yl) methyl)-4-methoxy-1-(((S)-oxetan-2-yl)methyl)-1H-benzo[d]imidazole-6-carboxylic acid, Isomer 2

Isomer 2

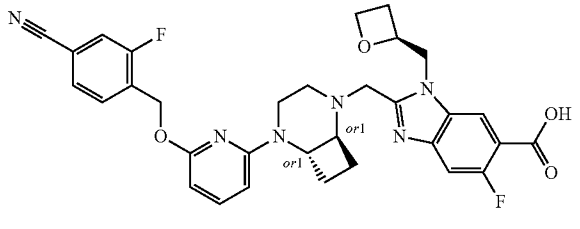

The title compound was prepared from SM 3 Intermediate 37 Isomer 2 (63 mg, 0.10 mmol) as described in Preparation Method E. The reaction mixture was worked-up as described in Preparation Method E and the crude product was purified by preparative HPLC, PrepMethod E (gradient: 50-65%) to give the title compound (34 mg, 70%); MS (ESI) m/z $[M+H]^+$ 622.0; $^1H$ NMR (600 MHz, DMSO-$d_6$) δ 1.25-1.55 (m, 1H), 1.77 (q, 1H), 1.89-2.03 (m, 1H), 2.19-2.38 (m, 4H), 2.65-2.84 (m, 3H), 2.84-3.02 (m, 1H), 3.61 (d, 1H), 3.95 (dd, 2H), 4.36 (dt, 1H), 4.46-4.50 (m, 1H), 4.67 (dd, 1H), 4.78 (dd, 1H), 5.06 (qd, 1H), 5.20-5.51 (m, 2H), 6.17 (t, 2H), 7.40-7.47 (m, 2H), 7.61 (t, 1H), 7.68 (dd, 1H), 7.85 (dd, 1H), 8.14 (d, 1H)

Example 10 rac-1-(2-(tert-Butoxy)ethyl)-2-(((1R,6S)-5-(6-((4-cyano-2-fluorobenzyl)oxy)pyridin-2-yl)-2,5-diazabicyclo[4.2.0]octan-2-yl)methyl)-1H-benzo[d]imidazole-6-carboxylic acid

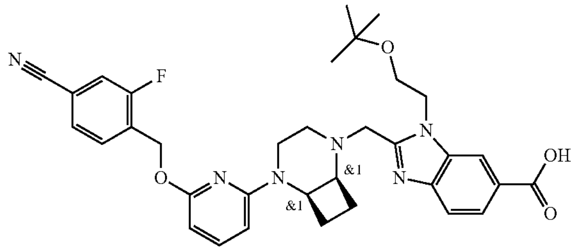 [SMILES: CC(C)(C)OCCn1c(CN2CCN(c3cccc(OCc4ccc(C#N)cc4F)n3)[C@@H]3CC[C@@H]32)nc2ccc(C(=O)O)cc21]

The title compound was prepared from SM 3 Intermediate 34 (100 mg, 0.16 mmol) as described in Preparation Method F. The crude product was purified by preparative HPLC, PrepMethod H (gradient: 55-75%) to give the title compound (80 mg, 82%); HRMS (ESI) m/z $[M+H]^+$ calcd for $C_{34}H_{38}FN_6O_4$: 613.2932, found: 613.2934; $^1H$ NMR (300 MHz, $CDCl_3$) δ 1.02 (s, 9H), 1.83-1.93 (m, 2H), 2.02-2.27 (m, 2H), 2.40 (t, 1H), 2.78-2.88 (m, 1H), 3.17-3.33 (m, 2H), 3.63 (dt, 1H), 3.70-3.83 (m, 3H), 4.28-4.46 (m, 2H), 4.41-4.53 (m, 1H), 4.88 (dt, 1H), 5.35-5.52 (m, 2H), 6.02 (d, 1H), 6.14 (d, 1H), 7.29-7.43 (m, 3H), 7.58 (t, 1H), 7.85 (d, 1H), 8.09 (d, 1H), 8.30 (s, 1H).

Example 11 rac-1-(2-Butoxyethyl)-2-(((1R,6S)-5-(6-((4-cyano-2-fluorobenzyl)oxy)pyridin-2-yl)-2,5-diazabicyclo [4.2.0]octan-2-yl)methyl)-1H-benzo[d]imidazole-6-carboxylic acid

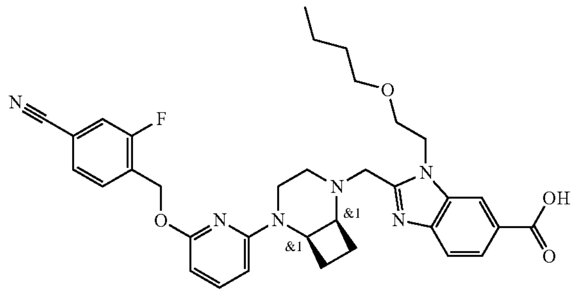 [SMILES: CCCCOCCn1c(CN2CCN(c3cccc(OCc4ccc(C#N)cc4F)n3)[C@@H]3CC[C@@H]32)nc2ccc(C(=O)O)cc21]

The title compound was prepared from SM 3 Intermediate 35 (100 mg, 0.16 mmol) as described in Preparation Method F. The crude compound was purified by preparative HPLC, PrepMethod H (gradient: 59-69%) to give the title compound (80 mg, 82%); HRMS (ESI) m/z $[M+H]^+$ calcd for $C_{34}H_{38}FN_6O_4$: 613.2932, found: 613.2930; $^1H$ NMR (300 MHz, $CDCl_3$) δ 0.83 (t, 3H), 1.14-1.35 (m, 2H), 1.47 (p, 2H), 1.86 (s, 2H), 1.98-2.24 (m, 2H), 2.27-2.45 (m, 1H), 2.80-2.90 (m, 1H), 3.12-3.45 (m, 4H), 3.53-3.89 (m, 4H), 4.29 (d, 1H), 4.37 (q, 1H), 4.50 (d, 1H), 4.90-5.00 (m, 1H), 5.35-5.53 (m, 2H), 6.02 (d, 1H), 6.15 (d, 1H), 7.34 (dd, 1H), 7.35-7.47 (m, 2H), 7.58 (t, 1H), 7.84 (d, 1H), 8.09 (dd, 1H), 8.26 (d, 1H).

Example 12a rel-2-(((1R,6R)-5-(6-((4-Chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylic acid, Isomer 1

Isomer 1

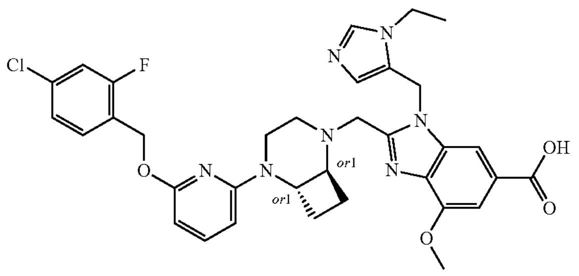

LiOH·$H_2O$ (3.2 mg, 0.076 mmol) was added to a solution of rel-methyl 2-(((1R,6R)-5-(6-((4-chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylate Isomer 1 Intermediate 57 (17 mg, 0.025 mmol) in THF:$H_2O$ (2:1, 3 mL), and the reaction mixture was stirred at rt for 16 h. The reaction mixture was evaporated in vacuo, and the residue was dissolved in DMSO (5 mL) and purified by preparative HPLC, PrepMethod G, (gradient: 40-90%) to give the lithium salt of the title compound (15 mg, 90%); HRMS (ESI) m/z $[M+H]^+$ calcd for $C_{34}H_{36}ClFN_7O_4$: 660.2496, found: 660.2494; $^1H$ NMR (600 MHz, DMSO-$d_6$) δ 1.17 (t, 3H), 1.21-1.31 (m, 1H), 1.62 (q, 1H), 1.95 (t, 1H), 2.19 (q, 1H), 2.25-2.30 (m, 1H), 2.63-2.67 (m, partly overlapping with solvent), 2.91 (d, 1H), 3.08 (s, 3H), 3.55 (d, 1H), 3.68 (d, 1H), 3.88 (s, 3H), 3.95-4.02 (m, 2H), 5.25 (s, 2H), 5.59 (dd, 2H), 6.03-6.19 (m, 2H), 6.38 (s, 1H), 7.28 (d, 2H), 7.37-7.53 (m, 3H), 7.56 (s, 1H), 7.61 (s, 1H).

Example 12b rel-2-(((1R,6R)-5-(6-((4-Chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylic acid, Isomer 2

Isomer 2

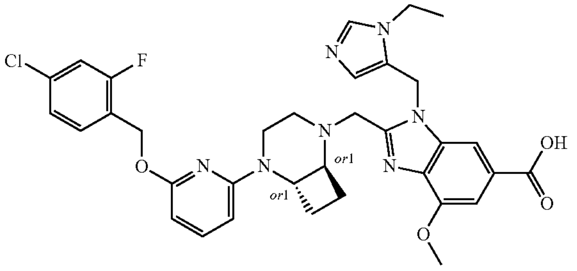

LiOH·$H_2O$ (4 mg, 0.094 mmol) was added to a solution of rel-methyl 2-(((1R,6R)-5-(6-((4-chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylate Isomer 2 Intermediate 58 (21 mg, 0.032 mmol) in THF:$H_2O$ (2:1, 3 mL), and the reaction mixture was stirred at rt for 16 h. The reaction mixture was evaporated in vacuo, and the residue was dissolved in DMSO (5 mL) and purified by preparative HPLC, PrepMethod G, (gradient: 40-90%) to give the lithium salt of the title compound (13 mg, 89%); HRMS (ESI) m/z $[M+H]^+$ calcd for $C_{34}H_{36}ClFN_7O_4$: 660.2496, found: 660.2532; $^1H$ NMR (600 MHz, DMSO-$d_6$) δ 1.17 (t, 3H), 1.21-1.29 (m, 1H), 1.60-1.65 (m, 1H), 1.95 (t, 1H), 2.15-2.33 (m, 2H), 2.63-2.67 (m, partly overlapping with solvent), 2.91 (d, 1H), 3.08 (s, 3H), 3.55 (d, 1H), 3.68 (d, 1H), 3.88 (s, 3H), 3.98 (tt, 2H), 5.25 (s, 2H), 5.53 (d, 1H), 5.66 (d, 1H), 6.12 (dd, 2H), 6.38 (s, 1H), 7.28 (d, 2H), 7.37-7.51 (m, 3H), 7.56 (s, 1H), 7.61 (s, 1H).

Example 13 rac-2-(((1R,6S)-5-(6-((4-Cyano-2-fluorobenzyl)oxy)pyridin-2-yl)-2,5-diazabicyclo[4.2.0]octan-2-yl)methyl)-1-((5-methylisoxazol-3-yl)methyl)-1H-benzo[d]imidazole-6-carboxylic acid

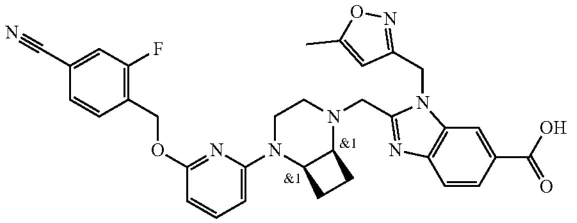 [SMILES: Cc1cc(Cn2c(CN3CCN(c4cccc(OCc5ccc(C#N)cc5F)n4)[C@@H]4CC[C@@H]43)nc3ccc(C(=O)O)cc32)no1]

rac-Methyl 2-(((1R,6S)-5-(6-((4-cyano-2-fluorobenzyl)oxy)pyridin-2-yl)-2,5-diazabicyclo[4.2.0]octan-2-yl)

methyl)-1-((5-methylisoxazol-3-yl)methyl)-1H-benzo[d]imidazole-6-carboxylate Intermediate 62 (0.080 g, 0.13 mmol) was added in one portion to a solution of 1,3,4,6,7,8-hexahydro-2H-pyrimido[1,2-a]pyrimidine (0.036 g, 0.26 mmol) in MeCN (2.4 mL) and water (0.6 mL) and the reaction mixture was stirred at 25° C. for 8 h. The pH of the reaction mixture was adjusted to 7 with 0.5 M citric acid (aq). The mixture was purified by preparative HPLC, Prep-Method H, (gradient: 55-70%) to give the title compound (0.042 g, 54%) as a yellow solid; HRMS (ESI) m/z $[M+H]^+$ calcd for $C_{33}H_{31}FN_7O_4$: 608.2416, found: 608.2432; $^1H$ NMR (300 MHz, $CDCl_3$) δ 1.85-1.95 (m, 2H), 2.05-2.25 (m, 2H), 2.35 (s, 3H), 2.45-2.60 (m, 1H), 2.85-2.95 (m, 1H), 3.25-3.45 (m, 2H), 3.55-3.65 (m, 1H), 3.80-3.90 (m, 1H), 4.10-4.25 (m, 1H), 4.30-4.40 (m, 1H), 5.35-5.52 (m, 2H), 5.65 (d, 1H), 5.80 (s, 1H), 5.92 (d, 1H), 6.01 (d, 1H), 6.17 (d, 1H), 7.30-7.46 (m, 3H), 7.58 (t, 1H), 7.85 (d, 1H), 8.09 (dd, 1H), 8.23 (s, 1H)

Example 14 rac-2-(((1R,6S)-5-(6-((4-Cyano-2-fluorobenzyl)oxy)pyridin-2-yl)-2,5-diazabicyclo[4.2.0]octan-2-yl)methyl)-1-((4-methylpyridin-2-yl)methyl)-1H-benzo[d]imidazole-6-carboxylic acid

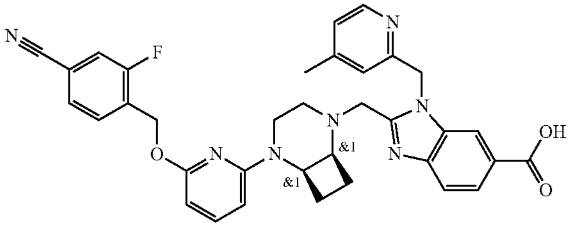 [SMILES: Cc1ccnc(Cn2c(CN3CCN(c4cccc(OCc5ccc(C#N)cc5F)n4)[C@@H]4CC[C@@H]43)nc3ccc(C(=O)O)cc32)c1]

rac-Methyl 2-(((1R,6S)-5-(6-((4-cyano-2-fluorobenzyl)oxy)pyridin-2-yl)-2,5-diazabicyclo[4.2.0]octan-2-yl)methyl)-1-((4-methylpyridin-2-yl)methyl)-1H-benzo[d]imidazole-6-carboxylate Intermediate 66 (0.080 g, 0.13 mmol) was added in one portion to a solution of 1,3,4,6,7,8-hexahydro-2H-pyrimido(1,2-a)-pyrimidine (0.021 g, 0.15 mmol) in water (0.2 mL) and MeCN (0.8 mL), and the reaction mixture was stirred at 25° C. for 2 h. The reaction mixture was concentrated at reduced pressure and the crude product was purified by preparative HPLC, PrepMethod H, (gradient: 45-60%) to give the title compound (0.032 g, 41%) as a white solid; HRMS (ESI) m/z $[M+H]^+$ calcd for $C_{35}H_{33}FN_7O_3$: 618.2624, found: 618.2638; $^1H$ NMR (300 MHz, $CD_3OD$) δ 1.94-1.64 (m, 4H), 2.20-2.40 (m, 4H), 2.84 (dd, 2H), 3.20 (s, 1H), 3.47 (d, 1H), 3.67 (d, 1H), 4.34-4.20 (m, 2H), 5.44 (d, 2H), 5.84 (d, 2H), 6.06 (d, 1H), 6.13 (d, 1H), 6.87 (s, 1H), 7.13 (d, 1H), 7.42 (t, 1H), 7.67-7.50 (m, 3H), 7.72 (d, 1H), 8.12-7.96 (m, 2H), 8.34 (s, 1H).

Example 15

2-(((4aRS,7aSR)-4-(6-((4-Chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid

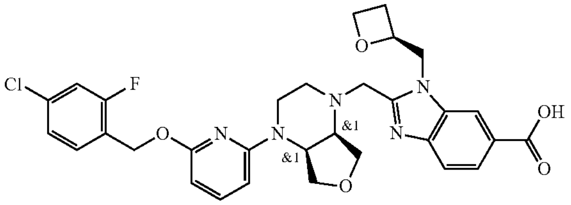 [SMILES: O=C(O)c1ccc2nc(CN3CCN(c4cccc(OCc5ccc(Cl)cc5F)n4)[C@@H]4COC[C@@H]43)n(C[C@@H]3CCO3)c2c1]

Methyl 2-(((4aRS,7aSR)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylate Intermediate 82 (409 mg, 658 μmol) was dissolved in THF (5 mL). A solution of LiOH (72 mg, 1.71 mmol) in water (3 mL) was added, and the mixture was stirred at ambient temperature overnight. The mixture was diluted with 10% $NaHSO_4$ (aq) and extracted with DCM (2×20 mL). The combined organic phase was washed with water (20 mL), dried over $MgSO_4$, filtered, and concentrated in vacuo. The residue was purified by preparative HPLC, PrepMethod J, (gradient: 10-40%), to give the title compound (52 mg, 13%); HRMS (ESI) m/z $[M+H]^+$ calcd for $C_{31}H_{32}ClFN_5O_5$: 608.2070, found: 608.2050;

$^1H$ NMR (400 MHz, DMSO-$d_6$) δ 13.01 (bs, 1H), 8.22 (s, 1H), 7.84-7.72 (m, 1H), 7.61 (dd, 1H), 7.52-7.38 (m, 3H), 7.26 (m, 1H), 6.27 (dd, 1H), 6.07 (dd, 1H), 5.33-5.23 (m, 2H), 5.19-4.79 (m, 3H), 4.67-4.29 (m, 4H), 4.12 (dd, 1H), 3.90-3.65 (m, 3H), 3.62-3.43 (m, 3H), 3.38 (d, 1H), 2.92-2.57 (m, 2H), 2.27 (m, 2H).

Example 16a 2-(((4aR*,7aS*)-4-(6-((4-Chloro-2-fluorobenzyl)oxy)pyridin-2-yl)hexahydrofuro[3,4-b]pyrazin-1(2H)-yl)methyl)-4-methoxy-1-(((S)-oxetan-2-yl)methyl)-1H-benzo[d]imidazole-6-carboxylic acid, Isomer 1

Isomer 1

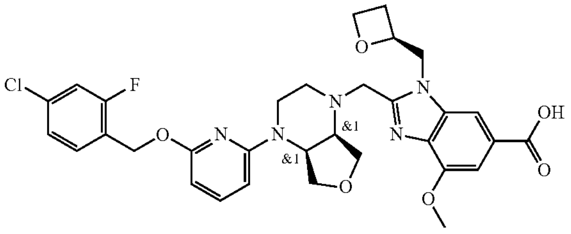

LiOH·$H_2O$ (9 mg, 223 μmol) was added to a solution of methyl 2-(((4aR*,7aS*)-4-(6-((4-chloro-2-fluorobenzyl)oxy)pyridin-2-yl)hexahydrofuro[3,4-b]pyrazin-1(2H)-yl)

methyl)-4-methoxy-1-(((S)-oxetan-2-yl)methyl)-1H-benzo[d]imidazole-6-carboxylate Isomer 1 Intermediate 84 (58 mg) in THF-$H_2O$ (2:1, 5 mL), and the reaction mixture was stirred at rt for 16 h. The mixture was acidified with $NaH_2PO_4$ (aq), diluted with water, and extracted with EtOAc. The combined organic layer was dried over $Na_2SO_4$, filtered and concentrated. The residue was purified by preparative HPLC, PrepMethod E, (gradient: 0-50%) to afford the title compound (33 mg, 53%); HRMS (ESI) m/z $[M+H]^+$ calcd for $C_{32}H_{34}ClFN_5O_6$: 638.2181, found: 638.2203; 1H NMR (600 MHz, DMSO-$d_6$) δ 7.61 (s, 1H), 7.48 (t, 1H), 7.45-7.38 (m, 2H), 7.31 (s, 1H), 7.27 (dd, 1H), 6.27 (d, 1H), 6.07 (d, 1H), 5.35-5.24 (m, 2H), 5.16 (tt, 1H), 4.86 (td, 1H), 4.77 (dd, 1H), 4.53-4.37 (m, 3H), 4.15 (d, 1H), 4.06 (dt, 1H), 3.88 (s, 3H), 3.85-3.68 (m, 3H), 3.52 (dd, 1H), 3.37 (d, 1H), 2.89-2.80 (m, 2H), 2.81-2.69 (m, 1H), 2.59-2.53 (m, 1H), 2.31-2.18 (m, 2H).

Example 16b 2-(((4aR*,7aS*)-4-(6-((4-Chloro-2-fluorobenzyl)oxy)pyridin-2-yl)hexahydrofuro[3,4-b]pyrazin-1(2H)-yl)methyl)-4-methoxy-1-(((S)-oxetan-2-yl)methyl)-1H-benzo[d]imidazole-6-carboxylic acid, Isomer 2

Isomer 2

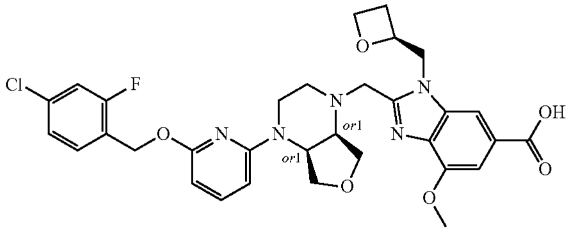

$LiOH·H_2O$ (9 mg, 223 μmol) was added to a solution of methyl 2-(((4aR*,7aS*)-4-(6-((4-chloro-2-fluorobenzyl)oxy)pyridin-2-yl)hexahydrofuro[3,4-b]pyrazin-1(2H)-yl)methyl)-4-methoxy-1-(((S)-oxetan-2-yl)methyl)-1H-benzo[d]imidazole-6-carboxylate Isomer 2 Intermediate 85 (60 mg) in THF-$H_2O$ (2:1, 5 mL), and the reaction mixture was stirred at rt for 16 h. The mixture was acidified with $NaH_2PO_4$ (aq), diluted with water, and extracted with EtOAc. The combined organic layer was dried over $Na_2SO_4$, filtered, and concentrated. The residue was purified preparative HPLC, PrepMethod E, (gradient: 0-50%) to afford the title compound (32 mg, 53%); HRMS (ESI) m/z $[M+H]^+$ calcd for $C_{32}H_{34}ClFN_5O_6$: 638.2181, found: 638.2181; 1H NMR (600 MHz, DMSO-$d_6$) δ 7.60 (s, 1H), 7.52-7.40 (m, 3H), 7.34-7.22 (m, 2H), 6.29 (d, 1H), 6.08 (d, 1H), 5.36-5.23 (m, 2H), 4.96 (m, 3H), 4.58-4.26 (m, 6H), 3.84 (m, 6H), 3.60 (dd, 1H), 2.93-2.63 (m, 5H), 2.24 (td, 1H).

Example 17

2-(((4aRS,7aSR)-4-(6-((4-Cyano-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid

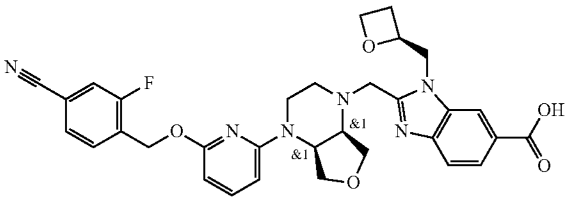 [SMILES: N#Cc1ccc(COc2cccc(N3CCN(Cc4nc5ccc(C(=O)O)cc5n4C[C@@H]4CCO4)[C@H]4COC[C@H]43)n2)c(F)c1]

A solution of $LiOH·H_2O$ (68 mg, 1.63 mmol) in water (3 mL) was added to a solution of methyl 2-(((4aRS,7aSR)-4-(6-((4-cyano-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylate Intermediate 86 (384 mg, 626 μmol) in THE (5 mL), and the reaction mixture was stirred at ambient temperature overnight. 10% $NaHSO_4$ (aq) was added and the mixture was extracted with DCM (2×20 mL). The combined organic phase was washed with water (20 mL), dried over $MgSO_4$, filtered, and concentrated in vacuo. The residue was purified by preparative HPLC, PrepMethod J (gradient: 15-25%) to give the title compound (39 mg, 10%); HRMS (ESI) m/z $[M+H]^+$ calcd for $C_{32}H_{32}FN_6O_5$: 599.2412, found: 599.2438; 1H NMR (400 MHz, 600 MHz, DMSO-$d_6$) 12.64 (bs, 1H) δ 8.23 (s, 1H), 7.85 (m, 1H), 7.79 (t, 1H), 7.63 (m, 3H), 7.45 (q, 1H), 6.27 (dd, 1H), 6.12 (m, 1H), 5.38 (m, 2H), 5.14 (s, 1H), 5.06-4.89 (m, 1H), 4.88-4.72 (m, 1H), 4.64 (m, 1H), 4.56-4.38 (m, 3H), 4.31 (d, 1H), 4.11 (dd, 1H), 3.88-3.62 (m, 3H), 3.63-3.35 (m, 3H), 2.84 (d, 2H), 2.70 (m, 1H), 2.33-2.16 (m, 1H).

Example 18a rel-2-(((4aR,7aS)-4-(6-((4-Chloro-2-fluorobenzyl)oxy)pyridin-2-yl)hexahydrofuro[3,4-b]pyrazin-1(2H)-yl)methyl)-4-fluoro-1-(((S)-tetrahydrofuran-3-yl)methyl)-1H-benzo[d]imidazole-6-carboxylic acid Isomer 2

Isomer 2

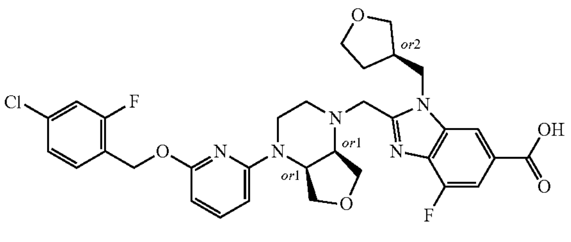

LiOH monohydrate (7.9 mg, 0.18 mmol) was added to a solution of methyl 2-(((4aR,7aS)-4-(6-((4-chloro-2-fluorobenzyl)oxy)pyridin-2-yl)hexahydrofuro[3,4-b]pyrazin-1 (2H)-yl)methyl)-4-fluoro-1-(((R)-tetrahydrofuran-3-yl) methyl)-1H-benzo[d]imidazole-6-carboxylate Isomer 2 Intermediate 91 (47 mg, 72 μmol) in THF:$H_2O$ (2:1, 2 mL) and the reaction mixture was stirred at rt for 16 h. The reaction mixture was purified by preparative HPLC, Prep-Method E (gradient: 10-50%) to give the lithium salt of the title compound Isomer 2 (35 mg, 53%); HRMS (ESI) m/z $[M+H]^+$ calcd for $C_{32}H_{33}ClF_2N_5O_5$: 640.2132, found: 640.2148; $^1H$ NMR (600 MHz, DMSO-$d_6$) δ 1.65-1.70 (m, 1H), 1.85-1.95 (m, 1H), 2.27 (t, 1H), 2.77 (d, 1H), 2.88 (d, 2H), 2.95-3.05 (m, 1H), 3.40-3.45 (m, partly overlapping with solvent), 3.51 (q, 2H), 3.57 (t, 1H), 3.62 (q, 1H), 3.72-3.90 (m, 3H), 4.21 (d 1H), 4.25-4.39 (m, 3H), 4.44 (dd, 1H), 4.88 (q, 1H), 5.29 (d, 2H), 6.08 (d, 1H), 6.28 (d, 1H), 7.23-7.32 (m, 1H), 7.39-7.54 (m, 4H), 7.84 (s, 1H).

Example 18b rel-2-(((4aR,7aS)-4-(6-((4-Chloro-2-fluorobenzyl) oxy)pyridin-2-yl)hexahydrofuro[3,4-b]pyrazin-1 (2H)-yl)methyl)-4-fluoro-1-(((S)-tetrahydrofuran-3-yl)methyl)-1H-benzo[d]imidazole-6-carboxylic acid Isomer 3

Isomer 3

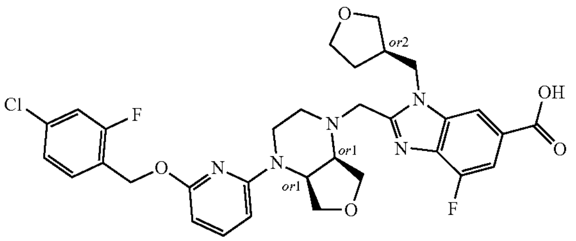

The title compound was prepared as described in Example 18a from methyl 2-(((4aR,7aS)-4-(6-((4-chloro-2-fluorobenzyl)oxy)pyridin-2-yl)hexahydrofuro[3,4-b]pyrazin-1 (2H)-yl)methyl)-4-fluoro-1-(((R)-tetrahydrofuran-3-yl) methyl)-1H-benzo[d]imidazole-6-carboxylate Isomer 3 Intermediate 92 (10 mg, 15 μmol) to give the lithium salt of the title compound Isomer 3 (6 mg, 53%); HRMS (ESI) m/z $[M+H]^+$ calcd for $C_{32}H_{33}ClF_2N_5O_5$: 640.2132, found: 640.2164; $^1H$ NMR (600 MHz, DMSO-$d_6$) δ 1.69-1.75 (m, 1H), 1.84-1.96 (m, 1H), 2.25 (t, 1H), 2.75 (d, 1H), 2.80-2.90 (m, 2H), 2.97 (s, 1H), 3.39-3.45 (m, partly overlapping with solvent), 3.52 (dt, 2H), 3.63 (q, 1H), 3.74-3.85 (m, 2H), 3.84-3.90 (m, 2H), 4.25-4.40 (m, 4H), 4.43 (dd, 1H), 4.88 (q, 1H), 5.29 (d, 2H), 6.08 (d, 1H), 6.28 (d, 1H), 7.27 (d, 1H), 7.38-7.55 (m, 4H), 7.85 (s, 1H).

Example 19a 2-(((4aR*,7aS*)-4-(6-((4-Chloro-2-fluorobenzyl) oxy)pyridin-2-yl)hexahydrofuro[3,4-b]pyrazin-1 (2H)-yl)methyl)-4-fluoro-1-(((S)-oxetan-2-yl) methyl)-1H-benzo[d]imidazole-6-carboxylic acid, Isomer 1

ISOMER 1

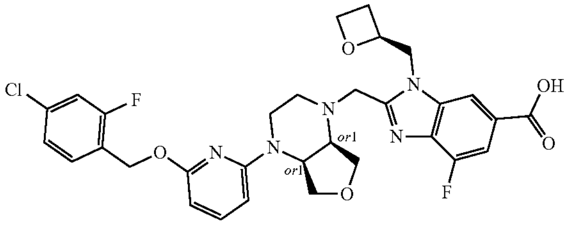

LiOH monohydrate (7.9 mg, 0.18 mmol) was added to a solution of methyl 2-(((4aR*,7aS*)-4-(6-((4-chloro-2-fluorobenzyl)oxy)pyridin-2-yl)hexahydrofuro[3,4-b]pyrazin-1 (2H)-yl)methyl)-4-fluoro-1-(((S)-oxetan-2-yl)methyl)-1H-benzo[d]imidazole-6-carboxylate, Isomer 1 Intermediate 94 (46 mg, 72 μmol) in THF:$H_2O$ (2:1, 3 mL) was added and the reaction mixture was stirred at rt for 16 h. The reaction mixture was acidified with $NaH_2PO_4$ (aq) solution, diluted with water and extracted with EtOAc. The organic layer was dried over $Na_2SO_4$ and concentrated. The residue was purified by preparative HPLC, PrepMethod E, (gradient: 0-50%) to give the lithium salt of the title compound Isomer 1 (35 mg, 85%); HRMS (ESI) m/z $[M+H]^+$ calcd for $C_{31}H_{31}ClF_2N_5O_5$: 626.1976, found: 626.1974; $^1H$ NMR (600 MHz, DMSO-$d_6$) δ 2.16-2.33 (m, 2H), 2.58 (d, 1H), 2.75 (d, 1H), 2.80-2.92 (m, 2H), 3.42 (d, 1H), 3.53 (t, 1H), 3.70-3.84 (m, 3H), 4.09 (dt, 1H), 4.15 (d, 1H), 4.43 (td, 1H), 4.45-4.57 (m, 2H), 4.74-4.95 (m, 2H), 5.17 (dt, 1H), 5.29 (d, 2H), 6.04-6.10 (m, 1H), 6.27 (d, 1H), 7.27 (dd, 1H), 7.38-7.56 (m, 4H), 7.85 (s, 1H).

Example 19b 2-(((4aR*,7aS*)-4-(6-((4-Chloro-2-fluorobenzyl) oxy)pyridin-2-yl)hexahydrofuro[3,4-b]pyrazin-1 (2H)-yl)methyl)-4-fluoro-1-(((S)-oxetan-2-yl) methyl)-1H-benzo[d]imidazole-6-carboxylic acid, Isomer 2

ISOMER 2

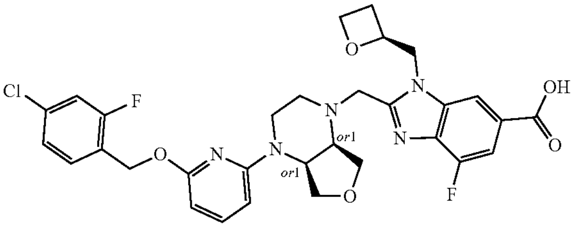

The title compound was prepared as described in Example 19a from methyl 2-(((4aR*,7aS*)-4-(6-((4-chloro-2-fluorobenzyl)oxy)pyridin-2-yl)hexahydrofuro[3,4-b]pyrazin-1(2H)-yl)methyl)-4-fluoro-1-(((S)-oxetan-2-yl)methyl)-1H-benzo[d]imidazole-6-carboxylate, Isomer 2 Intermediate 95 (41 mg, 64 µmol) to give the lithium salt of the title compound Isomer 2 (31 mg, 32%); HRMS (ESI) m/z $[M+H]^+$ calcd for $C_{31}H_{31}ClF_2N_5O_5$: 626.1976, found: 626.1974; $^1H$ NMR (600 MHz, DMSO-$d_6$) δ 2.17-2.31 (m, 1H), 2.65-2.78 (m, 2H), 2.83-2.95 (m, 2H), 3.33-3.37 (m, 2H), 3.60 (dd, 1H), 3.81 (q, 2H), 3.87-3.94 (m, 1H), 4.33 (d, 1H), 4.39-4.59 (m, 4H), 4.94 (ddd, 2H), 5.03 (q, 1H), 5.30 (d, 2H), 6.09 (dd, 1H), 6.29 (dd, 1H), 7.28 (dd, 1H), 7.40-7.53 (m, 4H), 7.84 (d, 1H).

Example 20 rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(oxazol-4-ylmethyl)-1H-benzo[d]imidazole-6-carboxylic acid, Isomer 1

ISOMER 1

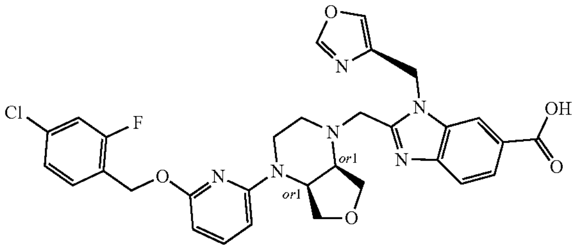

LiOH monohydrate (26 mg, 0.59 mmol) was added to a solution of rel-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(oxazol-4-ylmethyl)-1H-benzo[d]imidazole-6-carboxylate Isomer 1 Intermediate 100 (149 mg, 0.23 mmol) in THF:$H_2O$ (2:1, 4 mL) and the reaction mixture was stirred at rt for 16 h. The reaction mixture was purified by preparative HPLC, PrepMethod E (gradient: 10-50%) to give the lithium salt of the title compound Isomer 1 (99 mg, 74%); HRMS (ESI) m/z $[M+H]^+$ calcd for $C_{31}H_{29}ClFN_6O_5$: 619.1866, found: 619.1872; $^1H$ NMR (600 MHz, DMSO-$d_6$) δ 2.29 (td, 1H), 2.73-2.93 (m, 3H), 3.45 (dd, 2H), 3.63-3.79 (m, 2H), 3.84 (dd, 1H), 4.28 (d, 1H), 4.61 (d, 1H), 4.85 (q, 1H), 5.29 (d, 2H), 5.55 (d, 1H), 5.68 (d, 1H), 6.07 (d, 1H), 6.26 (d, 1H), 7.26 (dd, 1H), 7.33-7.54 (m, 4H), 7.75 (d, 1H), 8.03 (d, 2H), 8.32 (s, 1H).

Example 21 rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(pyridin-3-ylmethyl)-1H-benzo[d]imidazole-6-carboxylic acid, Isomer 1

ISOMER 1

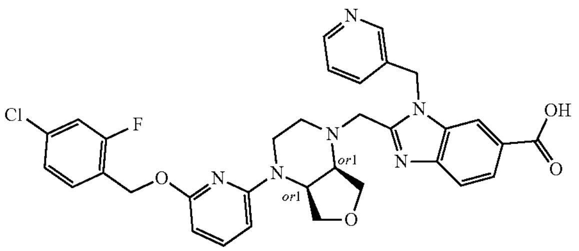

LiOH monohydrate (5.8 mg, 132 µmol) was added to a solution of rel-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(pyridin-3-ylmethyl)-1H-benzo[d]imidazole-6-carboxylate, Isomer 1 Intermediate 105 (34 mg, 53 µmol) in a solution of THF:$H_2O$ (2:1, 2 mL) and the reaction mixture was stirred at rt for 16 h. The reaction mixture was purified by preparative HPLC, PrepMethod E (gradient: 40-55%) to give the lithium salt of the title compound Isomer 1 (28 mg, 53%); HRMS (ESI) m/z $[M+H]^+$ calcd for $C_{33}H_{31}ClFN_6O_4$: 629.2074, found: 629.2088; $^1H$ NMR (600 MHz, DMSO-$d_6$) δ 2.21 (t, 1H), 2.43 (m, partly overlapping with solvent), 2.73 (d, 1H), 2.80 (d, 1H), 2.96-3.08 (m, 1H), 3.40 (d, 1H), 3.60 (t, 1H), 3.66 (d, 1H), 3.74-3.79 (m, 1H), 4.19 (d, 1H), 4.40 (d, 1H), 4.77 (q, 1H), 5.26 (s, 2H), 5.64 (s, 2H), 6.06 (d, 1H), 6.20 (d, 1H), 7.28 (dd, 2H), 7.35-7.51 (m, 5H), 7.73-7.82 (m, 2H), 8.32-8.42 (m, 2H).

Example 22a

4-Chloro-2-(((4aR*,7aS*)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid, Isomer 1

ISOMER 1

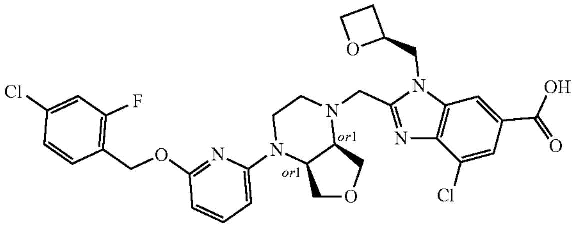

LiOH monohydrate (6.5 mg, 154 µmol) was added to a solution of methyl 4-chloro-2-(((4aR*,7aS*)-4-(6-((4- chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylate Isomer 1 Intermediate 111 (40 mg, 61 μmol) in THF:$H_2O$ (2:1, 5 mL) and the reaction mixture was stirred at rt for 16 h. The reaction mixture was acidified with $NaH_2PO_4$ (aq), diluted with water and extracted with EtOAc. The organic layer was dried over $Na_2SO_4$, filtered and concentrated at reduced pressure, and the residue was purified by preparative HPLC, PrepMethod E (gradient 10-55%) to give the title compound (28.5 mg, 67%); HRMS (ESI) m/z $[M+H]^+$ calcd for $C_{31}H_{31}Cl_2FN_5O_5$: 642.1680, found: 642.1694; $^1H$ NMR (600 MHz, DMSO-$d_6$) δ 2.25-2.35 (m, 1H), 2.68 (d, 2H), 2.83-2.94 (m, 2H), 3.45 (d, 1H), 3.58 (t, 2H), 3.76-3.92 (m, 3H), 4.33 (d, 1H), 4.44-4.62 (m, 4H), 4.88-5.08 (m, 3H), 5.24-5.35 (m, 2H), 6.09 (d, 1H), 6.29 (d, 1H), 7.28 (dd, 1H), 7.40-7.53 (m, 3H), 7.78 (d, 1H), 8.25 (s, 1H), 13.06 (br s, 1H).

Example 22b

4-Chloro-2-(((4aR*,7aS*)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid, Isomer 2

ISOMER 2

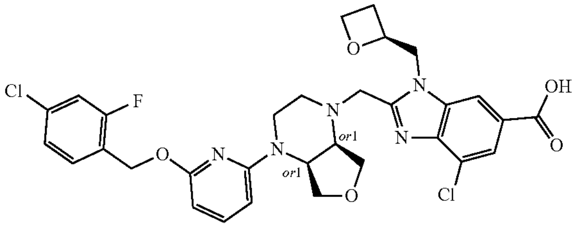

The title compound was prepared as described for Example 22a from methyl 4-chloro-2-(((4aR*,7aS*)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylate Isomer 2 Intermediate 112 (37 mg, 56 μmol) to give the title compound Isomer 2 (27.7 mg, 66%); HRMS (ESI) m/z $[M+H]^+$ calcd for $C_{31}H_{31}Cl_2FN_5O_5$: 642.1680, found: 642.1678; 1H NMR (600 MHz, DMSO-$d_6$) δ 2.17-2.36 (m, 2H), 2.73 (d, 1H), 2.80-2.95 (m, 2H), 3.47-3.61 (m, 3H), 3.71-3.86 (m, 3H), 4.09-4.18 (m, 2H), 4.43 (q, 1H), 4.53 (d, 1H), 4.70 (dd, 1H), 4.84-4.95 (m, 2H), 5.16 (d, 1H), 5.25-5.36 (m, 2H), 6.08 (d, 1H), 6.27 (d, 1H), 7.27 (dd, 1H), 7.40-7.54 (m, 3H), 7.80 (d, 1H), 8.26 (s, 1H), 13.11 (brs, 1H)

Example 23 rel-2-(((4aR,7aS)-4-(6-((4-Chloro-2-fluorobenzyl)oxy)pyridin-2-yl)hexahydrofuro[3,4-b]pyrazin-1(2H)-yl)methyl)-4-fluoro-1-(2-(2-methyl-1H-imidazol-1-yl)ethyl)-1H-benzo[d]imidazole-6-carboxylic acid, Isomer 1

ISOMER 1

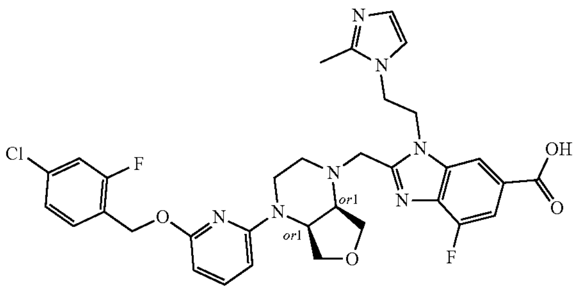

LiOH hydrate (7.5 mg, 154 μmol) was added to a solution of rel-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-4-fluoro-1-(2-(2-methyl-1H-imidazol-1-yl)ethyl)-1H-benzo[d]imidazole-6-carboxylate Isomer 1 Intermediate 118 (47 mg, 69 μmol) in THF:$H_2O$ (2:1, 5 mL) and the reaction mixture was stirred at rt for 16 h. The reaction mixture was concentrated at reduced pressure, the residue was dissolved in DMSO (5 mL) and purified by preparative HPLC, PrepMethod E (gradient: 10-70%) to give the lithium salt of the title compound (28 mg, 56%); HRMS (ESI) m/z $[M+H]^+$ calcd for $C_{33}H_{33}ClF_2N_7O_4$: 664.2244, found: 664.2266; $^1H$ NMR (600 MHz, DMSO-$d_6$) δ 1.84 (s, 3H), 2.17-2.27 (m, 1H), 2.67 (d, 1H), 2.80-2.92 (m, 2H), 3.15 (d, 1H), 3.51 (dd, 1H), 3.69 (d, 1H), 3.77 (dt, 3H), 4.03 (d, 1H), 4.23-4.39 (m, 2H), 4.66 (t, 2H), 4.85 (q, 1H), 5.23-5.35 (m, 2H), 6.07 (d, 1H), 6.27 (d, 1H), 6.69 (d, 1H), 6.84 (d, 1H), 7.27 (dd, 1H), 7.38-7.52 (m, 4H), 7.78 (s, 1H).

Example 24 rel-4-Chloro-2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylic acid, Isomer 1

ISOMER 1

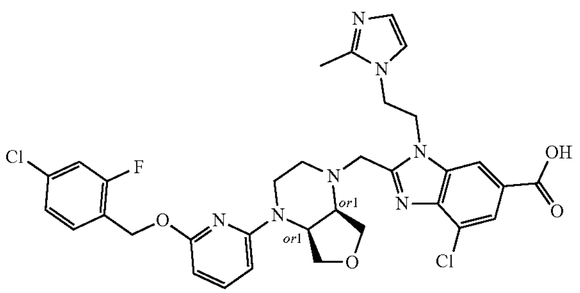

LiOH hydrate (1.4 mg, 31 μmol) was added to a solution of rel-methyl 4-chloro-2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate Isomer 1 Intermediate 124 (7.2 mg, 10 μmol) in THF:$H_2O$ (1:1, 3 mL) and the reaction mixture was stirred at rt for 24 h. The reaction mixture was concentrated in vacuo and the residue was dissolved in DMSO (5 mL) and purified by preparative HPLC, PrepMethod E (gradient: 0-300%), to give the lithium salt of the title compound (6 mg, 90%); HRMS (ESI) m/z $[M+H]^+$ calcd for $C_{33}H_{33}Cl_2FN_7O_4$: 680.1950, found: 680.1974; $^1H$ NMR (600 MHz, DMSO-$d_6$) δ 2.05 (s, 3H), 2.77-2.98 (m, 4H), 3.41-3.57 (m, partly overlapping with solvent), 3.74-3.90 (m, 3H), 4.23-4.38 (m, 3H), 4.77-4.99 (m, 3H), 5.24-5.37 (m, 2H), 6.09 (d, 1H), 6.29 (d, 1H), 6.96-7.18 (m, 1H), 7.20-7.30 (m, 2H), 7.46 (dt, 3H), 7.60 (s, 1H), 7.77 (s, 1H).

Example 25a rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylic acid, Isomer 1

ISOMER 1

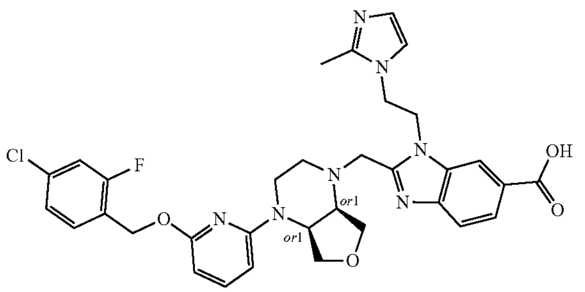

LiOH hydrate (1.4 mg, 33 μmol) was added to a solution of rel-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate, Isomer 1 Intermediate 130 (8.6 mg, 13 μmol) in THF:$H_2O$ (2:1, 2 mL) and the reaction mixture was stirred at rt for 16 h. The reaction mixture was concentrated at reduced pressure and the residue was dissolved in DMSO (5 mL) and purified by preparative HPLC; PrepMethod E (gradient: 0-50%) to give the lithium salt of the title compound Isomer 1 (3.3 mg, 62%); HRMS (ESI) m/z $[M+H]^+$ calcd for $C_{33}H_{34}ClFN_7O_4$: 646.2340, found: 646.2340.

Example 25b rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylic acid, Isomer 2

ISOMER 2

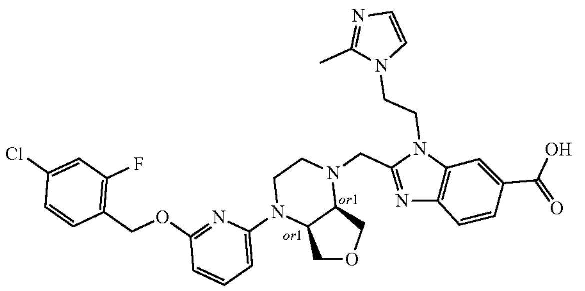

The title compound was prepared as described for Example 25a from rel-methyl 2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylate, Isomer 2 Intermediate 131 (5 mg, 7.6 μmol) to give the lithium salt of the title compound Isomer 2 (4.1 mg, 53%); HRMS (ESI) m/z $[M+H]^+$ calcd for $C_{33}H_{34}ClFN_7O_4$: 646.2340, found: 646.2356.

Pharmacological Activity

CHOK1 GLP-1R cAMP Assay

A cell line stably expressing the human GLP-1R receptor (NM_002062.5, including the naturally-occurring variant Leu260Phe) in a CHO-K1 (ATCC® CCL-61™) was used for assay.

GLP-1 receptor mediated agonist activity was determined in a cell-based assay measuring cyclic adenosine monophosphate (cAMP) levels in cells using Homogeneous Time-Resolved Fluorescence (HTRF) cAMP detection kit (CisBio catalog #62AM4PEC, cAMP Gs Dynamic range kit). The cAMP detection method is based on a competitive immunoassay, in which cAMP produced by the cells and cAMP labeled with the dye d2 compete for binding to a Europium-Cryptate-labeled anti-cAMP antibody. The specific HTRF signal is inversely proportional to the concentration of cAMP.

Compounds were added to individual well in 384 well-assay plates (Greiner #784076) using an Echo (LabCyte) dispenser from 10 mM stocks. Varying concentration of compounds were added to wells, and DMSO was used to normalize each well to a volume of 100 nL. A dose response curve of GLP-1(7-36)NH2 (Bachem H-6795) was included in each run. 5 μL of cAMP concentration response standards are applied in specified wells in the assay plates. Cryo-preserved cells are thawed and resuspended in assay buffer pre-heated to 37° C. (20 mM 2-[4-(2-hydroxyethyl)piperazin-1-yl]ethanesulfonic acid (HEPES) pH 7.4, lx Hank's Balanced Salt Solution (HBSS, Life Technologies #14065) supplemented with 0.1% (w/v) bovine serum albumin (Sigma, A-7030)). Cells were centrifuged at 250*g for 5 min at rt, and resuspended in room tempered assay buffer to a final density of $0.16*10^6$ cell/mL, to deliver 800 cells/well. 5 μL of assay buffer with 1 mM 3-isobutyl-1-methylxanthin (IBMX; Sigma cat I-7018) was dispensed per well in assay plates using a multidrop combi (Thermo Scientific) subsequently 5 μL of cell suspension was distributed to relevant wells in the assay using a multidrop dispenser. Assay plates were incubated 20 min at rt.

Detection reagents, Europium-Cryptate-labeled anti-cAMP antibody and cAMP labeled with the dye d2, are diluted in lysis buffer, provided by the manufacturer. 5 μL of each detection reagent is supplemented to each assay well using a multidrop dispenser. Assay plates are incubated in the dark for at least one h. The HTRF signal is measured using the HTRF module (excitation: 337 nm, emission A: 665 nm and emission B: 620 nm) in Pherastar FSX (BMG Labtech).

Raw data were converted to pM cAMP using the cAMP standard curve included in each run. Converted data were further analyzed in Genedata Screener (Genedata) and EC50 determinations were made from agonist dose-response curves analyzed with a curve fitting program using a 4-parameter logistic dose response equation (Equation y=A+((B−A)/1+((C/x)^D))) where A is no stimulation, B is full stimulation, C is the EC50 and D is the Hill slope). The percent effect was determined relative to a saturating concentration of a full GLP-1R agonist (GLP-1(7-36)NH2 has 100% effect in this assay setup).

The GLP-1R $EC_{50}$ values for the Example compounds are set forth in Table 1 herein below.

TABLE 1

| Ex. No. | GLP-1R EC50 (nM) |
|---|---|
| 1 | 130 |
| 2a | 1.2 |
| 2b | 17 |
| 3a | 23 |
| 3b | 1.1 |
| 4a | 4 |
| 4b | 0.6 |
| 5a | 6.4 |
| 5b | 0.5 |
| 6a | 0.6 |
| 6b | 95 |
| 6c | 8.1 |
| 6d | 3.5 |
| 7a | 9.4 |
| 7b | 90 |
| 7c | 250 |
| 8a | 6.1 |
| 8b | 28 |
| 8c | 140 |
| 9a | 180 |
| 9b | 2.1 |
| 10 | 370 |
| 11 | 150 |
| 12a | 2.2 |
| 12b | 8.9 |
| 13 | 110 |
| 14 | 400 |
| 15 | 3.3 |
| 16a | 0.63 |
| 16b | 64 |
| 17 | 2 |
| 18a | 110 |
| 18b | 57 |
| 19a | 1.5 |
| 19b | 120 |
| 20 | 35 |
| 21 | 74 |
| 22a | 1 |
| 22b | 150 |
| 23 | 170 |
| 24 | 250 |
| 25a | 110 |
| 25b | 250 |

EndoC cAMP Accumulation Assay

A HTRF cAMP assay (cAMP Gs dynamic kit; CisoBio Cat #62AM4PEJ) was used to identify agonists of GLP-1R in a pancreatic insulinoma cell line (EndoC-PH1). The EndoC-βH1 cell line was sourced from Univercell Biosolutions and is a genetically engineered human pancreatic β cell line which exhibits glucose-inducible insulin secretion. EndoC-βH1 cells have detectable GLP-1R messenger ribonucleic acid (mRNA) as detected by quantitative polymerase chain reaction (qPCR). The functionality of GLP-1R signalling in EndoC-βH1 has been demonstrated by Exendin-4 treatment leading to augmented insulin secretion; an effect which is blunted with short hairpin ribonucleic acid (shRNA)-mediated knockdown of GLP-1R. The EndoC-βH1 cell line is a valid model of human beta cells and applicable for screenings to identify novel drug target candidates (*Mol. Metab.,* 2018, 8, 144-157). CisBio HTRF cAMP kits are based on a competitive immunoassay using cryptate-labelled anti-cAMP antibody and d2-labeled cAMP. The detection kit is intended for the direct quantitative determination of cAMP. The specific signal (i.e. energy transfer) is inversely proportional to the concentration of cAMP in the standard or sample. Test compounds (10 mM in DMSO) were diluted into assay buffer (HBSS (Sigma #H8264) supplemented with 25 mM HEPES (Gibco #15630, pH 7.4), 0.1% BSA (Sigma #A3059) and 0.5 mM IBMX (Sigma #I7018) included fresh on the day of the assay) into 96 well U-bottom plates (Greiner #650201). Diluted compounds were transferred to ECHO source polypropelene plates (Labcyte #P-05525) and dose response curves were dispensed acoustically using ECHO 550 into black shallow-well u-bottom 384-well HTRF Assay Plates (Corning 4514).

Cryovials of EndoC-H1 (supplied at $1\times10e^7$ cells/vial) were used directly for screening. The cryovials and were removed from $N_2$(l) and thawed rapidly in a 37° C. water bath. The cells were resuspended in assay buffer and centrifuged at 300 g for 5 min. Cells were resuspended in assay buffer at the appropriate concentration, typically at 12e5 cells per mL (3000 cells per well, dependent on cell batch) and 2.5 μL diluted cells were added to all wells of destination plate by Multidrop combi reagent dispenser (Thermofisher). The plates were incubated at rt for 30 min. The assay was stopped by adding 2.5 μL anti-cAMP cryptate solution to all wells and 2.5 μL cAMP-d2 solution (both diluted 1:20 in lysis buffer) to columns 1-22 by Combi drop. A volume of 2.5 μL cAMP-d2 solution was added to wells E23 to P24 and 2.5 μL lysis buffer added to wells A23 to D24 by multichannel pipette. The plates were incubated at rt for 1 h and read on an Envision plate reader using excitation wavelength of 320 nm and emission of 590 nm and 660 nm.

Raw data from Envision is converted to % DeltaF according to the manufacturer's instructions. Dose response curves are analysed via 4-Parameter Logistical Analysis and assay plate Z' values obtained. Samples are graphed as percentage (%) activation plots compared to GIP (1-42, Bachem H-5645) with assay window defined by negative control as basal cell cAMP levels and positive control are defined by maximum GIP (82.5 nM) signal. GLP-1 (7-36 amide, Bachem H-6795) dose response curve was included on all plates.

The EndoC $EC_{50}$ values for the Example compounds are set forth in Table 2 herein below.

TABLE 2

| Ex. No. | EndoC EC50 (nM) |
|---|---|
| 1 | 280 |
| 2a | 4.1 |
| 2b | 32 |
| 3a | 13 |
| 3b | 8.7 |
| 4a | 5.5 |
| 4b | 3.0 |
| 5a | 4.0 |
| 5b | 2.1 |
| 6a | 1.9 |
| 6b | 57 |
| 6c | 5.6 |
| 6d | 2.4 |
| 7a | 7.2 |
| 7b | 40 |
| 7c | |
| 8a | 28 |
| 8b | 41 |
| 8c | 620 |
| 9a | 69 |
| 9b | 27 |
| 10 | |
| 11 | |
| 12a | |
| 12b | 16 |
| 13 | 100 |
| 14 | 2800 |
| 15 | 14 |
| 16a | 1.9 |
| 16b | 120 |
| 17 | 14 |
| 18a | 89 |
| 18b | 15 |
| 19a | 4 |
| 19b | 290 |
| 20 | 37 |
| 21 | 71 |
| 22a | 6.6 |
| 22b | 270 |
| 23 | 110 |
| 24 | 340 |
| 25a | 170 |
| 25b | 1100 |

Inhibition of phosphodiesterase-3 (PDE3) has been shown to result in an increase in cardiovascular mortality in clinical trials (Movsesian M. A., Kukreja R. C. (2011) Phosphodiesterase Inhibition in Heart Failure. In: Francis S., Conti M., Houslay M. (eds) Phosphodiesterases as Drug Targets. Handbook of Experimental Pharmacology, vol 204. Springer, Berlin, Heidelberg. https://doi.org/10.1007/978-3-642-17969-3_10). Chronic treatment with PDE3 inhibitors has been shown to result in increased mortality, primarily as a result of arrhythmias and sudden death (*Expert Opinion on Investigational Drugs,* 2002, 11, 1529-1536*; J. of Cardiovasc. Trans. Res.,* 2010, 3, 507-515) and it may therefore be an advantage to as far as possible avoid PDE3 inhibitory activity.

PDE3 Assay

Evaluation of the effects of compounds on the activity of the human phosphodiesterase-3A is quantified by measuring the formation of 5'AMP from cAMP using a human recombinant enzyme expressed in a clonal isolate of *Spodoptera frugiperda* cells (Sf9) cells.

The test compound, reference compound or water (control) are added to a buffer containing 40 mM tris(hydroxymethyl)aminomethane (Tris)/HCl (pH 7.4) and 8 mM $MgCl_2$, 450 nMcAMP and 0.25 μCi [3H]cAMP.

Thereafter, the reaction is initiated by addition of the enzyme (about 1 U) and the mixture is incubated for 20 min at 22° C.

For basal control measurements, the enzyme is omitted from the reaction mixture.

Following incubation SPA beads are added. After 30 min at 22° C. under shaking, the amount of $[^3H]$5'AMP is quantified with a scintillation counter (Topcount, Packard).

The results are expressed as a percent inhibition of the control enzyme activity. The standard inhibitory reference compound is milrinone (CAS number 78415-72-2), which is tested in each experiment at several concentrations to obtain an inhibition curve from which its $IC_{50}$ value is calculated.

The PDE3 $IC_{50}$ values for Example compounds and reference compounds are set forth in Table 3 herein below.

TABLE 3

| Ex. No. | PDE3 IC50 (μM) |
|---|---|
| 3b | 11 |
| 4a | 3.8 |
| 4b | 6.5 |
| 5b | >100 |
| 6a | 2.9 |
| 6c | 2.5 |
| 6d | 3 |
| 7a | 2.2 |
| 9b | 4.6 |
| 16a | 29 |
| 17 | 3.5 |
| 19a | 22 |
| Ref Comp A* | 4 |
| Ref Comp B** | 11 |
| Ref Comp C*** | 2 |
| Ref Comp D**** | 5 |

*Ref Comp A may be prepared as disclosed in WO2020103815, Ex 19

**Ref Comp B may be prepared as disclosed in WO2018109607, Ex 4A-01

***Ref Comp C may be prepared as disclosed in WO2021112538, Ex 73 or as disclosed in WO2021081207, Ex 67, or as disclosed in WO2020263695, Ex 3.

***Ref Comp D may be prepared as disclosed in WO2020263695, Ex 2

The invention claimed is:

1. A compound of Formula (I), (I)

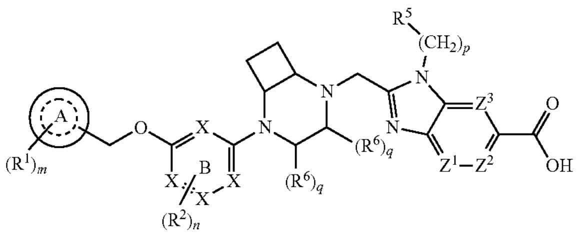

or a compound of Formula (II), (II)

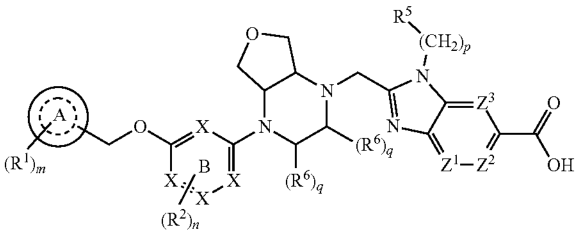

wherein

A is phenyl or pyridyl;

X is independently N or C, provided that no more than two atoms in the aromatic ring B are N;

$Z^1$ is N or $CR^3$;

$Z^2$ and $Z^3$ are each independently N or $CR^4$, provided that when $Z^1$ or $Z^3$ is N, $Z^2$ is $CR^4$;

$R^1$ is independently selected from F, Cl, Br, CN, $OCH_3$, $OCFH_2$, $OCF_2H$, $OCF_3$, $CH_3$, $CFH_2$, $CF_2H$ and $CF_3$;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$, $CFH_2$, $CF_2H$, $CF_3$, $OCH_3$, $OCFH_2$, $OCF_2H$ and $OCF_3$;

$R^5$ is selected from (4- to 6-membered)heterocycloalkyl, (5- to 6-membered)heteroaryl, CN, $C_{1-4}$alkyl, $O(C_{1-4}alkyl)$, $S(C_{1-4}alkyl)$, cyclopropyl, cyclobutyl, O(cyclopropyl) or S(cyclopropyl), wherein said (4- to 6-membered)heterocycloalkyl and (5- to 6-membered) heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

$R^6$ is independently selected from F, $C_{1-2}$alkyl and $OC_{1-2}$alkyl, wherein said $C_{1-2}$alkyl is substituted by 0, 1, 2 or 3 F;

m is 0, 1, 2 or 3;

n is 0 or 1;

p is 1, 2 or 3; and q is 0, 1 or 2;

or a pharmaceutically acceptable salt thereof.

2. The compound according to claim 1 of Formula (Ia)

(Ia)

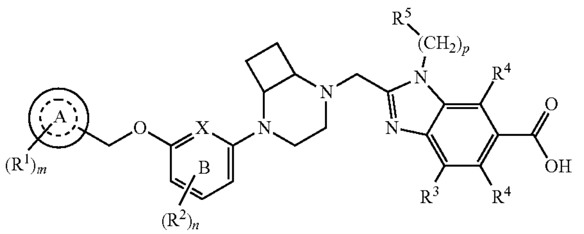

or Formula (IIa), (IIa)

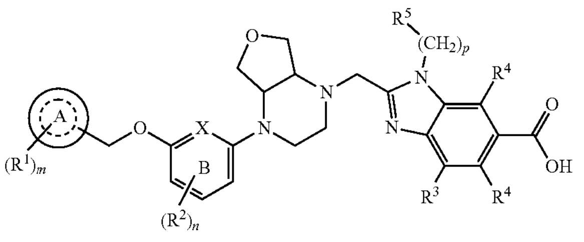

wherein

A is phenyl or pyridyl;

X is N or C;

$R^1$ is independently selected from F, Cl, Br, CN, $OCH_3$, $OCFH_2$, $OCF_2H$, $OCF_3$, $CH_3$, $CFH_2$, $CF_2H$ and $CF_3$;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$, $CFH_2$, $CF_2H$, $CF_3$, $OCH_3$, $OCFH_2$, $OCF_2H$ and $OCF_3$;

$R^5$ is selected from (4- to 6-membered)heterocycloalkyl, (5- to 6-membered)heteroaryl, CN, $C_{1-4}$alkyl, $O(C_{1-4}alkyl)$, $S(C_{1-4}alkyl)$, cyclopropyl, cyclobutyl, O(cyclopropyl) or S(cyclopropyl), wherein said (4- to 6-membered)heterocycloalkyl and (5- to 6-membered) heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

m is 0, 1, 2 or 3;

n is 0 or 1;

p is 1, 2 or 3; and q is 0, 1 or 2;

or a pharmaceutically acceptable salt thereof.

3. The compound according to claim 1, wherein

A is phenyl;

X is N;

$R^1$ is independently selected from F, Cl and CN;

$R^2$ is selected from F, Cl or CN;

$R^3$ is selected from H, F, Cl, $N(CH_3)_2$, $C_{1-2}$alkyl and $OC_{1-2}$alkyl, wherein said $C_{1-2}$alkyl is substituted by 0, 1, 2 or 3 F;

$R^4$ is independently selected from H, F, Cl, OH, $CH_3$ and $OCH_3$;

$R^5$ is selected from (4- to 6-membered)heterocycloalkyl, (5- to 6-membered)heteroaryl, CN, $C_{1-4}$alkyl, $O(C_{1-4}alkyl)$, $S(C_{1-4}alkyl)$, cyclopropyl, cyclobutyl, O(cyclopropyl) or S(cyclopropyl), wherein said (4- to 6-membered)heterocycloalkyl and (5- to 6-membered) heteroaryl is substituted by 0 or 1 substituent selected from $C_{1-2}$alkyl and wherein said $C_{1-4}$alkyl is substituted by 0 or 1 substituent selected from CN or $OCH_3$, and 0, 1, 2 or 3 F and wherein said cyclopropyl and cyclobutyl is substituted by 0 or 1 substituent selected from CN, $OCH_3$, $OCFH_2$, $OCF_2H$, $OCF_3$ and $CH_2CN$ and 0, 1, 2 or 3 F;

m is 0, 1 or 2;

n is 0 or 1; and p is 1, 2 or 3;

or a pharmaceutically acceptable salt thereof.

4. The compound according to claim 1 selected from:

2-(((1R,6S)-5-(6-((4-Cyano-2-fluorobenzyl)oxy)pyridin-2-yl)-2,5-diazabicyclo[4.2.0]octan-2-yl)methyl)-1-((1-methyl-1H-pyrazol-3-yl)methyl)-1H-benzo[d]imidazole-6-carboxylic acid, 2-(((1R*,6S*)-5-(6-((4-Cyano-2-fluorobenzyl)oxy)pyridin-2-yl)-2,5-diazabicyclo[4.2.0]octan-2-yl)methyl)-1-(((S)-oxetan-2-yl)methyl)-1H-benzo[d]imidazole-6-carboxylic acid, 2-(((1R*,6R*)-5-(6-((4-Cyano-2-fluorobenzyl)oxy)pyridin-2-yl)-2,5-diazabicyclo[4.2.0]octan-2-yl)methyl)-4-fluoro-1-(((S)-oxetan-2-yl)methyl)-1H-benzo[d]imidazole-6-carboxylic acid, 2-(((1R*,6R*)-5-(6-((4-Cyano-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylic acid, 2-(((1R*,6R*)-5-(6-((4-Cyano-2-fluorobenzyl)oxy)pyridin-2-yl)-2,5-diazabicyclo[4.2.0]octan-2-yl)methyl)-5-fluoro-1-(((S)-oxetan-2-yl)methyl)-1H-benzo[d]imidazole-6-carboxylic acid, rel-4-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, rel-5-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, rel-7-Chloro-2-(((1R,6S)-5-(6-((4-cyano-2-fluorobenzyl)oxy)pyridin-2-yl)-2,5-diazabicyclo[4.2.0]octan-2-yl)methyl)-1-(((R)-oxetan-2-yl)methyl)-1H-benzo[d]imidazole-6-carboxylic acid, 2-(((1R*,6R*)-5-(6-((4-Chloro-2-fluorobenzyl)oxy)pyridin-2-yl)-2,5-diazabicyclo[4.2.0]octan-2-yl)methyl)-4-methoxy-1-(((S)-oxetan-2-yl)methyl)-1H-benzo[d]imidazole-6-carboxylic acid, rac-1-(2-(tert-Butoxy)ethyl)-2-(((1R,6S)-5-(6-((4-cyano-2-fluorobenzyl)oxy)pyridin-2-yl)-2,5-diazabicyclo[4.2.0]octan-2-yl)methyl)-1H-benzo[d]imidazole-6-carboxylic acid, rac-1-(2-Butoxyethyl)-2-(((1R,6S)-5-(6-((4-cyano-2-fluorobenzyl)oxy)pyridin-2-yl)-2,5-diazabicyclo[4.2.0]octan-2-yl)methyl)-1H-benzo[d]imidazole-6-carboxylic acid, rel-2-(((1R,6R)-5-(6-((4-Chloro-2-fluorobenzyl)oxy)pyridin-2-yl)-2,5-diazabicyclo[4.2.0]octan-2-yl)methyl)-1-((1-ethyl-1H-imidazol-5-yl)methyl)-4-methoxy-1H-benzo[d]imidazole-6-carboxylic acid, rac-2-(((1R,6S)-5-(6-((4-Cyano-2-fluorobenzyl)oxy)pyridin-2-yl)-2,5-diazabicyclo[4.2.0]octan-2-yl)methyl)-1-((5-methylisoxazol-3-yl)methyl)-1H-benzo[d]imidazole-6-carboxylic acid, rac-2-(((1R,6S)-5-(6-((4-Cyano-2-fluorobenzyl)oxy)pyridin-2-yl)-2,5-diazabicyclo[4.2.0]octan-2-yl)methyl)-1-((4-methylpyridin-2-yl)methyl)-1H-benzo[d]imidazole-6-carboxylic acid, 2-(((4aRS,7aSR)-4-(6-((4-Chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid, 2-(((4aR*,7aS*)-4-(6-((4-Chloro-2-fluorobenzyl)oxy)pyridin-2-yl)hexahydrofuro[3,4-b]pyrazin-1(2H)-yl)methyl)-4-methoxy-1-(((S)-oxetan-2-yl)methyl)-1H-benzo[d]imidazole-6-carboxylic acid, 2-(((4aRS,7aSR)-4-(6-((4-Cyano-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid, rel-2-(((4aR,7aS)-4-(6-((4-Chloro-2-fluorobenzyl)oxy)pyridin-2-yl)hexahydrofuro[3,4-b]pyrazin-1(2H)-yl)methyl)-4-fluoro-1-(((S)-tetrahydrofuran-3-yl)methyl)-1H-benzo[d]imidazole-6-carboxylic acid, 2-(((4aR*,7aS*)-4-(6-((4-Chloro-2-fluorobenzyl)oxy)pyridin-2-yl)hexahydrofuro[3,4-b]pyrazin-1(2H)-yl)methyl)-4-fluoro-1-(((S)-oxetan-2-yl)methyl)-1H-benzo[d]imidazole-6-carboxylic acid, rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(oxazol-4-ylmethyl)-1H-benzo[d]imidazole-6-carboxylic acid, rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(pyridin-3-ylmethyl)-1H-benzo[d]imidazole-6-carboxylic acid, 4-Chloro-2-(((4aR*,7aS*)-4-(6-((4-chloro-2-fluorobenzyl)oxy)pyridin-2-yl)hexahydrofuro[3,4-b]pyrazin-1(2H)-yl)methyl)-1-(((S)-oxetan-2-yl)methyl)-1H-benzo[d]imidazole-6-carboxylic acid, rel-2-(((4aR,7aS)-4-(6-((4-Chloro-2-fluorobenzyl)oxy)pyridin-2-yl)hexahydrofuro[3,4-b]pyrazin-1(2H)-yl)methyl)-4-fluoro-1-(2-(2-methyl-1H-imidazol-1-yl)ethyl)-1H-benzo[d]imidazole-6-carboxylic acid, rel-4-Chloro-2-(((4aR,7aS)-4-(6-((4-chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylic acid, and rel-2-(((4aR,7aS)-4-(6-((4-Chloro-2-fluorobenzyl)oxy)pyridin-2-yl)hexahydrofuro[3,4-b]pyrazin-1(2H)-yl)methyl)-1-(2-(2-methyl-1H-imidazol-1-yl)ethyl)-1H-benzo[d]imidazole-6-carboxylic acid, or a pharmaceutically acceptable salt thereof.

5. A pharmaceutical composition comprising a compound according to claim 1, or a pharmaceutically acceptable salts thereof, in admixture with a pharmaceutically acceptable adjuvant, diluent or carrier.

6. A method of treating, or reducing the risk of, cardiovascular disease or metabolic conditions which comprises administering to a person suffering from or at risk of, said disease or condition, a therapeutically effective amount of a compound according to claim 1, or a pharmaceutically acceptable salt thereof.

7. The method according to claim 6, wherein said disease is type 2 diabetes.

* * * * *